(12) United States Patent
Mata-Fink et al.

(10) Patent No.: US 12,344,649 B2
(45) Date of Patent: Jul. 1, 2025

(54) MODULATORS OF PARATHYROID HORMONE RECEPTOR (PTHR1)

(71) Applicant: Flagship Pioneering Innovations VI, LLC, Cambridge, MA (US)

(72) Inventors: Jordi Mata-Fink, Happy Valley, OR (US); Le Phuong Ngo, Belmont, MA (US); Gevorg Grigoryan, Arlington, MA (US); Craig Owen MacKenzie, Bradford, VT (US); Kristen Park Hopson, Lincoln, MA (US)

(73) Assignee: Flagship Pioneering Innovations VI, LLC, Cambridge, MA (US)

( * ) Notice: Subject to any disclaimer, the term of this patent is extended or adjusted under 35 U.S.C. 154(b) by 644 days.

(21) Appl. No.: 17/633,764

(22) PCT Filed: Aug. 7, 2020

(86) PCT No.: PCT/US2020/045517
§ 371 (c)(1),
(2) Date: Feb. 8, 2022

(87) PCT Pub. No.: WO2021/030222
PCT Pub. Date: Feb. 18, 2021

(65) Prior Publication Data
US 2022/0298217 A1 Sep. 22, 2022

Related U.S. Application Data

(60) Provisional application No. 62/884,703, filed on Aug. 9, 2019.

(51) Int. Cl.
*C07K 14/635* (2006.01)
(52) U.S. Cl.
CPC .................. *C07K 14/635* (2013.01)
(58) Field of Classification Search
None
See application file for complete search history.

(56) References Cited

U.S. PATENT DOCUMENTS

| 6,921,750 B2 | 7/2005 | Dong |
| 7,803,770 B2 | 9/2010 | Dey et al. |
| 2013/0116180 A1 | 5/2013 | Gardella et al. |

FOREIGN PATENT DOCUMENTS

| WO | 2000/010596 A1 | 3/2000 |
| WO | 2004/067021 A1 | 8/2004 |
| WO | WO 2004/103273 A2 * | 12/2004 |
| WO | 2011/143406 A2 | 11/2011 |
| WO | 2021/030222 A1 | 2/2021 |

OTHER PUBLICATIONS

Adolfo Garcia-Ocana et al: "Parathyroid hormone-related protein increases DNA synthesis in proximal tubule cells by cyclic AMP- and protein kinase C-dependent pathways", Life Science, vol. 62, No. 25, May 1, 1998 (May 1, 1998), pp. 2267-2273, XP055737917.
Bernhardsson, M. and Aspenberg, P., "Abaloparatide versus teriparatide: a head to head comparison of effects on fracture healing in mouse models," Acta Orthopaedica, vol. 89; No. 6; 674-677 (2018).
Bohinc, B.N. and Gesty-Palmer, D., "Biased Agonism at the Parathyroid Hormone Receptor: A Demonstration of Functional Selectivity in Bone Metabolism," Min-Reviews in Medicinal Chemistry, vol. 12; 856-865 (2012).
Cheloha, R.W. et al., "PTH receptor-1 signalling-mechanistic insights and therapeutic prospects," Nat Rev Endocrinol., vol. 11; No. 12; 712-724 (2015).
D.T. Schermer et al: 11 Functional properties of a synthetic chicken parathyroid hormone-related protein 1-36 fragment 11 , Journal of Bone and Mineral Research, vol. 9, No. 7, Jul. 1, 1994 (Jul. 1, 1994), pp. 1041-1046, XP055738343.
Dean Thomas et al: "Altered selectivity of parathyroid hormone (PTH) and PTH-related protein (PTHrP) for distinct conformations of the PTH/PTHrP receptor", Molecular Endocrinology, the Endocrine Society, US, vol. 22, No. 1, Jan. 1, 2008 (Jan. 1, 2008), pp. 156-166, XP002600554.
Gardella, T.J. et al., "Inverse Agonism of Amino-Terminally Truncated Parathyroid Hormone (PTH) and PTH-Related Peptide (PTHrP) Analogs Revealed with Constitutively Active Mutant PTH/PTHrP Receptors," Endocrinology, vol. 137; 3936-3941 (1996).
Hattersley, G. et al., "Binding Selectivity of Abaloparatide for PTH-Type-1-Receptor Conformations and Effects on Downstream Signaling," Endocrinology, vol. 157; 141-149 (2016).
International Search Report and Written Opinion received for PCT Patent Application No. PCT/US20/45517, mailed on Nov. 25, 2020, 20 pages.
Kumar, M. et al., "A Bioluminescent-Based, HTS-Compatible Assay to Monitor G-Protein-Coupled Receptor Modulation of Cellular Cyclic Amp," Assay and Drug Development Technologies, vol. 5; No. 2; 237-245 (2007).
Lelovas, P.P. et al., "The Laboratory Rat as an Animal Model for Osteoporosis Research," Comparative Medicine, vol. 58; No. 5; 424-430 (2008).
M. E. Cupp et al: "Parathyroid Hormone (PTH) and PTH-Related Peptide Domains Contributing to Activation of Different PTH Receptor-Mediated Signaling Pathways", Journal of Pharmacology and Experimental Therapeutics, vol. 345, No. 3, Mar. 20, 2013 (Mar. 20, 2013), pp. 404-418, XP055426074.
Miller, P.D. et al., "Effect of Abaloparatide vs Placebo on New Vertebral Fractures in Postmenopausal Women with Osteoporosis a Randomized Clinical Trial," JAMA, vol. 316; No. 7; 722-733 (2016).

(Continued)

*Primary Examiner* — Elizabeth C. Kemmerer
(74) *Attorney, Agent, or Firm* — Hamilton, Brook, Smith & Reynolds, P.C.

(57) ABSTRACT

The invention provides, inter alia, synthetic parathyroid hormones (sPTHs) that can modulate the activity of parathyroid hormone receptor, such as parathyroid hormone receptor 1 (PTHR1). The invention also provides methods of modulating PTHR activity using these sPTHs, e.g., in a cell, such as a cell in an organism.

13 Claims, 3 Drawing Sheets

Specification includes a Sequence Listing.

(56) References Cited

OTHER PUBLICATIONS

Needleman, S.B. and Wunsch, C.D., "A General Method Applicable to the Search for Similarities in the Amino Acid Sequence of Two Proteins," J. Mol. Biol., vol. 48; 443-453 (1970).

Notification Concerning Transmittal of International Preliminary Report on Patentability for International Application No. PCT/US2020/045517, mailed Feb. 17, 2022.

Pearson, W.R. and Lipman, D.J., "Improved tools for biological sequence comparison," Proc. Natl. Acad. Sci., vol. 85; 2444-2448 (1988).

Pioszak, A.A. and Xu, "Molecular recognition of parathyroid hormone by its G-protein-coupled receptor," PNAS, vol. 105; No. 13; 5034-5039 (2008).

Pioszak, A.A. et al., "Structural Basis for Parathyroid Hormone-related Protein Binding to the Parathyroid Hormone Receptor and Design of Conformation-selective Peptides," The Journal of Biological Chemistry, vol. 284; No. 41; 28382-28391 (2009).

Saito, H. et al., "Progression of Mineral Ion Abnormalities in Patients with Jansen Metaphyseal Chondrodysplasia," J. Clin. Endocrinol Metab., vol. 103; No. 7; 2660-2669 (2018).

Shimizu N. et al: 11 Parathyroid hormone (PTH)-(1-14) and -(1-11) analogs conformationally constrained by alpha-aminoisobutyric acid mediate full agonist responses via the juxtamembrane region of the PTH-1 receptor 11 , Journal of Biological Chemistry, American Society for Biochemistry and Molecular Biology, US, vol. 276, No. 52, Dec. 28, 2001 (Dec. 28, 2001), pp. 49003-49012, XP002322156.

Shimizu, N. et al., "Novel Parathyroid Hormone (PTH) Antagonists That Bind to the Juxtamembrane Portion of the PTH/PTH-related Protein Receptor," The Journal of Biological Chemistry, vol. 280; No. 3; 1797-1807 (2006).

Smith, T.F. and Waterman, M.S., "Comparison of Biosequences," Advances in Applied Mathematics, vol. 2; 482-489 (1981).

T J Gardella et al.: "Determinants of [Arg2]PTH-(1-34) binding and signaling in the transmembrane region of the parathyroid hormone receptor.", Endocrinology, vol. 135, No. 3, Sep. 1, 1994 (Sep. 1, 1994), pp. 1186-1194, XP055737187.

Whitfield J F et al: "Parathyroid Hormone, Its Fragments and Their Analogs for the Treatment of Osteoporosis" , Treatments in Endocrinology, Adis International, Auckland, NZ, vol. 1, No. 3, Jan. 1, 2002 (Jan. 1, 2002) , pp. 175-190, XP008073017.

Zhao, L. et al., "Structure and dynamics of the active human parathyroid hormone receptor-1," Science, vol. 364; 148-153 (2019).

\* cited by examiner

MODULATORS OF PARATHYROID HORMONE RECEPTOR (PTHR1)

RELATED APPLICATION(S)

This application is the U.S. National Stage of International Application No. PCT/US2020/045517, filed Aug. 7, 2020, published in English, which claims the benefit of U.S. Provisional Application No. 62/884,703, filed on Aug. 9, 2019. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

File name: 57081028002_Sequence_Listing.txt; created Feb. 7, 2022, 57,468 Bytes in size.

BACKGROUND

Parathyroid Hormone Receptor (PTHR or PTH1R, HGNC:9608, human GeneID: 5745, HomoloGene: 267) is a G protein-coupled receptor (GPCR) that is expressed at high levels in bone and kidney and regulates calcium ion homeostasis. PTHR has two natural ligands: parathyroid hormone (PTH) and parathyroid hormone-related peptide (PTHrP). Alterations in PTHR biology play a role in many important diseases, including osteoporosis and other diseases of dysregulated calcium homeostasis. Diseases caused by inactivating mutations in PTHR include, for example, Blomstrand's lethal chondrodysplasia, Ollier diseases, familial primary failure of tooth eruption, and Eiken syndrome. Diseases caused by imbalances of ligands include brachydactyly type E and hypoparathyroidism. Osteoporosis, an imbalance between bone resorption and bone building processes, is also regulated by signaling through PTHR.

Therapeutic peptides based on the natural ligands of PTHR have been produced recombinantly and are approved as drugs for the treatment of osteoporosis: teriparatide (corresponding to the amino acids 1-34 of PTH, Eli Lilly) and abaloparatide (amino acids 1-34 of PTHrP, Radius health).

Despite their FDA approval and clinical use, both natural ligands have severe side effects. Both teriparatide and abaloparatide are marketed with a black-box label warning of the risk of osteosarcoma, and treatment with the drug is not recommended for more than two years over the course of a patient's lifetime. Additionally, extended exposure to teriparatide often triggers catabolic bone resorption in patients, counteracting the desired outcome of the treatment. Furthermore, these compounds do not address other disorders requiring, for example, antagonist or inverse agonist activity of PTHR.

SUMMARY

The invention disclosed herein is based, in part, on the discovery that polypeptides of the present invention specifically bind Parathyroid Hormone Receptor (PTHR). Accordingly, the invention generally relates to compositions (e.g., polypeptides, pharmaceutical compositions) and methods that are useful for modulating PTHR-mediated signaling in a cell.

Provided herein are polypeptides that specifically bind PTHR. In one aspect, the invention provides polypeptides that specifically bind PTHR, wherein the polypeptide comprises a synthetic parathyroid hormone (sPTH).

In some embodiments, the sPTH comprises a 14-amino acid sequence comprising:
  a) 1-3 polar residues and, relative to SEQ ID NO: 7, 1-14 amino acid substitutions;
  b) at least 4 polar residues, at least 1 charged residue, and, relative to SEQ ID NO: 7, 1-14 amino acid substitutions;
  c) at least 5 polar residues, at least 2 charged residues, and, relative to SEQ ID NO: 7, 1-14 amino acid substitutions;
  d) at least 5 polar residues, valine at position 2, and, relative to SEQ ID NO: 7, 1-13 amino acid substitutions; or
  e) at least 6 polar residues and, relative to SEQ ID NO: 7, 1-14 amino acid substitutions.

In some embodiments, the sPTH comprises a 32-amino acid sequence comprising:
  a) at most 13 polar residues and, relative to SEQ ID NO: 8, 1-32 amino acid substitutions;
  b) at least 14 polar residues, valine at position 2, and, relative to SEQ ID NO: 8, 1-31 substitutions;
  c) at least 14 polar residues and, relative to SEQ ID NO: 8, 22-28 amino acid substitutions; or
  d) positions 1-14 of SEQ ID NO: 8 and, relative to SEQ ID NO: 5, 1-18 amino acid substitutions at positions 15-32.

In some embodiments, the sPTH comprises an amino acid sequence having at least about 20% sequence identity to an amino acid sequence selected from SEQ ID NOs: 9-106 and SEQ ID NOs: 108-160. In some embodiments, the sPTH comprises an amino acid sequence selected from SEQ ID NOs: 9-106 and SEQ ID NOs: 108-160.

In some embodiments, the sPTH comprises an amino acid sequence having at least about 20% sequence identity to an amino acid sequence selected from SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160. In some embodiments, the sPTH comprises an amino acid sequence selected from SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160.

In some embodiments, the sPTH comprises an amino acid sequence having at least about 20% sequence identity to SEQ ID NO: 5.

In some embodiments, the sPTH comprises an amino acid sequence set forth by SEQ ID NO: 6. In some embodiments, the amino acid sequence set forth by SEQ ID NO: 6 is at the N-terminus of the sPTH. In some embodiments, the sPTH comprises an amino acid sequence having at least about 55% sequence identity to a sequence selected from the group consisting of SEQ ID NOs: 102-106 and SEQ ID NOs: 132-155.

In some embodiments, the sPTH comprises the amino acid sequence of SEQ ID NO: 107.

In some embodiments, the sPTH is an agonist of PTHR. In some embodiments, the sPTH is a biased agonist of PTHR. In some embodiments, the sPTH is an inverse agonist of PTHR. In some embodiments, the sPTH is an antagonist of PTHR.

In some embodiments, the polypeptides of the invention are fusion proteins.

In other aspects, the invention provides a polynucleotide encoding a polypeptide disclosed herein, a vector comprising such polynucleotide, and a host cell comprising such polynucleotide or vector.

In another aspect, the invention provides a method of modulating PTHR signaling in a mammalian cell, comprising contacting the mammalian cell with an effective amount of a polypeptide disclosed herein or a composition (e.g., pharmaceutical composition) comprising a polypeptide disclosed herein.

In another aspect, the invention provides a method of treating a subject in need thereof (e.g., a subject having Osteoporosis), comprising administering to the subject an effective amount of a polypeptide disclosed herein or a composition (e.g., pharmaceutical composition) comprising a polypeptide disclosed herein.

In another aspect, the invention provides a method of modulating PTHR signaling in a subject in need thereof (e.g., a subject having Osteoporosis), comprising administering to the subject an effective amount of a polypeptide disclosed herein or a composition (e.g., pharmaceutical composition) comprising a polypeptide disclosed herein.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

Figure 1:
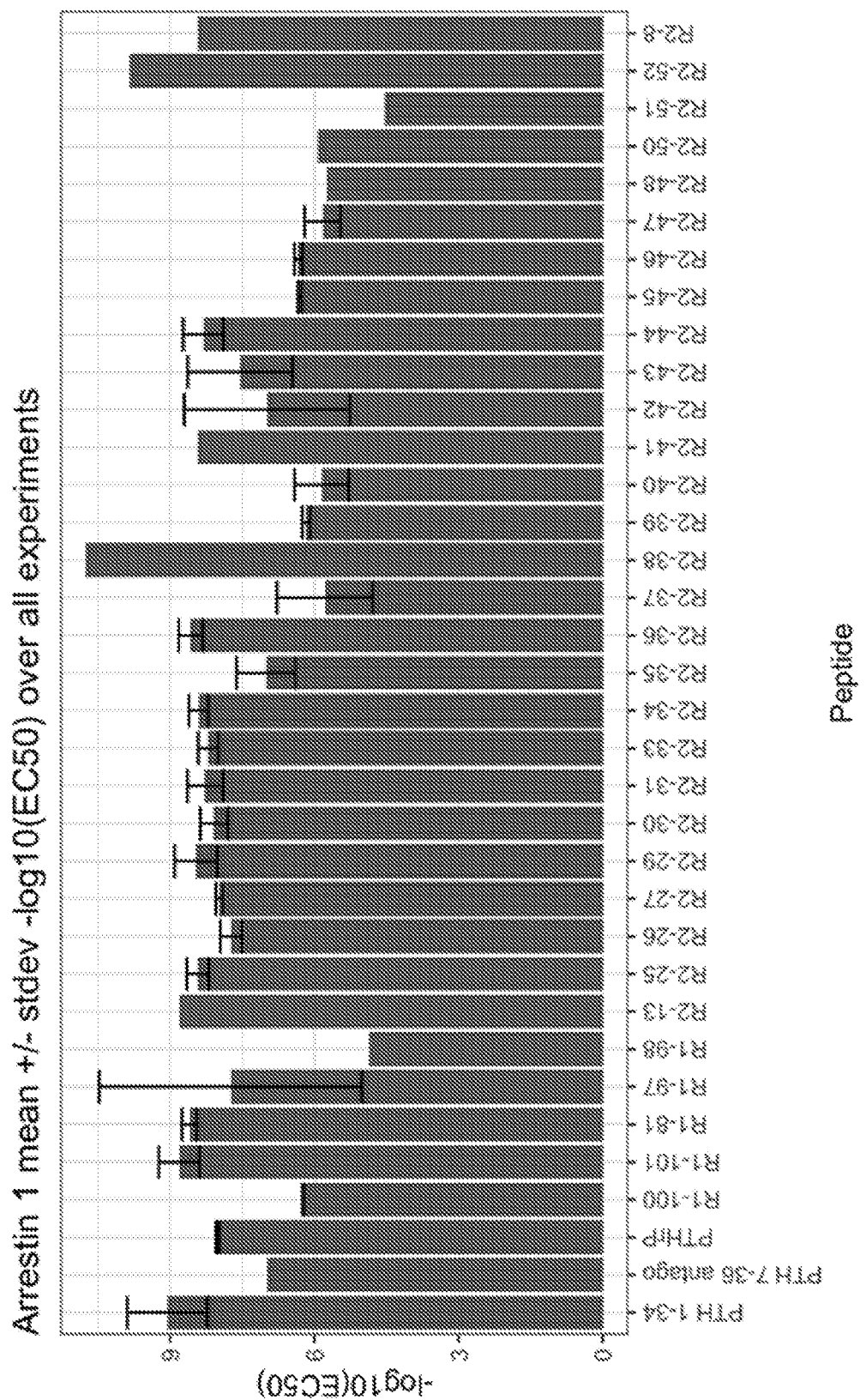
FIG. 1 depicts results of the β1-arrestin recruitment assay.

A description of example embodiments follows.

There is a need for novel ligands to PTHR that can modulate PTHR activity. The invention provides, inter alia, synthetic parathyroid hormones (sPTHs) that can modulate the activity of PTHR, as well as conjugates (e.g., comprising a heterologous moiety), fusion proteins, and compositions comprising the sPTHs, nucleic acids encoding the sPTHs, as well as methods of using the sPTHs, e.g., to modulate PTHR activity, for example, to treat disorders of calcium homeostasis and/or PTHR signaling.

PTH and Related Peptides

The native ligand of PTHR, PTH (HGNC: 9606), is a secreted peptide hormone that binds to PTHR. The peptide is comprised of a signal sequence and a pro-peptide fold that is cleaved, leaving an 84-amino acid active molecule (amino acids 32-115). The bioactive sequence for PTH is provided as SEQ ID NO: 1 (Table 1). A review of the biology of PTHR and its role in disease can be found in: Cheloha et al., Nature Reviews Endocrinology 11(12): 712-24 (2015).

A second native ligand of PTHR, PTHrP (HGNC: 9607), is a secreted peptide hormone that binds to PTHR. The peptide is comprised of a signal peptide, a pro-peptide, and a long chain that is endoproteolytically cleaved into three principal secretory forms, called PTHrP[1-36], PTHrP[38-94], and osteostatin (PTHrP[107-139]). The full sequence of PTHRrP is provided as SEQ ID NO: 2 (Table 1).

It is known from experimental results that the N-terminal 14 amino acids of PTH, PTH[1-14], engages with the receptor and drives signaling, whereas the C-terminal 20 amino acids, PTH[15-34], binds to the extracellular domain of PTHR and confers some amount of receptor specificity (Pioszak & Xu, Proc Natl Acad Sci USA. 105(13): 5034-39 (2008); Pioszak et al., J Biol Chem. 284(41): 28382-91 (2009)).

The sequence of the therapeutic peptide teriparatide, corresponding to amino acids 1-34 of the native ligand PTH is provided as SEQ ID NO: 3 (Table 1).

The sequence of the therapeutic peptide abaloparatide is provided as SEQ ID NO: 4 (Table 1), and corresponds to the first 20 amino acids of the native ligand PTHrP. Residues 21-34 have 50% diversity to the C-terminal 14 amino acids of PTHrP, including the unnatural amino acid 2-aminoisobutyric acid (annotated as "X").

The structure of PTHR was recently solved in complex with a peptide ligand, LA-PTH, that is a hybrid of PTH and PTHrP. See Zhao L H et al., *Science* 364: 148-53 (2019). The sequence of the 32-mer LA-PTH is provided as SEQ ID NO: 5, and the N-terminal 14-mer of LA-PTH is provided as SEQ ID NO: 6 (Table 1).

Consensus sequences encompassing the foregoing PTH and PTHrP sequences are provided in SEQ ID NO: 7 and SEQ ID NO: 8 (Table 1).

TABLE 1

| SEQ ID NO: | Name | Amino Acid Sequence |
|---|---|---|
| 1 | PTH | SVSEIQLMHNLGKHLNSMERVEWLRKKLQDVHNFVALGAPLAPRDAGSQ RPRKKEDNVLVESHEKSLGEADKADVNVLTKAKSQ |
| 2 | PTHRP | AVSEHQLLHDKGKSIQDLRRRFFLHHLIAEIHTAEIRATSEVSPNSKPSPNT KNHPVRFGSDDEGRYLTQETNKVETYKEQPLKTPGKKKKGKPGKRKEQE KKKRRTRSAWLDSGVTGSGLEGDHLSDTSTTSLELDSRRH |
| 3 | Teriparatide | SVSEIQLMHNLGKHLNSMERVEWLRKKLQDVHNF |
| 4 | Abaloparatide | VASEHQLLHDKGKSIQDLRRRELLEKLLXKLHTA (X = -aminoisobutyric acid) |
| 5 | LA-PM-FL | AVAEIQLMHQRAKWIQDARRRAFLHKLIAEIH |
| 6 | LA-PM | AVAEIQLMHQRAKW |
| 7 | 14-mer consensus | $X_1VX_2EX_3QLX_4HX_5X_6X_7KX_8$ ($X_1$: S/A; $X_2$: S/A; $X_3$: I/H; $X_4$: M/L; $X_5$: N/D/Q; $X_6$: L/K/R; $X_7$: G/A; $X_8$: H/S/W) |

TABLE 1 -continued

| SEQ ID NO: Name | Amino Acid Sequence |
|---|---|
| 8 32-mer consensus | $X_1VX_2EX_3QLX_4HX_5X_6X_7KX_8X_9X_{10}X_{11}X_{12}X_{13}RX_{14}X_{15}X_{16}LX_{17}X_{18}X_{19}X_{20}X_{21}X_{22}X_{23}H$<br>($X_1$: S/A; $X_2$: S/A; $X_3$: I/H; $X_4$: MIL; $X_5$: N/D/Q; $X_6$: L/K/R; $X_7$: G/A; $X_8$: H/S/W; $X_9$: L/I; $X_{10}$: N/Q; $X_{11}$: S/D; $X_{12}$: M/L/A; $X_{13}$: E/R; $X_{14}$: V/R; $X_{15}$: E/F/A; $X_{16}$: W/F/L; $X_{17}$: R/H/E; $X_{18}$: K/H; $X_{19}$: K/L; $X_{20}$: L/I; $X_{21}$: Q/A/aminoisobutyric acid; $X_{22}$: D/E/K; $X_{23}$: V/I/L.) |
| 161 PTH 7-36 antago | LMHNLGKHLNSMERVEWLRKKLQDVHNFVA | sPTHs Provided by the Invention

In one aspect, the invention provides a polypeptide that specifically binds PTHR, wherein the polypeptide comprises a synthetic parathyroid hormone (sPTH).

A "synthetic parathyroid hormone" or "sPTH" or "sPTH(s) provided by the invention" and the like refers to a polypeptide that binds the PTHR, comprises an amino acid sequence similar in size to the bioactive portion of the mature PTH peptide, and does not comprise, consist of, or consist essentially of the amino acid sequence of wild-type PTH (SEQ ID NO: 1), wild-type PTHrP (SEQ ID NO: 2), teriparatide (FORTEO®; SEQ ID NO: 3), abaloparatide (TYMLOS®; SEQ ID NO: 4), or "long acting" PTH (N-terminal 32-mer (SEQ ID NO: 5) or N-terminal 14-mer (SEQ ID NO:6)).

In certain embodiments, the sPTH provided by the invention does not comprise, consist of, or consist essentially of a consensus amino acid sequence set forth in SEQ ID NO: 7, SEQ ID NO: 8, and/or SEQ ID NO: 107. In some embodiments, the sPTH of the invention does not comprise, consist of, or consist essentially of an amino acid sequence disclosed in U.S. Pat. Nos. 6,921,750, 7,803,770, and/or WO/2000/010596. In some embodiments, the sPTH of the invention comprises, consists essentially of, or consists of an amino acid sequence encompassed by the consensus sequence of SEQ ID NO: 7, SEQ ID NO: 8 or SEQ ID NO: 107, and meeting one or more criteria set forth in Table 2. In some embodiments, the sPTH comprises the amino acid sequence of SEQ ID NO: 7. In some embodiments, the sPTH comprises the amino acid sequence of SEQ ID NO: 8. In some embodiments, the sPTH comprises the amino acid sequence of SEQ ID NO: 107.

TABLE 2

Categorizing Non-Limiting Examples of sPTH Polypeptides of the Invention

| Description | SEQ ID NOs. of Example Peptides Meeting Criteria |
|---|---|
| 14-mer polypeptide with 1-14 substitutions relative to SEQ ID NO: 7 | |
| with at most 3 polar residues and 1-14 substitutions | 9 |
| with at least 4 polar residues, at least 1 charged residue and 1-14 substitutions | 10-18 |
| with at least 5 polar residues, at least 2 charged residues and 1-14 substitutions | 19-30 |
| with at least 5 polar residues, position 2 as consensus (V/A/L) and 1-13 substitutions | 31-34 |
| with at least 6 polar residues and 1-14 substitutions | 35-87 |
| 32-mer polypeptide with 1-32 substitutions relative to SEQ ID NO: 8 | |
| with at most 13 polar residues and 1-32 substitutions | 88 |
| with at least 14 polar residues, position 2 as consensus (V/A/L), and 1-31 substitutions | 89, 90 |
| with at least 14 polar residues and 22-28 substitutions | 91-101 |
| positions 1-14 as consensus; positions 15-32 with at least 4 polar residues, at least 1 charged residue and 1-18 substitutions | 102-106 |

"Polar" amino acid residues include basic, acidic and hydrophilic but uncharged canonical amino acids and non-canonical amino acids. In certain embodiments, the polar residue is a canonical amino acid, e.g., basic (K, R, H), acidic (D, E) or hydrophilic but uncharged (S, T, N, Q, C). In some embodiments, the polar residue is a non-canonical amino acid.

"Charged" residues include basic and acidic canonical amino acids and non-canonical amino acids. In some embodiments, the charged residue is a canonical amino acid, e.g., basic (K, R, H) or acidic (D, E). In some embodiments, the charged residue is a non-canonical amino acid.

In some embodiments, the sPTH of the invention comprises, consists essentially of, or consists of an amino acid sequence selected from SEQ ID NOs: 9-106 and 108-159 (Table 3), or a variant thereof.

TABLE 3

Non-Limiting Examples of sPTH Polypeptides of the Invention

| SEQ ID NO: | Name | Amino Acid Sequence |
|---|---|---|
| 9 | 1 | VDFELWLLQFFLLF |
| 10 | B1 | VDFELFLLQQFLLF |
| 11 | B2 | VNVFLALLQHFLEW |
| 12 | B3 | INPELAALQFFWQL |
| 13 | B4 | VNPELAWLQFLHLL |
| 14 | B5 | INYELMTLTMLLIW |
| 15 | B6 | EDFELWLLRFFWLL |
| 16 | B7 | INVELAILEFFLQF |
| 17 | B8 | INFELMTLWFLHLL |
| 18 | B9 | TDPMLAALQFFAQL |
| 19 | C1 | AVFELWLLQHFHEW |
| 20 | C2 | VDYELMTLQQLLLF |
| 21 | C3 | TDVELAVLTFLHLF |
| 22 | C4 | IDWELMFLQQLHLF |
| 23 | C5 | TNYELAILQFFWEF |
| 24 | C6 | TDPELAALQMFWTW |
| 25 | C7 | TNVFLALLQHFWEW |
| 26 | C8 | VDYELMILQFFTSL |
| 27 | C9 | INWELMTLTMFHLW |
| 28 | C10 | IDYELMLLTFFTSF |
| 29 | C11 | IDYELMTLTFMTIL |
| 30 | C12 | TDVELAVLEFFWQF |
| 31 | D1 | TVVELATLQQLLLF |
| 32 | D2 | RVVELEILQQFLLF |
| 33 | D3 | RVPEIEALQQLLLF |
| 34 | D4 | TVVELATLQHFWLW |
| 35 | E1 | TDFELALLQHFAQW |
| 36 | E2 | RDIELEILEQFALW |
| 37 | E3 | ENFELNLLRFFAQW |
| 38 | E4 | VNFELFLLQQRWTF |
| 39 | E5 | IDFELWLLTQTADF |
| 40 | E6 | VDFELWLLSQLHSW |
| 41 | E7 | VDFELFLLQQTAQW |
| 42 | E8 | ENFEIWLLQHFAEW |
| 43 | E9 | RNVFIELLQQTALW |
| 44 | E10 | TNFELQLIQQLYLW |
| 45 | E1i | TNFEIALMQHFLEW |
| 46 | E12 | VDFEIFLLQQQALS |

TABLE 3 -continued

Non-Limiting Examples of sPTH Polypeptides of the Invention

| SEQ ID NO: | Name | Amino Acid Sequence |
|---|---|---|
| 47 | E13 | VDFELQLLQQTALW |
| 48 | E14 | MNVEIQLLQDFAQW |
| 49 | E15 | RPVELELLEQRALW |
| 50 | E16 | ENIEIYLLQQLAQW |
| 51 | E17 | LPVEITLLQQTAQW |
| 52 | E18 | VNFEIFLVQQTATW |
| 53 | E19 | TDFEIQLLQQFALW |
| 54 | E20 | VNWEIQLMQQVLQW |
| 55 | E21 | VPFELQLSTQRALW |
| 56 | E22 | TNYEIQLVWQTALW |
| 57 | E23 | TNWEIYLMQQSALW |
| 58 | E24 | MPYEIQLIQQTAQW |
| 59 | E25 | VDFEIQLLQQRALW |
| 60 | E26 | IDYEIYLSHQRALW |
| 61 | E27 | MPYEIQLMSQTADW |
| 62 | E28 | VHLEIQLMQQSALW |
| 63 | E29 | TNYEIQLILQRAIW |
| 64 | E30 | MNYEISLMRQRALW |
| 65 | E31 | VDFEIQLMQQRALW |
| 66 | E32 | LPLEITLLHQRAKW |
| 67 | E33 | KHWEIQLMQQRAAW |
| 68 | E34 | RHIEIWLMHQRALW |
| 69 | E35 | MPWEIQLMSQQAKW |
| 70 | E36 | MPAEIQLISQRADW |
| 71 | E37 | VDFEIQLMHQRALW |
| 72 | E38 | MPAEIRLMHERAKW |
| 73 | E39 | RVAEIQLMEQQALW |
| 74 | E40 | AHVEITLMWQRAKW |
| 75 | E41 | VNALIQHMHQRAKW |
| 76 | E42 | ESAEIQLMHQIAIW |
| 77 | E43 | TIPELATLQFFHQW |
| 78 | E44 | TIPEIATLQQTLIF |
| 79 | E45 | TIPEIETLQQMLIW |
| 80 | E46 | TIMEIATLQQTLIW |
| 81 | E47 | TIMEINTLQQFLIW |
| 82 | E48 | TIMEINTLQQMLIW |
| 83 | E49 | TIMEIETLQQMLIW |

TABLE 3 -continued

Non-Limiting Examples of sPTH Polypeptides of the Invention

| SEQ ID NO: | Name | Amino Acid Sequence |
|---|---|---|
| 84 | E50 | TIMEIETLDQFLYW |
| 85 | E51 | TIMEIETLDQMLIW |
| 86 | E52 | TIMEIETLDFMLIK |
| 87 | E53 | TIMEIEGLDQMLYK |
| 88 | F1 | VDFELWLLQQMLLFELYYEIIETLLKLIEEIF |
| 89 | G1 | TVFELWLLQQMWDFERRFEVLREFLKLLEEIF |
| 90 | G2 | TVFEIWLLQQMHDFEKRFEVLRMLLELLREIF |
| 91 | H1 | INFEIWLITQFHLFEKYYEIRETLLKLIEEIF |
| 92 | H2 | VDFEIWLLQQMWILRTLCERREELLKLIEEIF |
| 93 | H3 | IDYEIWLITQFAIFELNYERREELLKLIEEIF |
| 94 | H4 | VPFELWLLHQMLKFELDYERREELLKLIEEIF |
| 95 | H5 | VNFEIWLLQQRALEEALNRIRDFLLKLIEEIF |
| 96 | H6 | RDVEIELLEQLLQWIIDYRIREFLLKLIEEIF |
| 97 | H7 | RDVEIELLEQLAQWILDYRIREFLLKLIEEIF |
| 98 | H8 | TNFEIWLLSQLAKWIVEYRRREFLLKLIEEIF |
| 99 | H9 | VNFEIWLMQQLAQWIADYRRREELDKLIAEIF |
| 100 | H10 | IDYEIMLLHQLLKWIIDYRRREFLHKLIEEIF |
| 101 | H11 | VDFEIQLMQQRAQWIADYRIREFLDKLIAEIF |
| 102 | I1 (R1-100) | AVAEIQLMHQRAKWELEYELFEMFLKLLEEIF |
| 103 | I2 | AVAEIQLMHQRAKWRAEYELREMLLRLLEEIF |
| 104 | I3 (R1-97) | AVAEIQLMHQRAKWELEFELFREFLKLLVDFF |
| 105 | I4 | AVAEIQLMHQRAKWEYYYEILEMLLRLLREIY |
| 106 | I5 | AVAEIQLMHQRAKWELEYYLFETFLKMLEEVF |
| 107 | Reference | $X_1X_2X_3ELX_4X_5LQX_6X_7X_8X_9X_{10}$<br>($X_1$: V/T/A; $X_2$: DN; $X_3$: F/YN;<br>$X_4$: W/F/M/A; $X_5$: LIT; $X_6$: F/Q/H;<br>$X_7$: F/L/T; $X_8$: L/H/A; $X_9$: L/E/Q; $X_{10}$: F/W) |
| 108 | R2-1 | GVAELQLMHDLAKIRAEYELREMLLRLLEEIF |
| 109 | R2-2 | GVAMIQIMHDIAKIRAEYELREMLLRLLEEIF |
| 110 | R2-3 | GVAEIQLMHDIPVIRAEYELREMLLRLLEEIF |
| 111 | R2-4 | GVSMLQIMHDLAVIRAEYELREMLLRLLEEIF |
| 112 | R2-5 | GVALLQIVHDFAKIRAEYELREMLLRLLEEIF |
| 113 | R2-6 | AVATIQLMTDIAKIRAEYELREMLLRLLEEIF |
| 114 | R2-7 | GVAELQLMHFRALLRAEYELREMLLRLLEEIF |
| 115 | R2-8 | SVMMIQVMHDLAKIRAEYELREMLLRLLEEIF |
| 116 | R2-9 | GVVMLQFMHDVAKIRAEYELREMLLRLLEEIF |
| 117 | R2-10 | GVYAIQAMHDLAKIRAEYELREMLLRLLEEIF |
| 118 | R2-11 | GVAMLQILHDKAKVRAEYELREMLLRLLEEIF |
| 119 | R2-12 | GVAEIQLMVDLDIIRAEYELREMLLRLLEEIF |

TABLE 3 -continued

Non-Limiting Examples of sPTH Polypeptides of the Invention

| SEQ ID NO: | Name | Amino Acid Sequence |
|---|---|---|
| 120 | R2-13 | GIAVITLMDLRAYLRAEYELREMLLRLLEEIF |
| 121 | R2-14 | GIAVLTILDLRAKLRAEYELREMLLRLLEEIF |
| 122 | R2-15 | GVAVVTLMVLRAYYRAEYELREMLLRLLEEIF |
| 123 | R2-16 | LILVEQLMDLRAYLRAEYELREMLLRLLEEIF |
| 124 | R2-17 | GIAVFTIMHLRIYLRAEYELREMLLRLLEEIF |
| 125 | R2-18 | SIIGEQLMLLRALLRAEYELREMLLRLLEEIF |
| 126 | R2-19 | PIPVKDIMDLRAYLRAEYELREMLLRLLEEIF |
| 127 | R2-20 | NIAVEYIMLLRAYLRAEYELREMLLRLLEEIF |
| 128 | R2-21 | LILVKKIIDLRAYLRAEYELREMLLRLLEEIF |
| 129 | R2-22 | GIAVITIMIDYAKLRAEYELREMLLRLLEEIF |
| 130 | R2-23 | GIAVETLMELRAFVRAEYELREMLLRLLEEIF |
| 131 | R2-24 | GLAALTIGLLRAKLRAEYELREMLLRLLEEIF |
| 132 | R2-25 | AVAEIQLMHQRAKWKLELELKVKLLEILKDVY |
| 133 | R2-26 | AVAEIQLMHQRAKWGLELELKEKLRKILEDVY |
| 134 | R2-27 | AVAEIQLMHQRAKWKLDLELAVSLRKILEDVY |
| 135 | R2-28 | AVAEIQLMHQRAKWGLDLELAVKLQEILKDVL |
| 136 | R2-29 | AVAEIQLMHQRAKWKLELELKEKIRKLLEDLL |
| 137 | R2-30 | AVAEIQLMHQRAKWLEELKLKDDLRKILEDVY |
| 138 | R2-31 | AVAEIQLMHQRAKWGLDLELRARLREILRDVY |
| 139 | R2-32 | AVAEIQLMHQRAKWKQELELEEKNKKILEDVY |
| 140 | R2-33 | AVAEIQLMHQRAKWLNELRLKEEMRKILEDVY |
| 141 | R2-34 | AVAEIQLMHQRAKWRLEIELLKKLKEILKDVY |
| 142 | R2-35 | AVAEIQLMHQRAKWGVELQLKVDLRRILEDVY |
| 143 | R2-36 | AVAEIQLMHQRAKWKLELELKAFLDQILKDVL |
| 144 | R2-37 | AVAEIQLMHQRAKWEIQEIGIKITLELLKEYI |
| 145 | R2-38 | AVAEIQLMHQRAKWELLEELLKILLELLKEYI |
| 146 | R2-39 | AVAEIQLMHQRAKWELQEIGIKITLDLLEAYL |
| 147 | R2-40 | AVAEIQLMHQRAKWDLLIELVKLLHELLKEYI |
| 148 | R2-41 | AVAEIQLMHQRAKWEIQEIGIKITLDLLQTLK |
| 149 | R2-42 | AVAEIQLMHQRAKWAIQEIGIKITRELLERYL |
| 150 | R2-43 | AVAEIQLMHQRAKWELQEIGIAITLRLLARYI |
| 151 | R2-44 | AVAEIQLMHQRAKWSLREELEKLLKELLKEYI |
| 152 | R2-45 | AVAEIQLMHQRAKWGLEIELLKLLLSLLKEYI |
| 153 | R2-46 | AVAEIQLMHQRAKWSILEELLKILTALLDEYI |
| 154 | R2-47 | AVAEIQLMHQRAKWDVLIELAKLLAELLRRYH |
| 155 | R2-48 | AVAEIQLMHQRAKWKILEELLKILIDLLKQYI |
| 156 | R2-49 | GVAELQLMHDLAKIKLELELKVKLLEILKDVY |
| 157 | R2-50 | GVAMLQIMHDLAKIKQELELKDSMKKILEDVL |

TABLE 3 -continued

Non-Limiting Examples of sPTH Polypeptides of the Invention

| SEQ ID NO: | Name | Amino Acid Sequence |
|---|---|---|
| 158 | R2-51 | GIAVITLMVLRALLELQEIGRKITLELLKEYI |
| 159 | R2-52 | GIAVITLMLLRAYLELLEELVKILHELLRRYH |
| 160 | R1-103 | AVSEHQLLHDKGKSIQDLRRRFFLHHLIAEIHTY |

A "variant of a sPTH" polypeptide (e.g., a "variant" in reference to a sPTH), and the like, comprises an amino acid sequence with, for example, 1, 2, 3, 4, 5, 6, 7, 8, 9, 10, 11, 12, 13, or 14 amino acid substitutions (or more, in the case of longer sequences, such as 14, 15, 16, 17, 18, 19, 20, 21, 22, 23, 24, 25, 26, 27, 28, 29, 30, or 31) relative to a reference sequence (e.g., one of SEQ ID NOs: 9-107 or 108-160). In certain embodiments, a variant of an sPTH provided by the invention includes up to 1, 2, 3, 4, 5, 6, or 7 amino acid substitutions, e.g., 1-3 amino acid substitutions. A variety of amino acid substitutions for variants of a sPTH provided by the invention are possible, including substitution with non-canonical amino acids. Non-limiting examples of non-canonical amino acids include the D-isomers of any canonical amino acid (e.g., D-alanine), selenocysteine, pyrrolysine, β-alanine, 4-aminobutyric acid, 6-aminocaproic acid, sarcosine, statine, citrulline, homocitruline, homoserine, norleucine, norvaline, and ornithine. In some embodiments, the amino acid substitution is a conservative amino acid substitution. "Conservative substitutions" relative to a reference sequence means a given amino acid substitution has a value of 0 or greater in BLOSUM62. In some embodiments, the amino acid substitution is a highly conservative amino acid substitution. "Highly conservative substitutions" relative to a reference sequence means a given amino acid substitution has a value of 1 or greater (e.g., in some embodiments, 2, or more) in BLOSUM62.

In some embodiments, a "variant of a sPTH" polypeptide comprises an amino acid sequence that is at least about 50% identical to a sPTH provided by the invention (e.g., a sPTH of SEQ ID NOs: 9-106 or 108-160 (Table 3)). For example, the variant can be at least about: 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to a sPTH of any one or more of SEQ ID NOs: 9-106 and 108-160 (Table 3).

As used herein, the term "sequence identity," refers to the extent to which two nucleotide sequences, or two amino acid sequences, have the same residues at the same positions when the sequences are aligned to achieve a maximal level of identity, expressed as a percentage. For sequence alignment and comparison, typically one sequence is designated as a reference sequence, to which a test sequences are compared. The sequence identity between reference and test sequences is expressed as the percentage of positions across the entire length of the reference sequence where the reference and test sequences share the same nucleotide or amino acid upon alignment of the reference and test sequences to achieve a maximal level of identity. As an example, two sequences are considered to have 70% sequence identity when, upon alignment to achieve a maximal level of identity, the test sequence has the same nucleotide or amino acid residue at 70% of the same positions over the entire length of the reference sequence.

Alignment of sequences for comparison to achieve maximal levels of identity can be readily performed by a person of ordinary skill in the art using an appropriate alignment method or algorithm. In some instances, the alignment can include introduced gaps to provide for the maximal level of identity. Examples include the local homology algorithm of Smith & Waterman, *Adv. Appl. Math.* 2:482 (1981), the homology alignment algorithm of Needleman & Wunsch, *J. Mol. Biol.* 48:443 (1970), the search for similarity method of Pearson & Lipman, *Proc. Nat'l. Acad. Sci. USA* 85:2444 (1988), computerized implementations of these algorithms (GAP, BESTFIT, FASTA, and TFASTA in the Wisconsin Genetics Software Package, Genetics Computer Group, 575 Science Dr., Madison, Wis.), and visual inspection (see generally Ausubel et al., *Current Protocols in Molecular Biology*).

When using a sequence comparison algorithm, test and reference sequences are input into a computer, subsequent coordinates are designated, if necessary, and sequence algorithm program parameters are designated. The sequence comparison algorithm then calculates the percent sequence identity for the test sequence(s) relative to the reference sequence, based on the designated program parameters. A commonly used tool for determining percent sequence identity is Protein Basic Local Alignment Search Tool (BLASTP) available through National Center for Biotechnology Information, National Library of Medicine, of the United States National Institutes of Health. (Altschul et al., 1990).

In some embodiments, the sPTH comprises a 14-amino acid sequence comprising:
 a) 1-3 polar residues and, relative to SEQ ID NO: 7, 1-14 amino acid substitutions;
 b) at least 4 polar residues, at least 1 charged residue, and, relative to SEQ ID NO: 7, 1-14 amino acid substitutions;
 c) at least 5 polar residues, at least 2 charged residues, and, relative to SEQ ID NO: 7, 1-14 amino acid substitutions;
 d) at least 5 polar residues, valine at position 2, and, relative to SEQ ID NO: 7, 1-13 amino acid substitutions; or
 a) at least 6 polar residues and, relative to SEQ ID NO: 7, 1-14 amino acid substitutions.

In some embodiments, the sPTH comprises a 32-amino acid sequence comprising:
 a) at most 13 polar residues and, relative to SEQ ID NO: 8, 1-32 amino acid substitutions;
 b) at least 14 polar residues, valine at position 2, and, relative to SEQ ID NO: 8, 1-31 substitutions;

c) at least 14 polar residues and, relative to SEQ ID NO: 8, 22-28 amino acid substitutions; or d) positions 1-14 of SEQ ID NO: 8 and, relative to SEQ ID NO: 5, 1-18 amino acid substitutions at positions 15-32.

In some embodiments, the sPTH comprises an amino acid sequence having at least about 20% sequence identity to an amino acid sequence selected from SEQ ID NOs: 9-106 and SEQ ID NOs: 108-160. For example, having at least about: 25%, 30%, 35%, 40%, 45%, 50%, 55%, 60%, 65%, 70%, 75%, 80%, 85%, 90%, 95% or 97%; having about: 20-97%, 25-97%, 25-95%, 30-95%, 30-90%, 35-90%, 35-85%, 40-85%, 40-80%, 45-75%, 45-70%, 50-70%, 50-65% or 55-65%; or having up to about: 70%, 75%, 80%, 85%, 90%, 95% or 97%, sequence identity to an amino acid sequence selected from SEQ ID NOs: 9-106 and SEQ ID NOs: 108-160. In some embodiments, the sPTH comprises an amino acid sequence having about 50-97% sequence identity to an amino acid sequence selected from SEQ ID NOs: 9-106 and SEQ ID NOs: 108-160.

In some embodiments, the sPTH comprises at least 1 amino acid substitution relative to an amino acid sequence selected from SEQ ID NOs: 9-106 and SEQ ID NOs: 108-160. For example, the sPTH comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32; or about: 1-32, 1-28, 1-24, 1-20, 1-15, 1-10, 1-5, 2-32, 2-28, 2-24, 2-20, 2-15, 2-10, 2-5, 3-32, 3-28, 3-24, 3-20, 3-15, 3-10, 3-5, 4-32, 4-28, 4-24, 4-20, 4-15, 4-10 or 4-5 amino acid substitution relative to an amino acid sequence selected from SEQ ID NOs: 9-106 and SEQ ID NOs: 108-160.

In some embodiments, the sPTH comprises up to 32 amino acid substitutions relative to an amino acid sequence selected from SEQ ID NOs: 9-106 and SEQ ID NOs: 108-160. For example, the sPTH comprises up to: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31; or up to: 1-32, 1-28, 1-24, 1-20, 1-15, 1-10, 1-5, 2-32, 2-28, 2-24, 2-20, 2-15, 2-10, 2-5, 3-32, 3-28, 3-24, 3-20, 3-15, 3-10, 3-5, 4-32, 4-28, 4-24, 4-20, 4-15, 4-10 or 4-5 amino acid substitution relative to an amino acid sequence selected from SEQ ID NOs: 9-106 and SEQ ID NOs: 108-160.

In some embodiments, the sPTH comprises an amino acid sequence selected from SEQ ID NOs: 9-106 and SEQ ID NOs: 108-160.

In some embodiments, the sPTH comprises an amino acid sequence having at least about 20% sequence identity to an amino acid sequence selected from SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160. For example, having at least about: 25%, 30%, 35%, 40%, 45%, 50%, 55%, 60%, 65%, 70%, 75%, 80%, 85%, 90%, 95% or 97%; having about: 20-97%, 25-97%, 25-95%, 30-95%, 30-90%, 35-90%, 35-85%, 40-85%, 40-80%, 45-75%, 45-70%, 50-70%, 50-65% or 55-65%; or having up to about: 70%, 75%, 80%, 85%, 90%, 95% or 97%, sequence identity to an amino acid sequence selected from SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160. In some embodiments, the sPTH comprises an amino acid sequence having about 50-97% sequence identity to an amino acid sequence selected from SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160.

In some embodiments, the sPTH comprises at least 1 amino acid substitution relative to an amino acid sequence selected from SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160. For example, the sPTH comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32; or about: 1-32, 1-28, 1-24, 1-20, 1-15, 1-10, 1-5, 2-32, 2-31, 2-28, 2-24, 2-20, 2-18, 2-15, 2-10, 2-5, 3-32, 3-28, 3-24, 3-20, 3-15, 3-10, 3-5, 4-32, 4-28, 4-24, 4-20, 4-15, 4-10 or 4-5 amino acid substitution relative to an amino acid sequence selected from SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160.

In some embodiments, the sPTH comprises up to 32 amino acid substitutions relative to an amino acid sequence selected from SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160. For example, the sPTH comprises up to: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31; or up to: 1-32, 1-28, 1-24, 1-20, 1-15, 1-10, 1-5, 2-32, 2-31, 2-28, 2-24, 2-20, 2-18, 2-15, 2-10, 2-5, 3-32, 3-28, 3-24, 3-20, 3-15, 3-10, 3-5, 4-32, 4-28, 4-24, 4-20, 4-15, 4-10 or 4-5 amino acid substitution relative to an amino acid sequence selected from SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160.

In some embodiments, the sPTH comprises an amino acid sequence selected from SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160.

In some embodiments, the sPTH comprises an amino acid sequence having at least about 20% sequence identity to an amino acid sequence selected from SEQ ID NOs: 101, 103, 108, 115, 120, 121, 129, 131, 132, 134, 136-138, 140-143, 145, 147-152, 154, 155 and 157-160. For example, having at least about: 25%, 30%, 35%, 40%, 45%, 50%, 55%, 60%, 65%, 70%, 75%, 80%, 85%, 90%, 95% or 97%; having about: 20-97%, 25-97%, 25-95%, 30-95%, 30-90%, 35-90%, 35-85%, 40-85%, 40-80%, 45-75%, 45-70%, 50-70%, 50-65% or 55-65%; or having up to about: 70%, 75%, 80%, 85%, 90%, 95% or 97%, sequence identity to an amino acid sequence selected from SEQ ID NOs: 101, 103, 108, 115, 120, 121, 129, 131, 132, 134, 136-138, 140-143, 145, 147-152, 154, 155 and 157-160. In some embodiments, the sPTH comprises an amino acid sequence having about 50-97% sequence identity to an amino acid sequence selected from SEQ ID NOs: 101, 103, 108, 115, 120, 121, 129, 131, 132, 134, 136-138, 140-143, 145, 147-152, 154, 155 and 157-160.

In some embodiments, the sPTH comprises at least 1 amino acid substitution relative to an amino acid sequence selected from SEQ ID NOs: 101, 103, 108, 115, 120, 121, 129, 131, 132, 134, 136-138, 140-143, 145, 147-152, 154, 155 and 157-160. For example, the sPTH comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32; or about: 1-32, 1-28, 1-24, 1-20, 1-15, 1-10, 1-5, 2-32, 2-31, 2-28, 2-24, 2-20, 2-18, 2-15, 2-10, 2-5, 3-32, 3-28, 3-24, 3-20, 3-15, 3-10, 3-5, 4-32, 4-28, 4-24, 4-20, 4-15, 4-10 or 4-5 amino acid substitution relative to an amino acid sequence selected from SEQ ID NOs: 101, 103, 108, 115, 120, 121, 129, 131, 132, 134, 136-138, 140-143, 145, 147-152, 154, 155 and 157-160.

In some embodiments, the sPTH comprises up to 32 amino acid substitutions relative to an amino acid sequence selected from SEQ ID NOs: 101, 103, 108, 115, 120, 121, 129, 131, 132, 134, 136-138, 140-143, 145, 147-152, 154, 155 and 157-160. For example, the sPTH comprises up to: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31; or up to: 1-32, 1-28, 1-24, 1-20, 1-15, 1-10, 1-5, 2-32, 2-31, 2-28, 2-24, 2-20, 2-18, 2-15, 2-10, 2-5, 3-32, 3-28, 3-24, 3-20, 3-15, 3-10, 3-5, 4-32, 4-28, 4-24, 4-20, 4-15, 4-10 or 4-5 amino acid substitution relative to an amino acid sequence selected from SEQ ID NOs: 101, 103, 108, 115, 120, 121, 129, 131, 132, 134, 136-138, 140-143, 145, 147-152, 154, 155 and 157-160.

In some embodiments, the sPTH comprises an amino acid sequence selected from SEQ ID NOs: 101, 103, 108, 115, 120, 121, 129, 131, 132, 134, 136-138, 140-143, 145, 147-152, 154, 155 and 157-160.

In some embodiments, the sPTH consists of 28-36 amino acids, e.g., 18, 29, 30, 31, 32, 33, 35 or 36 amino acids. In some embodiments, the sPTH consists of 30-34 amino acids. In some embodiments, the sPTH consists of 32 amino acids.

In some embodiments, the sPTH comprises an amino acid sequence having at least about 20% sequence identity to SEQ ID NO: 5. For example, having at least about: 25%, 30%, 35%, 40%, 45%, 50%, 55%, 60%, 65%, 70%, 75%, 80%, 85%, 90%, 95% or 97%; having about: 20-97%, 25-97%, 25-95%, 30-95%, 30-90%, 35-90%, 35-85%, 40-85%, 40-80%, 45-75%, 45-70%, 50-70%, 50-65% or 55-65%; or having up to about: 70%, 75%, 80%, 85%, 90%, 95% or 97%, sequence identity to SEQ ID NO: 5. In some embodiments, the sPTH comprises an amino acid sequence having about 50-97% sequence identity to SEQ ID NO: 5.

In some embodiments, the sPTH comprises at least 1 amino acid substitution relative to SEQ ID NO: 5. For example, the sPTH comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32; or about: 1-32, 1-28, 1-24, 1-20, 1-15, 1-10, 1-5, 2-32, 2-31, 2-28, 2-24, 2-20, 2-18, 2-15, 2-10, 2-5, 3-32, 3-28, 3-24, 3-20, 3-15, 3-10, 3-5, 4-32, 4-28, 4-24, 4-20, 4-15, 4-10 or 4-5 amino acid substitution relative to SEQ ID NO: 5.

In some embodiments, the sPTH comprises up to 32 amino acid substitutions relative to SEQ ID NO: 5. For example, the sPTH comprises up to: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31; or up to: 1-32, 1-28, 1-24, 1-20, 1-15, 1-10, 1-5, 2-32, 2-31, 2-28, 2-24, 2-20, 2-18, 2-15, 2-10, 2-5, 3-32, 3-28, 3-24, 3-20, 3-15, 3-10, 3-5, 4-32, 4-28, 4-24, 4-20, 4-15, 4-10 or 4-5 amino acid substitution relative to SEQ ID NO: 5.

In some embodiments, the sPTH comprises an amino acid sequence set forth by SEQ ID NO: 6. In some embodiments, the amino acid sequence set forth by SEQ ID NO: 6 is at the N-terminus of the sPTH.

In some embodiments, the sPTH comprises an amino acid sequence having at least about 55% sequence identity to a sequence selected from the group consisting of SEQ ID NOs: 102-106 and SEQ ID NOs: 132-155. For example, having at least about: 60%, 65%, 70%, 75%, 80%, 85%, 90%, 95% or 97%; having about: 55-97%, 60-97%, 60-95%, 65-95%, 65-90%, 70-90%, 70-85% or 80-85%; or having up to about: 70%, 75%, 80%, 85%, 90%, 95% or 97%, sequence identity to a sequence selected from the group consisting of SEQ ID NOs: 102-106 and SEQ ID NOs: 132-155. In some embodiments, the sPTH comprises an amino acid sequence having about 50-97% sequence identity to a sequence selected from the group consisting of SEQ ID NOs: 102-106 and SEQ ID NOs: 132-155. In some embodiments, the sPTH comprises an amino acid sequence having about 75-97% sequence identity to a sequence selected from the group consisting of SEQ ID NOs: 102-106 and SEQ ID NOs: 132-155. In some embodiments, the sPTH comprises an amino acid sequence selected from the group consisting of SEQ ID NOs: 102-106 and SEQ ID NOs: 132-155.

In some embodiments, the at least amino acid substitution is a conservative substitution. In some embodiments, the at least amino acid substitution is a highly conservative substitution. In some embodiments, the amino acid substitutions are conservative substitutions. In some embodiments, the amino acid substitutions are highly conservative substitutions.

In some embodiments, the sPTH binds PTHR with an affinity that is at least about 5% higher than a polypeptide having an amino acid sequence consisting of SEQ ID NO: 1, SEQ ID NO: 2, SEQ ID NO: 3, SEQ ID NO: 4 or SEQ ID NO: 5. For example, the sPTH binds PTHR with an affinity that is at least about: 10%, 15%, 20%, 25%, 30%, 35%, 40%, 50%, 60% or 70% higher than a polypeptide having an amino acid sequence consisting of SEQ ID NO: 1, SEQ ID NO: 2, SEQ ID NO: 3, SEQ ID NO: 4 or SEQ ID NO: 5.

In some embodiments, the sPTH binds PTHR with an affinity that is at least about 5% lower than a polypeptide having an amino acid sequence consisting of SEQ ID NO: 1, SEQ ID NO: 2, SEQ ID NO: 3, SEQ ID NO: 4 or SEQ ID NO: 5. For example, the sPTH binds PTHR with an affinity that is at least about: 10%, 15%, 20%, 25%, 30%, 35%, 40%, 50%, 60% or 70% lower than a polypeptide having an amino acid sequence consisting of SEQ ID NO: 1, SEQ ID NO: 2, SEQ ID NO: 3, SEQ ID NO: 4 or SEQ ID NO: 5.

In some embodiments, no more than about 5% lower than a polypeptide having an amino acid sequence consisting of SEQ ID NO: 1, SEQ ID NO: 2, SEQ ID NO: 3, SEQ ID NO: 4 or SEQ ID NO: 5. For example, the sPTH binds PTHR with an affinity that is no more than about: 10%, 15%, 20%, 25%, 30%, 35%, 40%, 50%, 60% or 70% lower than a polypeptide having an amino acid sequence consisting of SEQ ID NO: 1, SEQ ID NO: 2, SEQ ID NO: 3, SEQ ID NO: 4 or SEQ ID NO: 5.

In some embodiments, the sPTH provided by the invention or variant thereof includes a post-translational modification, such as one or more post-translational modifications resulting from acetylation, amidation, formylation, glycosylation, hydroxylation, methylation, myristoylation, phosphorylation, deamidation, prenylation (e.g., farnesylation, geranylation, etc.), ubiquitination, ribosylation or sulfation of the sPTH or variant thereof, or any combination of the foregoing.

The sPTH polypeptide of the invention can function as an agonist (e.g., a biased agonist), an inverse agonist or an antagonist of one or more PTHR signaling pathways. In some embodiments, the one or more PTHR signaling pathways are selected from the group consisting of the Gαs-adenylyl cyclase-cAMP-protein kinase A (PKA) pathway ($G_s$ pathway), the Gα$_q$-phospholipase C (PLC) β-inositol triphosphate-cytoplasmic $Ca^{2+}$-protein kinase C pathway ($G_q$ pathway), the Gα$_{12/13}$-phospholipase D-transforming protein RhoA pathway ($G_{12/13}$ pathway), the β-arrestin-extracellular signal-regulated kinase 1/2 (ERK1/2) pathway (β-arrestin pathway), and the combinations thereof. In some embodiments, the PTHR signaling pathway comprises the Gαs-adenylyl cyclase-cAMP-protein kinase A (PKA) pathway ($G_s$ pathway). In some embodiments, the PTHR signaling pathway comprises the Gα$_q$-phospholipase C (PLC) β-inositol triphosphate-cytoplasmic Ca$^{2+}$-protein kinase C pathway (G$_q$ pathway). In some embodiments, the PTHR signaling pathway comprises the Gα$_{12/13}$-phospholipase D-transforming protein RhoA pathway (G$_{12/13}$ pathway). In some embodiments, the PTHR signaling pathway comprises the β-arrestin-extracellular signal-regulated kinase 1/2 (ERK1/2) pathway (β-arrestin pathway). Additional examples of PTHR signaling pathways are described in Cheloha R W et al., *Nat Rev Endocrinol.* 11(12): 712-24 (2015), the contents of which are incorporated by reference in their entirety.

In some embodiments, the sPTH polypeptide of the invention functions as an agonist of one or more PTHR signaling pathways. An "agonist of PTHR" binds to and activates PTHR signaling. An agonist of PTHR provided by the invention can be used, inter alia, to boost bone mass, increase bone formation, and/or reduce fractures in subjects (e.g., human patients) with osteoporosis or at increased risk for osteoporosis.

In some embodiments, a sPTH polypeptide that is an agonist of PTHR has improved activity (e.g., about: 1.1-fold, 1.2-fold, 1.3-fold, 1.4-fold, 1.5-fold or greater activity) compared to a reference PTH polypeptide (e.g., PTH 1-34). In certain embodiments, a sPTH polypeptide that is an agonist of PTHR has equivalent or similar activity (e.g., about: 90, 95, 97, 98, 99 or 100% activity) compared to a reference PTH polypeptide (e.g., PTH 1-34). Non-limiting examples of activities include signaling activity through, e.g., the Gs pathway, the Gq pathway, the G12/13 pathway, the β-arrestin pathway and combinations thereof.

In some embodiments, a sPTH polypeptide that is an agonist of PTHR has a lower binding constant (K$_D$) value to PTHR (e.g., about: 95%, 90%, 85%, 80%, 75%, 70%, 65%, 60%, 55%, 50% or lower) compared to a reference PTH polypeptide (e.g., PTH 1-34). In certain embodiments, a sPTH polypeptide that is an agonist of PTHR has equivalent or similar K$_D$ value (e.g., about: 96%, 97%, 98%, 99%, 100%, 102%, 105% or 110%) compared to a reference PTH polypeptide (e.g., PTH 1-34). As used herein the term "K$_D$," also referred to as "binding constant," "equilibrium dissociation constant" or "affinity constant," is a measure of the extent of a reversible association between two molecular species (e.g., antibody and target protein) and includes both the actual binding affinity as well as the apparent binding affinity. Binding affinity can be determined using methods known in the art including, for example, by measurement of surface plasmon resonance, e.g., using a Biolayer interferometry (Octet, ForteBio) or a surface plasmon resonance (Biacore) system and assay. A reference that compares various surface technologies for measuring binding affinity and kinetics is Yang et al., Analytical Biochemistry 508: 78-96 (2016), the contents of which are incorporated by reference herein in their entirety.

In some embodiments, a sPTH polypeptide that is an agonist of PTHR comprises more than 14 amino acids (e.g., 32 amino acids, 34 amino acids), wherein the N-terminal 14 amino acids of the polypeptide correspond to SEQ ID NO: 6.

Particular examples of sPTH polypeptides that are agonists of PTHR include SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160. See, e.g., Example 6 herein.

In some embodiments, the sPTH polypeptide of the invention is selected from the group consisting of SEQ ID NO: 120, SEQ ID NO: 136, SEQ ID NO: 143, SEQ ID NO: 145 and SEQ ID NO: 159. In some embodiments, the sPTH polypeptide of the invention is SEQ ID NO: 145 or SEQ ID NO: 159. In some embodiments, the sPTH polypeptide of the invention is selected from the group consisting of SEQ ID NO: 108, SEQ ID NO: 115, SEQ ID NO: 131, SEQ ID NO: 136, SEQ ID NO: 137, SEQ ID NO: 138, SEQ ID NO: 139, SEQ ID NO: 140, SEQ ID NO: 141, SEQ ID NO: 143, SEQ ID NO: 149, SEQ ID NO: 155 and SEQ ID NO: 157. In some embodiments, the sPTH polypeptide of the invention is selected from the group consisting of SEQ ID NO: 108, SEQ ID NO: 115, SEQ ID NO: 131, SEQ ID NO: 136, SEQ ID NO: 143, SEQ ID NO: 155 and SEQ ID NO: 157. In some embodiments, the sPTH polypeptide of the invention is selected from the group consisting of SEQ ID NO: 101, SEQ ID NO: 103, SEQ ID NO: 120, SEQ ID NO: 121, SEQ ID NO: 129, SEQ ID NO: 131, SEQ ID NO: 132, SEQ ID NO: 134, SEQ ID NO: 142, SEQ ID NO: 143, SEQ ID NO: 147, SEQ ID NO: 148, SEQ ID NO: 150, SEQ ID NO: 151, SEQ ID NO: 152, SEQ ID NO: 154, SEQ ID NO: 158 and SEQ ID NO: 160. In some embodiments, the sPTH polypeptide of the invention is selected from the group consisting of SEQ ID NO: 101, SEQ ID NO: 120, SEQ ID NO: 121, SEQ ID NO: 129, SEQ ID NO: 131, SEQ ID NO: 147, SEQ ID NO: 148, SEQ ID NO: 150, SEQ ID NO: 151, SEQ ID NO: 152, SEQ ID NO: 154, SEQ ID NO: 158 and SEQ ID NO: 160.

In some embodiments, the sPTH polypeptide of the invention functions as a biased agonist of one or more PTHR signaling pathways. A "biased agonist of PTHR" binds to PTHR and preferentially activates a distinct subset of the intracellular signaling responses that are usually activated by the parent ligand or induce alterations in the duration and cellular localization of signaling. See, e.g., Cheloha R W et al., *Nat Rev Endocrinol.* 11(12): 712-24 (2015) for additional description. In some embodiments, the sPTH polypeptide acting as a PTHR biased agonist induces selective activation of one pathway independently of one or more other pathways. For example, the sPTH polypeptide acting as a PTHR biased agonist induces selective activation of the β-arrestin pathway without inducing activation of one or more of the G protein-coupled signaling mechanisms (G$_s$ pathway, G$_q$ pathway, or G$_{12/13}$ pathway or any combination of the foregoing). As such, a PTHR biased agonist can be used to selectively induce anabolic bone formation and improve therapeutic efficacy with reduced side effects in subjects (e.g., human patients) with osteoporosis or at increased risk for osteoporosis. In some embodiments, the sPTH polypeptide of the invention is a variant of a reference biased agonist. Non-limiting examples of reference biased agonists include D-Trp12 (D-Trp at position 12) and Tyr34-PTH (7-34) (Tyr at position 34) on the PTH(7-34) scaffold. See, for example Bohinc B N and Gesty-Palmer D, *Mini Rev Med Chem.* 12(9): 856-65 (2012).

In some embodiments, the sPTH polypeptide of the invention functions as an inverse agonist of one or more PTHR signaling pathways. An "inverse agonist of PTHR" is a polypeptide that can bind to PTHR and inhibit a constitutively active PTHR or reduce basal PTHR signaling. See, e.g., Cheloha R W et al., *Nat Rev Endocrinol.* 11(12): 712-24 (2015). In some embodiments, the sPTH polypeptide acting as a PTHR inverse agonist is used to inhibit and/or reverse excessive activation of PTHR due to gain-of-function mutations. In some embodiments, the sPTH polypeptide acting as a PTHR inverse agonist is used to treat and/or prevent one or more indications. Non-limiting examples of the indication include Jansen's metaphyseal chondrodysplasia, hypercalcemia, hypercalciuria, nephrocalcinosis, and chronic kidney disease. See, for example, Saito H et al., *J Clin Endocrinol Metab.* 49: 20-28 (2018).

In some embodiments, the sPTH polypeptide of the invention functions as an antagonist of one or more PTHR signaling pathways. An "antagonist of PTHR" is a polypeptide that binds to PTHR and prevents alterations of PTHR signaling by agonists or inverse agonists. See, e.g., Cheloha R W et al., *Nat Rev Endocrinol.* 11(12): 712-24 (2015). In some embodiments, the sPTH polypeptide acting as a PTHR antagonistic is used to inhibit excessive activation of PTHR. In some embodiments, the sPTH polypeptide acting as a PTHR antagonistic is used to treat and/or prevent one or more indications. Non-limiting examples of the indication include including hypercalcemia, hyperparathyroidism, parathyroid carcinoma, and metastatic bone disease. See, for example, Mirza A M et al., *AACR Annual Meeting* 2017.

In some embodiments, PTHR signaling is assessed by a luciferase assay, which can be performed according to Hattersly et al., *Endocrinology* 157(1): 141-49 (2016) or Kumar et al., 2007, incorporated by reference in their entirety. A sPTH polypeptide mediated effect (e.g., an agonist activity or an inverse agonist activity) on PTHR signaling can be assessed, for example, through a FRET (fluorescence resonance energy transfer) assay. For example, with a luciferase-tagged β-arrestin and a YFP-tagged GPCR. In some embodiments, a sPTH polypeptide mediated effect (e.g., an inverse agonist activity or an antagonist activity) is evaluated by detecting a reduction in cAMP level. In some embodiments (e.g., an inverse agonist activity), a background cAMP level is determined using a constitutively active receptor, e.g., containing one or more constitutive mutations. Non-limiting examples of the constitutive mutations include H223R, T410P, or I458R or a combination thereof, which underlies Jansen's metaphyseal chondrodysplasia. In some embodiments (e.g., an antagonist activity), a background cAMP level is determined using a native ligand. Detailed descriptions of assays can be found in Example 2B (antagonist activity) and Example 2C (inverse agonist activity).

In some embodiments, the sPTH polypeptide is conjugated to a heterologous moiety. The term "conjugated" refers to attached, via a covalent or noncovalent interaction. Conjugation can employ any of suitable linking agents. Non-limiting examples include peptide linkers, compound linkers, and chemical cross-linking agents.

In some embodiments, the heterologous moiety is a therapeutic agent, a diagnostic agent or a combination thereof. In some embodiments, the heterologous moiety is polyethylene glycol (PEG), hexadecanoic acid, hydrogels, nanoparticles, multimerization domains and carrier peptides.

In some embodiments, the nanoparticle is a lipid nanoparticle. In some embodiments, the nanoparticle is a polymer nanoparticle. In some embodiments, the polymer is an amphiphilic polymer. In other embodiments, the polymer is a hydrophobic or hydrophilic polymer. Non-limiting examples of polymers include poly(lactic acid)-poly(ethylene glycol), poly(lactic-co-glycolic acid)-poly(ethylene glycol), poly(lactic-co-glycolic) acid (PLGA), poly(lactic-co-glycolic acid)-d-α-tocopheryl polyethylene glycol succinate, poly(lactic-co-glycolic acid)-ethylene oxide fumarate, poly(glycolic acid)-poly(ethylene glycol), poly-caprolactone-poly(ethylene glycol), or any salts thereof. In some embodiments, the polymer nanoparticle comprises poly(lactic-co-glycolic) acid (PLGA).

Fusion Proteins

In another aspect, the invention provides a fusion protein comprising one or more of the SPTHs described herein.

The term "fusion protein" refers to a synthetic, semi-synthetic or recombinant single protein molecule. A fusion protein can comprise all or a portion of two or more different proteins and/or polypeptides that are attached by covalent bonds (e.g., peptide bonds).

Fusion proteins of the invention can be produced recombinantly or synthetically, using routine methods and reagents that are well known in the art. For example, a fusion protein of the invention can be produced recombinantly in a suitable host cell (e.g., bacteria) according to methods known in the art. See, e.g., *Current Protocols in Molecular Biology*, Second Edition, Ausubel et al. eds., John Wiley & Sons, 1992; and *Molecular Cloning: a Laboratory Manual*, 2nd edition, Sambrook et al., 1989, Cold Spring Harbor Laboratory Press. For example, a nucleic acid molecule comprising a nucleotide sequence encoding a fusion protein described herein can be introduced and expressed in suitable host cell (e.g., *E. coli*), and the expressed fusion protein can be isolated/purified from the host cell (e.g., in inclusion bodies) using routine methods and readily available reagents. For example, DNA fragments coding for different protein sequences (e.g., a light-responsive domain, a heterologous peptide component) can be ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers that give rise to complementary overhangs between two consecutive nucleic acid fragments that can subsequently be annealed and re-amplified to generate a chimeric nucleic acid sequence (see Ausubel et al., Current Protocols in Molecular Biology, 1992).

Nucleic Acids, Expression Vectors, Expression Host Cells

In another aspect, the invention provides one or more polynucleotides encoding any one of the SPTH polypeptides or fusion proteins described herein. In some embodiments, the SPTH polypeptide or fusion protein of the invention is encoded by a single polynucleotide. In some embodiments, the SPTH polypeptide or fusion protein of the invention is encoded by multiple polynucleotides.

In some embodiments, the SPTH polynucleotide comprises a nucleotide sequence that is codon-optimized for a chosen host cell.

In another aspect, the invention provides an expression vector comprising any one or more of the polynucleotides described herein.

The term "expression vector" refers to a replicable nucleic acid from which one or more proteins can be expressed when the expression vector is transformed into a suitable expression host cell.

In some embodiments, the expression vector further comprises an expression control polynucleotide sequence operably linked to the polynucleotide, a polynucleotide sequence encoding a selectable marker, or both. In some embodiments, the expression control polynucleotide sequence comprises a promoter sequence, an enhancer sequence, or both. In some embodiments, the expression control polynucleotide sequence comprises an inducible promoter sequence. The term "promoter" refers to a region of DNA to which RNA polymerase binds and initiates the transcription of a gene. The term "operably linked" means that the nucleic acid is positioned in the recombinant polynucleotide, e.g., vector, in such a way that enables expression of the nucleic acid under control of the element (e.g., promoter) to which it is linked. The term "selectable marker element" is an element that confers a trait suitable for artificial selection. Selectable marker elements can be negative or positive selection markers.

In another aspect, the invention provides an expression host cell comprising any one or more of the polynucleotides or expression vectors described herein.

The term "expression host cell" refers to a cell useful for receiving, maintaining, reproducing and/or amplifying a vector.

Non-limiting examples of expression host cells include mammalian cells such as Chinese hamster ovary (CHO) cells, COS cells, human embryonic kidney (HEK), yeast cells such as *Pichia pastoris* cells, or bacterial cells such as DH5α, etc.

Compositions

In another aspect, the invention provides a composition comprising any one of the polypeptides or fusion proteins described herein. In some embodiments, the composition is a pharmaceutical composition.

In some embodiments, the composition (e.g., pharmaceutical composition) further comprises pharmaceutically acceptable carriers, excipients, stabilizers, diluents or tonifiers (Remington's Pharmaceutical Sciences 16th edition, Osol, A. Ed. (1980)). Suitable pharmaceutically acceptable carriers, excipients, or stabilizers are nontoxic to recipients at the dosages and concentrations employed. Non-limiting examples of pharmaceutically acceptable carriers, excipients, stabilizers, diluents or tonifiers include buffers (e.g., phosphate, citrate, histidine), antioxidants (e.g., ascorbic acid or methionine), preservatives, proteins (e.g., serum albumin, gelatin or immunoglobulins); hydrophilic polymers, amino acids, carbohydrates (e.g., monosaccharides, disaccharides, glucose, mannose or dextrins); chelating agents (e.g., EDTA), sugars (e.g., sucrose, mannitol, trehalose or sorbitol), salt-forming counter-ions (e.g., sodium), metal complexes (e.g., Zn-protein complexes); non-ionic surfactants (e.g., Tween), PLURONICS™ and polyethylene glycol (PEG).

In some embodiments, the composition (e.g., pharmaceutical composition) of the invention is formulated for a suitable administration schedule and route. Non-limiting examples of administration routes include oral, rectal, mucosal, intravenous, intramuscular, subcutaneous and topical, etc. In some embodiments, the composition (e.g., pharmaceutical composition) of the invention is stored in the form of an aqueous solution or a dried formulation (e.g., lyophilized).

In some embodiments, the composition is formulated to be administered by infusion (e.g., intravenous infusion). In some embodiments, the composition is formulated to be administered with a second therapeutic agent as a combination therapy.

Methods of Making a sPTH

The SPTH polypeptides, the conjugates thereof, the fusion proteins thereof and the compositions of the invention can be produced by any suitable means known in the art. In some embodiments, a method of chemical synthesis is used. In some embodiments, a method of recombinant production/expression is used. In some embodiments, a combination of chemical synthesis and recombinant production/expression is used. For example, the SPTH polypeptide component is recombinantly produced followed by chemically conjugating a heterologous moiety. In some embodiments, a host cell of the invention (e.g., comprising a SPTH polynucleotide or expression vector of the invention) is cultured under suitable conditions to generate the sPTH, which is then isolated from the host cell or culture supernatant, thereby producing the sPTH.

Methods Using a sPTH

In another aspect, the invention provides a method of modulating PTHR signaling in a cell (e.g., a mammalian cell), comprising contacting the cell with an effective amount of the polypeptide, fusion protein or composition (e.g., pharmaceutical composition) described herein.

In another aspect, the invention provides a method of modulating PTHR signaling in a subject in need thereof, comprising administering an effective amount of the polypeptide, fusion protein or composition (e.g., pharmaceutical composition) described herein to the subject.

In some embodiments, modulating PTHR signaling involves an agonist activity (e.g., a biased agonist activity), an inverse agonist activity, or an antagonist activity of PTHR signaling or a combination of the forgoing. In some embodiments, modulating PTHR signaling involves an agonist activity of PTHR signaling. In some embodiments, modulating PTHR signaling involves a biased agonist activity of PTHR signaling. In some embodiments, modulating PTHR signaling involves an inverse agonist activity of PTHR signaling. In some embodiments, modulating PTHR signaling involves an antagonist activity of PTHR signaling.

In another aspect, the invention provides a method of treating a subject in need thereof, comprising administering to the subject an effective amount of a pharmaceutical composition described herein to the subject.

In some embodiments, treating the subject in need thereof involves an agonist activity (e.g., a biased agonist activity), an inverse agonist activity, or an antagonist activity of PTHR signaling or a combination of the forgoing. In some embodiments, treating the subject in need thereof involves an agonist activity of PTHR signaling. In some embodiments, treating the subject in need thereof involves a biased agonist activity of PTHR signaling. In some embodiments, treating the subject in need thereof involves an inverse agonist activity of PTHR signaling. In some embodiments, treating the subject in need thereof involves an antagonist activity of PTHR signaling.

The term "subject" or "patient" refers to an animal (e.g., a mammal). In some embodiments, the subject is a mammal. In some embodiments, the subject is a human. In some embodiments, the subject is an adult. In some embodiments, the subject is at least 50 years old. In some embodiments, the subject is a female. In some embodiments, the subject is peri-menopausal, menopausal, or post-menopausal. In some embodiments, the subject is peri-menopausal. In some embodiments, the subject is menopausal. In some embodiments, the subject is post-menopausal.

A subject to be treated according to the methods described herein may be one who has been diagnosed with a condition, or one at risk of developing such conditions. In some embodiments, the subject has the condition. In some embodiments, the subject has been diagnosed with the condition. In other embodiments, the subject is at risk of developing the condition. Exemplary conditions (indications) treatable by the methods provided by the invention include those described in Tables 4-6 or claims, below, or the enumerated embodiments, supra.

TABLE 4

Non-limiting Examples of Disorders of Calcium Homeostasis Treatable with Agonist Activity or Biased Agonist Activity of PTHR Signaling.

| Indications | Populations | Clinical Manifestations | Diagnosis | Treatment Effects |
|---|---|---|---|---|
| Osteoporosis | Post-menopausal women, adults age 50 and older | Vertebral, hip, and distal radius fractures | 1) Fragility fracture, particularly at the spine, hip, wrist, humerus, rib and pelvis OR<br>2) T-score ≤ −2.5 standard deviations at any site based upon bone mineral density measurement by dual-energy x-ray absorptiometry OR<br>3) when the Fracture Risk Assessment Tool 10-year probability of major osteoporotic fracture is ≥20 percent or the 10-year probability of hip fracture is ≥3 percent | Bone mineral density stable or increased, fracture redaction |
| Hypoparathyroidism | Infant, adolescents, adults | 1) Acute manifestations: acute hypocalcemia and associated symptoms (e.g. mild or severe tetany, fatigue, hyperirritability, anxiety, and depression).<br>2) Chronic manifestations, such as muscle spasm, seizures, cataracts, osteoporosis, dental abnormalities, dry skin, hair loss | 1) Clinical examination of the symptoms,<br>2) Laboratory tests for persistent hypocalcemia (low serum calcium concentration) with a low or inappropriately normal serum PTH level and hyperphosphatemia (in the absence of hypomagnesemia) | Calcium homeostasis, amelioration of clinical manifestations |
| Blomstrand's chondrodysplasia | Neonates | Low birth weight, facial dysmorphism, very short limbs, short trunk, narrow thorax, tooth and mammary gland development defects, underdeveloped lungs, narrowing of the aorta, and bowel malrotation, typically fatal shortly after birth | 1) Genetic screening of PTHR,<br>2) Clinical and radiological characteristics which show generalized increase in bone density with advanced ossification, severe shortness of the long bones with wide metaphyses and club-shaped distal ends, long narrow thorax, calcified hyoid bone and laryngeal cartilage and underdeveloped viscerocranium, and<br>3) histopathological examination that shows acceleration of the endochondral ossification centers. | Amelioration of clinical manifestations and extending lifespan of affected newborns |
| Familial primary failure of eruption | Teenage age 15 or older | Incomplete tooth eruption resulting in a posterior unilateral/bilateral open bite | Clinical examination to rule out mechanical failure due to obstruction in the path of eruption, and genetic analysis of PTHR to confirm | Inducing tooth eruption |
| Eiken syndrome | Infant, adolescents, adults | 1) Multiple epiphyseal dysplasia with extremely retarded ossification,<br>2) Abnormal remodeling of the bones in hands and feet,<br>3) Abnormal persistence of the cartilage in the pelvis and mild growth retardation. | Clinical examination of the symptoms and genetic analysis of PTHR to confirm | Amelioration of clinical manifestations |
| Ollier disease | Infants, adolescents, adults | 1) Multiple bony swellings on a figure or a toe, an asymmetric shortening of an extremity with limping, skeletal deformities,<br>2) Enchondromas in bones of the limbs, tibia, femur, fibula, humerus, pelvis, skull, ribs, and vertebrae, or<br>3) Malignant transformation to chondrosarcomas, typically accompanied by pain, increasing size, and thinning of the cortical bone | 1) Clinical examination for disease symptoms using CT scans, MRIs, or X-rays, and<br>2) Biopsies of the enchondromas to look for features characteristic of tire disease | Reduction of pain caused by enchondromas, enabling normal gait walking |

TABLE 5

Non-limiting Examples of Disorders of Calcium Homeostasis Treatable with antagonist Activity of PTHR Signaling.

| Indications | Populations | Clinical Manifestations | Diagnosis | Treatment Effects |
|---|---|---|---|---|
| Hypercalcemia | Pediatric age group, cancer patients, women age 50 or older | 1) Moderately elevated serum calcium (12-14 mg/dL) may lead to polyuria, polydipsia, anorexia, nausea, and constipation,<br>2) Highly elevated serum calcium may lead to weakness, difficulty concentrating, confusion, stupor, and coma,<br>3) Chronic hypercalcemia associated with hypercalciuria can lead to kidney stones and nephrocalcinosis, | Blood tests for elevated level of serum calcium Specifically:<br>1) Mild: Total Ca 10.5-11.9 mg/dL (2.5-3 mmol/L) or Ionized Ca 5.6-8 mg/dL (1.4-2 mmol/L),<br>2) Moderate: Total Ca 12-13.9 mg/dL (3-3.5 mmol/L) or Ionized Ca S-10 mg/dL (2-2.5 mmol/L),<br>3) Hypercalcemic crisis: Total Ca 14-16 mg/dL (3.5-4 mmol/L) or Ionized Ca 10-12 mg/dL (2.5-3 mmol/L) | Calcium homeostasis, amelioration of clinical manifestations |

TABLE 5-continued

Non-limiting Examples of Disorders of Calcium Homeostasis Treatable with antagonist Activity of PTHR Signaling.

| Indications | Populations | Clinical Manifestations | Diagnosis | Treatment Effects |
|---|---|---|---|---|
| | | 4) Severe hypercalcemia can lead to cardiac arrhythmia, | | |
| | | 5) Poor prognosis when associated with malignancy | | |
| Hyperparathyroidism | Postmenopausal women, patients with prolonged & severe calcium or vitamin D deficiency, cancer patients undergone radiation treatment, lithium-treated patients | 1) Kidney stone and bone diseases (e.g. Osteitis fibrosa cystica). 2) Hypercalcemia, 3) Weakness and fatigue, 4) Neuropsychiatric disturbances, 5) Cardiovascular disease | Blood tests for elevated level of serum calcium and elevated or high-normal serum PTH. | Calcium homeostasis, normalized bone density level, amelioration of clinical manifestations |

TABLE 6

Non-limiting Examples of Disorders of Calcium Homeostasis Treatable with Inverse Agonist of PTHR Signaling

| Indications | Populations | Clinical Manifestations | Diagnosis | Treatment Effects |
|---|---|---|---|---|
| Jansen's metaphyseal chondrodysplasia | Infants, adolescents, adults | 1) Unusually short limbs, and stature, 2) Abnormal cartilage development and bone formation, 3) Diminished muscle mass and gradual swelling of joints, 4) Stiff and painful joints with restricted movements, 5) Sclerosis of cranial bones resulting in blindness and/or deafness, 6) Hypercalcemia | 1) Clinical examination for symptoms, 2) X-rays of the arms and legs for abnormal bone development, 3) Laboratory tests for elevated level of calcium in the urine and blood. | Serum calcium homeostasis, normalized activity of PTHR, amelioration of clinical |
| Hyperparathyroidism | | See Table 3 | See Table 3 | See Table 3 |
| Hypercalcemia | | See Table 3 | See Table 3 | See Table 3 |
| Hypercalciuria | Postmenopausal women, patients with kidney stones | 1) Hematuria, 2) Back or abdominal pain, 3) Voiding symptoms, 4) Kidney stones, 5) Repeated urinary tract infections | 1) Urine test for elevated calcium level (24-hour urinary calcium level of 250 mg or above), 2) Blood test to rule out diseases that may cause hypercalciuria, 3) Genetic testing if there is a family history of kidney stones, 4) Renal ultrasound for kidney abnormalities or stones | Urine calcium homeostasis, lowering risk of kidney stones |
| Nephrocalcinosis | Neonates with low birth weight, patients with hypercalcemia, hypercalciuria, hyperphosphaturia, hyperoxaluria | 1) Acute or chronic kidney injury, 2) Kidney stones and associated symptoms (e.g. hematuria, fever and chills, nausea and vomiting, severe back and abdominal pain), 3) chronic kidney failure | 1) Imaging tests (e.g. ultrasound, CT scan) for presence of calcium deposit in kidney, 2) Laboratory tests for elevated serum and urinary calcium levels and PTH levels | Urine calcium homeostasis, amelioration of clinical manifestations, lowering risk of end-stage renal disease |

In some embodiments, the subject has, or is at risk of developing, dysregulated calcium homeostasis.

In some embodiments, the subject has, or is at risk of developing, a disorder selected from Osteoporosis, Blomstrand's chondrodysplasia, Familial primary failure of tooth eruption, Eiken syndrome, Ollier disease, Hypercalcemia, Hyperparathyroidism, Jansen's metaphyseal chondrodysplasia, Hypercalcemia, Hypercalciuria, Nephrocalcinosis and combinations thereof.

In some embodiments, the subject has, or is at risk of developing, low bone density.

In some embodiments, the subject has, or is at risk of developing, a disorder selected from Blomstrand's lethal chondrodysplasia, Ollier disease, familial primary failure of tooth eruption, Eiken syndrome, brachydactyly type E, hypoparathyroidism, osteoporosis and combinations thereof.

In some embodiments, the subject has, or is at risk of developing, osteoporosis.

In some embodiments, the subject has, or is at increased risk of developing, a disorder selected from: hypercalcemia, hyperparathyroidism, parathyroid carcinoma, metastatic bone disease and combinations thereof. In some embodiments, the hyperparathyroidism occurs as a complication of parathyroid carcinoma. In some embodiments, the metastatic bone disease occurs with associated hypercalcemia.

In some embodiments, the subject has, or is at increased risk of developing, a disorder selected from Jansen's metaphyseal chondrodysplasia, hyperparathyroidism, hypercalcemia, hypercalciuria, nephrocalcinosis, chronic kidney disease and combinations thereof. In some embodiments, the chronic kidney disease occurs in conjunction with, or as a result of, hypercalcemia, hypercalciuria, nephrocalcinosis or a combination thereof.

Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

The sPTHs (and compositions, conjugates (e.g., comprising a heterologous moiety joined or otherwise lined, e.g., by covalent linkage), and fusion proteins containing them; or nucleic acids, vectors, or cells encoding them) provided by the invention can be used in a variety of situations to modulate PTHR signaling, e.g., as: an agonist of PTHR, a biased agonist of PTHR, an inverse agonist of PTHR, or an antagonist of PTHR. The modulation of PTHR signaling can be in vitro, in a cell, or in vivo, e.g., in a subject. Exemplary indications treatable by the methods provided by the invention include those described in Tables 2-4 or claims, below, or the enumerated embodiments, supra.

In these methods, the sPTH (composition, conjugate, fusion protein, or nucleic acid or cell) is provided to the subject by suitable means in an effective amount. The term "effective amount," "therapeutically effective amount," or "sufficient amount" refers to a quantity sufficient to, when administered to a subject, including a mammal (e.g., a human), effect beneficial or desired results, including effects at the cellular level, tissue level, or clinical results, and, as such, an "effective amount" or synonym thereto depends upon the context in which it is being applied. For example, in some embodiments it is an amount of the composition sufficient to achieve a treatment response as compared to the response obtained without administration of the composition. The amount of a given composition described herein that will correspond to such an amount will vary depending upon various factors, such as the given agent, the pharmaceutical formulation, the route of administration, the type of disease or disorder, the identity of the subject (e.g., age, sex, weight) or host being treated, and the like, but can nevertheless be routinely determined by one skilled in the art. Also, as used herein, a "therapeutically effective amount" of a composition of the present disclosure is an amount that results in a beneficial or desired result in a subject as compared to a control. As defined herein, a therapeutically effective amount of a composition of the present disclosure may be readily determined by one of ordinary skill by routine methods known in the art. Dosage regimen and route of administration may be adjusted to provide the optimum therapeutic response.

In some embodiments, the amount is effective to promote calcium homeostasis, increase, maintain or reduce a decrease of bone mineral density, reduce risk of fracture, promote fracture healing or a combination of the foregoing.

In some embodiments, the effective amount does not induce catabolic bone resorption.

"Treatment" and "treating," as used herein, refer to the medical management of a subject with the intent to improve, ameliorate, stabilize (i.e., not worsen), prevent or cure a disease, pathological condition, or disorder—such as the particular indications exemplified herein. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to minimizing or partially or completely inhibiting the development of the associated disease, pathological condition, or disorder); and supportive treatment (treatment employed to supplement another therapy). Treatment also includes diminishment of the extent of the disease or condition; preventing spread of the disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. "Treatment" can also mean prolonging survival as compared to expected survival if not receiving treatment. Those in need of treatment include those already with the condition or disorder, as well as those prone to have the condition or disorder or those in which the condition or disorder is to be prevented.

Features of the sPTHs provided by the invention (and conjugates, fusion proteins, and compositions containing them; or nucleic acids, vectors, or cells encoding them) or methods of using them can include one or more of the following enumerated embodiments.

Embodiment 1: a polypeptide that specifically binds Parathyroid Hormone Receptor (PTHR), wherein the polypeptide comprises a synthetic parathyroid hormone (sPTH).

Embodiment 2: the polypeptide of Embodiment 1, wherein the sPTH comprises a 14-amino acid sequence comprising:
  a) 1-3 polar residues and, relative to SEQ ID NO: 6, 1-14 amino acid substitutions;
  b) at least 4 polar residues, at least 1 charged residue, and, relative to SEQ ID NO: 7, 1-14 amino acid substitutions;
  c) at least 5 polar residues, at least 2 charged residues, and, relative to SEQ ID NO: 7, 1-14 amino acid substitutions;
  d) at least 5 polar residues, valine at position 2, and, relative to SEQ ID NO: 7, 1-13 amino acid substitutions; or
  e) at least 6 polar residues and, relative to SEQ ID NO: 7, 1-14 amino acid substitutions.

Embodiment 3: the polypeptide of Embodiment 1, wherein the sPTH comprises a 32-amino acid sequence comprising:
  a) at most 13 polar residues and, relative to SEQ ID NO: 8, 1-32 amino acid substitutions;
  b) at least 14 polar residues, valine at position 2, and, relative to SEQ ID NO: 8, 1-31 substitutions;
  c) at least 14 polar residues and, relative to SEQ ID NO: 8, 22-28 amino acid substitutions; or
  d) positions 1-14 of SEQ ID NO: 8 and, relative to SEQ ID NO: 5, 1-18 amino acid substitutions at positions 15-32.

Embodiment 4: the polypeptide of Embodiment 1, wherein the sPTH comprises an amino acid sequence having at least about 20% sequence identity to an amino acid sequence selected from SEQ ID NOs: 9-106 and SEQ ID NOs: 108-160.

Embodiment 5: the polypeptide of Embodiment 1, wherein the sPTH comprises an amino acid sequence having about 50-97% sequence identity to an amino acid sequence selected from SEQ ID NOs: 9-106 and SEQ ID NOs: 108-160.

Embodiment 6: the polypeptide of Embodiment 1, wherein the sPTH comprises at least 1 amino acid substitution relative to an amino acid sequence selected from SEQ ID NOs: 9-106 and SEQ ID NOs: 108-160.

Embodiment 7: the polypeptide of Embodiment 1, wherein the sPTH comprises up to 2-31 amino acid substitutions relative to an amino acid sequence selected from SEQ ID NOs: 9-106 and SEQ ID NOs: 108-160.

Embodiment 8: the polypeptide of Embodiment 1, wherein the sPTH comprises up to 2-18 amino acid substitutions relative to an amino acid sequence selected from SEQ ID NOs: 9-106 and SEQ ID NOs: 108-160.

Embodiment 9: the polypeptide of Embodiment 1, wherein the sPTH comprises an amino acid sequence selected from SEQ ID NOs: 9-106 and SEQ ID NOs: 108-160.

Embodiment 10: the polypeptide of Embodiment 1, wherein the sPTH comprises an amino acid sequence having at least about 20% sequence identity to an amino acid sequence selected from SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160.

Embodiment 11: the polypeptide of Embodiment 1, wherein the sPTH comprises an amino acid sequence having about 50-97% sequence identity to an amino acid sequence selected from SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160.

Embodiment 12: the polypeptide of Embodiment 1, wherein the sPTH comprises at least 1 amino acid substitution relative to an amino acid sequence selected from SEQ ID NOs: SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160.

Embodiment 13: the polypeptide of Embodiment 1, wherein the sPTH comprises up to 2-31 amino acid substitutions relative to an amino acid sequence selected from SEQ ID NOs: SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160.

Embodiment 14: the polypeptide of Embodiment 1, wherein the sPTH comprises up to 2-18 amino acid substitutions relative to an amino acid sequence selected from SEQ ID NOs: SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160.

Embodiment 15: the polypeptide of Embodiment 1, wherein the sPTH comprises an amino acid sequence selected from SEQ ID NOs: SEQ ID NOs: 9, 10, 19, 20, 31, 35, 41, 88, 101-103, 108, 115, 120, 121, 129, 131, 132, 134, 136-138, 140-143, 145, 147-152, 154, 155 and 157-160.

Embodiment 16: the polypeptide of Embodiment 1, wherein the sPTH consists of 28-36 amino acids.

Embodiment 17: the polypeptide of Embodiment 1, wherein the sPTH consists of 30-34 amino acids.

Embodiment 18: the polypeptide of Embodiment 1, wherein the sPTH consists of 32 amino acids.

Embodiment 19: the polypeptide of any one of Embodiments 16-18, wherein the sPTH comprises an amino acid sequence having at least about 20% sequence identity to SEQ ID NO: 5.

Embodiment 20: the polypeptide of Embodiment 19, wherein the sPTH comprises an amino acid sequence having about 50-97% sequence identity to SEQ ID NO: 5.

Embodiment 21: the polypeptide of Embodiment 19, wherein the sPTH comprises at least 1 amino acid substitution relative to SEQ ID NO: 5.

Embodiment 22: the polypeptide of Embodiment 19, wherein the sPTH comprises 2-18 amino acid substitutions relative to SEQ ID NO: 5.

Embodiment 23: the polypeptide of Embodiment 19, wherein the sPTH comprises an amino acid sequence set forth by SEQ ID NO: 6.

Embodiment 24: the polypeptide of Embodiment 23, wherein the amino acid sequence set forth by SEQ ID NO: 6 is at the N-terminus of the sPTH.

Embodiment 25: the polypeptide of Embodiment 19, wherein the sPTH comprises an amino acid sequence having at least about 55% sequence identity to a sequence selected from the group consisting of SEQ ID NOs: 102-106 and SEQ ID NOs: 132-155.

Embodiment 26: the polypeptide of Embodiment 19, wherein the sPTH comprises an amino acid sequence having about 75-97% sequence identity to a sequence selected from the group consisting of SEQ ID NOs: 102-106 and SEQ ID NOs: 132-155.

Embodiment 27: the polypeptide of Embodiment 1, wherein the sPTH comprises an amino acid sequence selected from the group consisting of SEQ ID NOs: 102-106 and SEQ ID NOs: 132-155.

Embodiment 28: the polypeptide of Embodiment 1, wherein the sPTH comprises the amino acid sequence of SEQ ID NO: 107.

Embodiment 29: the polypeptide of any one of Embodiments 6, 12 and 21, wherein the at least 1 amino acid substitution is a conservative substitution.

Embodiment 30: the polypeptide of Embodiment 29, wherein the at least 1 amino acid substitution is a highly conservative substitution.

Embodiment 31: the polypeptide of any one of Embodiments 2, 3, 7, 8, 13, 14 and 22, wherein the amino acid substitutions are conservative substitutions.

Embodiment 32: the polypeptide of Embodiment 31, wherein the amino acid substitutions are highly conservative substitutions.

Embodiment 33: the polypeptide of any one of Embodiments 1-32, wherein the sPTH binds PTHR with an affinity that is at least about 5% higher than a polypeptide having an amino acid sequence consisting of SEQ ID NO: 1, SEQ ID NO: 2, SEQ ID NO: 3, SEQ ID NO: 4 or SEQ ID NO: 5.

Embodiment 34: the polypeptide of any one of Embodiments 1-32, wherein the sPTH binds PTHR with an affinity that is at least about 5% lower than a polypeptide having an amino acid sequence consisting of SEQ ID NO: 1, SEQ ID NO: 2, SEQ ID NO: 3, SEQ ID NO: 4 or SEQ ID NO: 5.

Embodiment 35: the polypeptide of any one of Embodiments 1-32, wherein the sPTH binds PTHR with an affinity that is no more than about 5% lower than a polypeptide having an amino acid sequence consisting of SEQ ID NO: 1, SEQ ID NO: 2, SEQ ID NO: 3, SEQ ID NO: 4 or SEQ ID NO: 5.

Embodiment 36: the polypeptide of any one of Embodiments 1-35, wherein the sPTH is an agonist of PTHR.

Embodiment 37: the polypeptide of Embodiment 36, wherein the sPTH is a biased agonist of PTHR.

Embodiment 38: the polypeptide of any one of Embodiments 1-35, wherein the sPTH is an inverse agonist of PTHR.

Embodiment 39: the polypeptide of any one of Embodiments 1-35, wherein the sPTH is an antagonist of PTHR.

Embodiment 40: the polypeptide of any one of Embodiments 1-39, wherein the polypeptide is conjugated to a heterologous moiety.

Embodiment 41: the polypeptide of Embodiment 40, wherein the heterologous moiety is selected from the group consisting of polyethylene glycol (PEG), hexadecanoic acid, a hydrogel, a lipid nanoparticle, a polymer nanoparticle, and a heterologous polypeptide sequence, or a combination thereof.

Embodiment 42: the polypeptide of Embodiment 41, wherein the polymer nanoparticle comprises poly(lactic-co-glycolic) acid (PLGA).

Embodiment 43: the polypeptide of Embodiment 40, wherein the heterologous polypeptide sequence comprises a carrier polypeptide.

Embodiment 44: the polypeptide of Embodiment 43, wherein the carrier polypeptide is albumin or an Fc polypeptide.

Embodiment 45: a fusion protein comprising the polypeptide of any one of Embodiments 1-44.

Embodiment 46: a polynucleotide comprising a sequence encoding the polypeptide of any one of Embodiments 1-44 or the fusion protein of Embodiment 45.

Embodiment 47: an expression vector comprising the polynucleotide of Embodiment 46.

Embodiment 48: a host cell comprising the polynucleotide of Embodiment 46 or the expression vector of Embodiment 47.

Embodiment 49: a composition comprising the polypeptide of any one of Embodiments 1-44 or the fusion protein of Embodiment 45.

Embodiment 50: the composition of Embodiment 49, further comprising one or more pharmaceutical excipients, diluents, or carriers.

Embodiment 51: a method of modulating PTHR signaling in a mammalian cell, comprising contacting the mammalian cell with an effective amount of the composition of Embodiment 49 or 50.

Embodiment 52: a method of treating a subject in need thereof, comprising administering an effective amount of the composition of Embodiment 49 or 50 to the subject.

Embodiment 53: a method of modulating PTHR signaling in a subject in need thereof, comprising administering an effective amount of the composition of Embodiment 49 or 50 to the subject.

Embodiment 54: the method of Embodiment 52 or 53, wherein the subject is a mammal.

Embodiment 55: the method of Embodiment 54, wherein the subject is a human.

Embodiment 56: the method of any one of Embodiments 52-55, wherein the subject is an adult.

Embodiment 57: the method of any one of Embodiments 52-56, wherein the subject is at least 50 years old.

Embodiment 58: the method of any one of Embodiments 52-57, wherein the subject is a female.

Embodiment 59: the method of Embodiment 58, wherein the subject is peri-menopausal, menopausal, or post-menopausal.

Embodiment 60: the method of any one of Embodiments 52-59, wherein the subject has, or is at risk of developing, dysregulated calcium homeostasis.

Embodiment 61: the method of any one of Embodiments 52-59, wherein the subject has, or is at risk of developing, a disorder selected from Osteoporosis, Blomstrand's chondrodysplasia, Familial primary failure of tooth eruption, Eiken syndrome, Ollier disease, Hypercalcemia, Hyperparathyroidism, Jansen's metaphyseal chondrodysplasia, Hypercalcemia, Hypercalciuria, Nephrocalcinosis and combinations thereof.

Embodiment 62: the method of Embodiment 61, wherein the sPTH is an agonist of PTHR.

Embodiment 63: the method of Embodiment 62, wherein the sPTH is a biased agonist of PTHR.

Embodiment 64: the method of any one of Embodiments 52-63, wherein the subject has, or is at risk of developing, low bone density.

Embodiment 65: the method of any one of Embodiments 52-59, wherein the subject has, or is at risk of developing, a disorder selected from Blomstrand's lethal chondrodysplasia, Ollier disease, familial primary failure of tooth eruption, Eiken syndrome, brachydactyly type E, hypoparathyroidism, osteoporosis and combinations thereof.

Embodiment 66: the method of any one of Embodiments 52-59, wherein the subject has, or is at risk of developing, osteoporosis.

Embodiment 67: the method of any one of Embodiments 52-66, wherein the amount is effective to promote calcium homeostasis, increase, maintain or reduce a decrease of bone mineral density, reduce risk of fracture, promote fracture healing or a combination of the foregoing.

Embodiment 68: the method of any one of Embodiments 52-67, wherein the effective amount does not induce catabolic bone resorption.

Embodiment 69: the method of any one of Embodiments 52-59, wherein the subject has, or is at increased risk of developing, a disorder selected from: hypercalcemia, hyperparathyroidism, parathyroid carcinoma, metastatic bone disease and combinations thereof.

Embodiment 70: the method of Embodiment 69, wherein the hyperparathyroidism occurs as a complication of parathyroid carcinoma.

Embodiment 71: the method of Embodiment 69 or 70, wherein the metastatic bone disease occurs with associated hypercalcemia.

Embodiment 72: the method of any one of Embodiments 52-59, wherein the subject has, or is at increased risk of developing, a disorder selected from Jansen's metaphyseal chondrodysplasia, hyperparathyroidism, hypercalcemia, hypercalciuria, nephrocalcinosis, chronic kidney disease and combinations thereof.

Embodiment 73: the method of Embodiment 72, wherein the chronic kidney disease occurs in conjunction with, or as a result of, hypercalcemia, hypercalciuria, nephrocalcinosis or a combination thereof.

EXAMPLES

Sequences predicted to bind and activate PTHR were generated using computational models and solved structures of PTHR, including a recent CryoEM report published by Zhao L H et al., Science 364, 148-53 (2019). Sequences predicted to optimally bind to the receptor while retaining a similar structure to the native ligand. Families of sequences were generated as described in Table 2.

Example 1. Synthesis of Peptide

The peptide is produced using one of two methods known in the art: recombinant production from bacteria or chemical synthesis.

For recombinant production, the DNA sequences of the peptide is encoded in a suitable DNA vector for bacterial production, e.g. a PET vector. The bacteria are transformed with the plasmid and grown in suitable growth medium. When the bacteria have reached log growth stage the translation of the plasmid is induced, e.g. with IPTG. The protein is harvested from bacteria by lysis and recovery from inclusion bodies.

For solid phase chemical synthesis, standard methods are described in Stawikowski and Fields, *Curr Protoc Protein Sci* 2002, *February Chapter* 18.1, available at the following uniform resource locator: www.ncbi.nlm.nih.gov/pmc/articles/PMC3564544.

Example 2. Testing Receptor Activity In Vitro for Agonism, Antagonism, and Inverse Agonism For measuring PTHR activity, standard methods such as cAMP accumulation assays, e.g., as described in Hattersley G et al., *Endocrinology*, 157(1):141-49 (2016), are used. These assays are performed at room temperature on cells transfected with plasmid DNA encoding PTHR variants (sPTHRs) provided by the invention. Standard kits, e.g., cAMP-Glo™ assay by Promega, are used to measure cAMP levels in cells with a homogeneous, bioluminescent and high-throughput assay that monitors cAMP production (see, e.g., Kumar M et al., *Assay Drug Dev Technol.* 5(2): 237-45 (2007). The assay is based on the principle that cyclic AMP (cAMP) stimulates protein kinase A (PKA) holoenzyme activity, which in turn decreases available ATP, leading to decreased light production in a coupled luciferase reaction.

The assay is performed following manufacturer's protocols. Cells are treated with the peptide at various concentrations. Cells are then lysed with a lysis buffer. After adding a PKA reaction mix, the cell lysates are incubated for 20 minutes. Then a developing buffer containing the Kinase-Glo reagent is added and plates are incubated for 10 minutes. Finally, luminescence is measured using a plate-reading luminometer.

a) Agonist Activity

The produced peptide is tested for activation of the receptor in cell lines that recombinantly express PTHR as described in, for example, Gardella et al., *Endocrinology* 137(9): 3936-41 (1996). Briefly, COS-7 cells are cultured in DMEM supplemented with 10% FBS. Cells are transfected with DEAE/dextran and plasmid DNA (100 ng/well) encoding PTHR cDNA. Receptor assays are performed with intact COS-7 cells (500,000 cells/well) three days after transfection.

To test for agonist activity, cells are treated with the agonist peptide at various concentrations. PTHR activation is then measured using a cAMP accumulation assay (e.g. cAMP-Glo™ assay) as described herein. It is expected that activation of the PTHR by an agonist peptide leads to accumulation of cAMP inside the cell, which is reflected as a higher luminescence reading than in control or untreated cells.

b) Antagonist Activity

The produced peptide is tested for inhibition of receptor activation in cell lines that recombinantly express PTHR as described in the agonist activity section. To test for antagonist activity, cells are treated with the antagonist peptide at various concentrations together with a validated agonist at a fixed concentration (e.g. PTH 1-34) at 1 nM as described in Shimizu N et al., *J Biol Chem.* 280(3): 1797-807 (2005).

PTHR activity is then measured using a cAMP accumulation assay (e.g. cAMP-Glo™ assay) as described herein. Inhibition of PTHR activation by an antagonist peptide prevents the accumulation of cAMP inside the cell, which is reflected as a lower luminescence reading than in cells treated with a validated agonist.

c) Inverse Agonist Activity

The produced peptide is tested for reducing basal receptor activity in cell lines that recombinantly express a gain-of-function mutant of PTHR as described in, for example, Saito H et al., *J Clin Endocrinol Metab.* 103(7): 2660-69 (2018). Briefly, HEK293 cells are seeded in 96-well plates at a density of 20,000 cells/well and are cultured in DMEM supplemented with 10% FBS. Cells are transfected with DEAE/dextran and plasmid DNA (100 ng/well) encoding a gain-of-function mutant of PTHR (e.g. H223R). Receptor assays are performed with intact HEK293 cells (100,000 cells/well) two days after transfection.

Cells are treated with the inverse agonist peptide at various concentrations. Mutant PTHR activation is then measured using a cAMP accumulation assay (e.g. cAMP-Glo™ assay) as described herein. It is expected that a reduction in basal mutant PTHR activity leads to a decrease of cAMP inside the cell, which is reflected as a lower luminescence reading than in control or untreated cells.

Example 3. Testing Receptor Activity In Vitro for Biased Agonism

To test for biased β-arrestin signaling of PTHR, standard methods measuring β-arrestin recruitment are performed, e.g., as described in Wang T et al., Bethesda (Md.): Eli Lilly & Company and the National Center for Advancing Translational Sciences; 2004-2017 Nov. 20. Standard kits include, e.g. PathHunter β-arrestin assay by DiscoverX. A CHO cell line, stably expressing PTHR carboxyl-terminally extended with a peptide fragment of β-galactosidase and a corresponding deletion mutant of β-galactosidase fused to β-arrestin is used. The assay measures the level of reconstituted β-galactosidase with a homogeneous, bioluminescent, and high-throughput assay. The assay is based on the principle that β-arrestin recruitment brings about reconstitution of an active β-galactosidase, which catalyzes a bioluminescence reaction from an exogenous substrate to generate a bioluminescence readout.

The assay is performed following manufacturer's protocols. Cells are treated with the peptide at various concentrations. Cells are then incubated with the provided Working Detection Solution for 1 hour at room temperate in the dark. Finally, luminescence is measured using a plate-reading luminometer.

It is expected that an increase in β-arrestin recruitment to PTHR leads to an increase of reconstituted active β-galactosidase inside the cell, which is reflected as a higher luminescence reading than in control or untreated cells.

Example 4. Testing Activity In Vivo

The peptides are assessed for functional activity in the standard laboratory model of osteoporosis, namely the ovariectomized rat model. In this model, after surgical ovariectomy, bone resorption exceeds bone formation initially, causing bone loss. Soon thereafter, bone remodeling reaches a steady state, where resorption and formation are balanced. Statistically significant bone loss is seen in the proximal tibial metaphysis after 14 days, in the lumbar vertebral body after 60 days, and in the femoral neck after 30 days (see e.g., Lelovas et al., *Comp Med* 58(5): 424-30 (2008)).

Peptides are administered daily via subcutaneous injections to the laboratory rat (see e.g., Bernhardsson M et al., *Acta Orthop* 89(6): 674-77 (2018)). Bone density is measured non-invasively by densitometry and micro-computerized tomography (MicroCT), and invasively by histomorphometry and mechanical strength evaluation including three-point bending, four-point bending, and torsion testing.

It is expected that peptides that signal through PTHR (e.g., agonists or biased signaling agonists of PTHR) lead to less bone loss in the ovariectomized rat, thus increasing bone density and bone strength compared to untreated control animals.

Example 5. Treating a Human Patient with Osteoporosis

A patient is diagnosed as having or being at risk for osteoporosis, e.g. a postmenopausal woman aged 49 to 86 years with bone mineral density T score less than or equal to −2.5 and greater than −5.0 assessed by dual energy X-ray absorptiometry (see Miller P D et al., *JAMA* 316(7): 722-33 (2016)). The patient is prescribed treatment with the peptides described herein, e.g., an agonist of PTHR or biased signaling agonist of PTHR.

A method for administration of PTHR agonists and bone density assessment is described, for example, in Miller P D et al., *JAMA* 316(7): 722-33 (2016). The peptides are administered daily via subcutaneous injections, and the patient's bone mineral density is monitored by dual-energy X-ray absorptiometry.

Example 6. Bioluminescence Resonance Energy Transfer (BRET) Assays

Synthesis: Peptides were synthesized by Genscript using standard synthesis methods and purified using TFA. Peptides were shipped lyophilized and resuspend in DMSO prior to use.

a) Measuring β-Arrestin Recruitment

HEK293T cells (CRL-3216, ATCC, VA) at a density of 2 million/mL, were transfected with beta-arrestin1 or beta-arrestin2-Rluc cDNA (1 ng/well) (Life Technologies Corporation, CA) and Flag-PTHR1-YFP cDNA (199 ng/well) (Genwiz, New Jersey) using polyethylenimine (0.8 µL/well) (Polysciences, PA). 18-24 hours post transfection, the Luciferase substrate Coelenterazine (NanoLight Technologies, AZ) was added to cells, a baseline BRET measurement was taken after 5 minutes incubation, and then serial dilutions of peptides, diluted in PBS (with 0.5 mM $MgCl_2$+0.1% BSA FAF), were added to cells, and BRET signal was measured every 2 minutes for 30 minutes on Hybrid Multi-Mode Reader (Synergy Neo2, BioTek, VT). Seventy-five peptides were tested in the β-arrestin recruitment assay.

b) Measuring cAMP Accumulation

CHO-K1/Ga15/PTHR1 (Genscript USA, NJ) cells were cultured in a 10-cm Petri dish and harvested when cell culture confluence reached 80-85%. Cell suspension (5 µL) was seeded in 384-well plates at a density of 3,000 cells/well. Cells were treated with test samples (5 µL) or agonist (PTH 1-34) for 30 minutes at room temperature. cAMP-d2 working solution (5 µL) and anti-cAMP-Cryptate working solution (5 µL) were added to cells and incubated for 60 minutes at room temperature. The signal of the assay plate was read with PheraStar (BMG LABTECH, NC), an HTRF compatible reader.

c) Results

Figure 2:
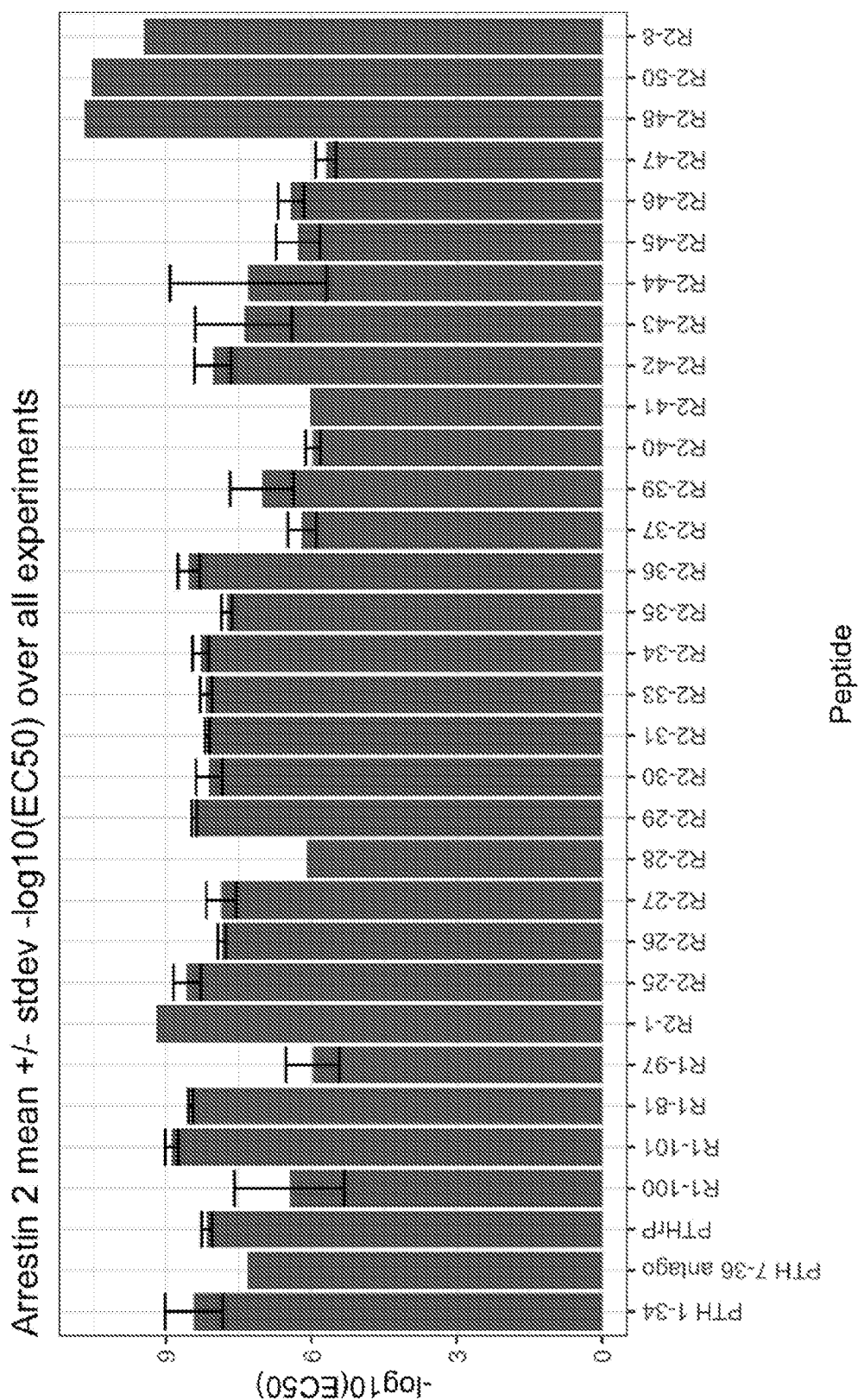
FIG. 2 depicts results of the β2-arrestin recruitment assay.

The β-arrestin recruitment and cAMP accumulation assays were performed on designed peptides to determine their ability to activate the PTHR receptor. PTH 1-34 was the positive control in both assays. In the β-arrestin1 recruitment assays, many generated peptides were able to elicit similar magnitudes of response as compared to PTH 1-34 (e.g., R1-101, R1-81, R2-13, R2-29 and R2-36), while two peptides demonstrated higher levels of recruitment of β-arrestin 1 (R2-38 and R2-52) (FIG. 1). Similarly, in the β-arrestin2 assay, many peptides demonstrated activity similar to the control peptide (e.g., R2-34, R2-33, R2-31, R2-30 and R2-42) while nine peptides showed increased activity as compared to control (R2-48, R2-50, R2-8, R2-1, R1-101, R2-25, R2-36, R1-81 and R2-29) (FIG. 2). In both B-arrestin assays there were also peptides that showed less activity than the control peptide.

Figure 3:
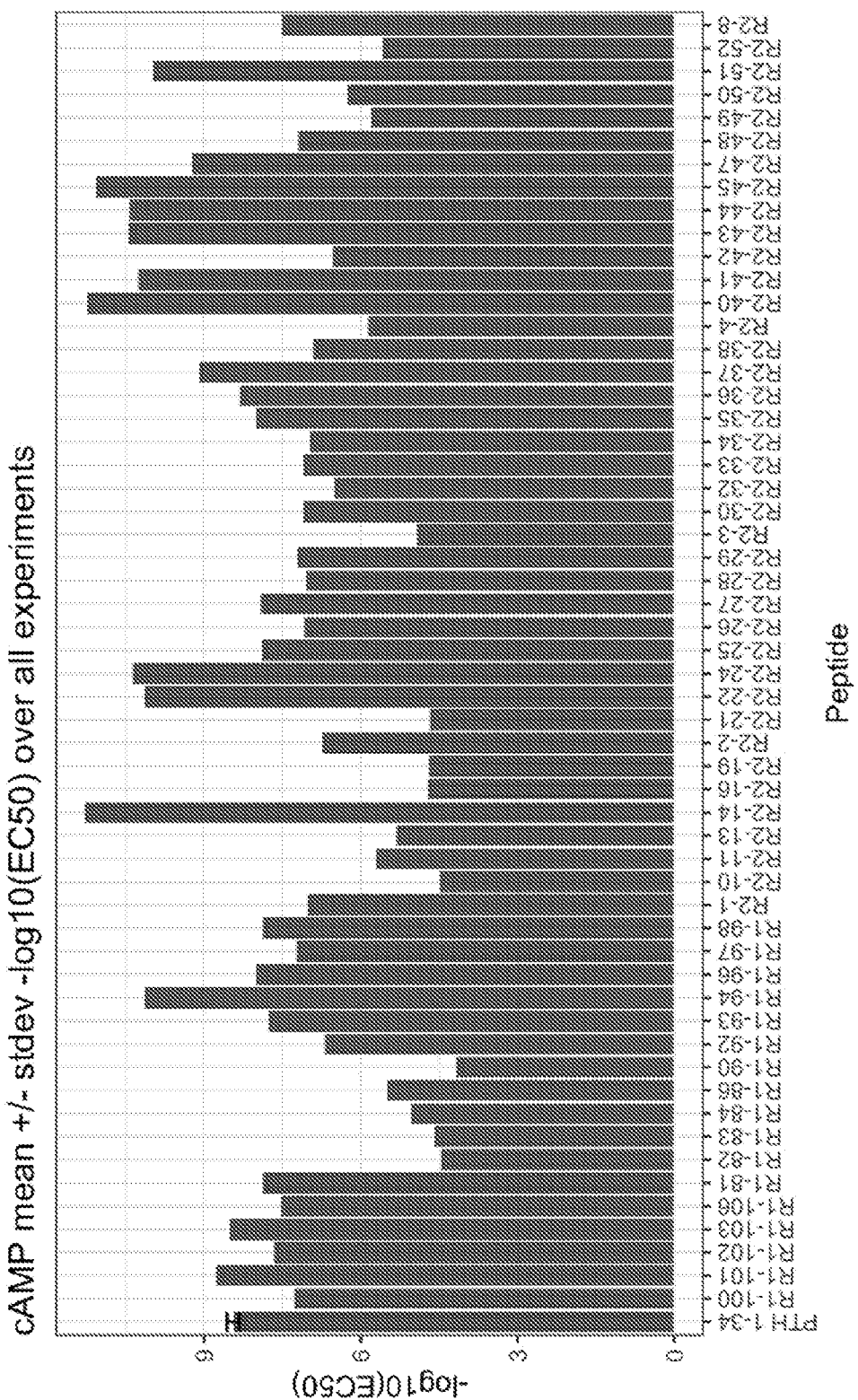
FIG. 3 depicts results of the cAMP accumulation assay.

Varying degrees of activity were also observed for the designed peptides in the cAMP accumulation assay. In this assay there were more peptides demonstrating increased activity as compared to the control peptide (R2-14, R2-40, R2-45, R2-43, R2-44, R2-24, R2-41, R2-22, R1-41, R1-94, R2-51, R2-47, R2-37, R1-101, and R1-103) whereas some peptides demonstrated activity similar to the control peptide (e.g., R2-36, R2-35, R1-96, R2-27 and R2-25) (FIG. 3).

For more details, see Tables 7 and 8.

TABLE 7

| Peptide | SEQ ID NO: | Amino Acid Sequence | β1-arrestin | β2-arrestin | cAMP |
|---|---|---|---|---|---|
| LA-PM-FL (R1-81) | 5 | AVAEIQLMHQRAKWIQDARRRAFLHKLIAEIH | + | ++ | |
| Teriparatide (R1-101) | 3 | SVSEIQLMHNLGKHLNSMERVEWLRKKLQDVHNF | + | ++ | ++ |
| R1-103 | 160 | AVSEHQLLHDKGKSIQDLRRRFFLHHLIAEIHTY | | | ++ |
| R1-94 | 101 | VDFEIQLMQQRAQWIADYRIREFLDKLIAEIF | | | ++ |
| R1-96 | 103 | AVAEIQLMHQRAKWRAEYELREMLLRLLEEIF | | | + |
| R2-1 | 108 | GVAELQLMHDLAKIRAEYELREMLLRLLEEIF | | ++ | |
| R2-8 | 115 | SVM MIQVMHDLAKIRAEYELREMLLRLLEEIF | | ++ | |
| R2-13 | 120 | GIAVITLMDLRAYLRAEYELREMLLRLLEEIF | + | | |
| R2-14 | 121 | GIAVLTILDLRAKLRAEYELREMLLRLLEEIF | | | ++ |

TABLE 7-continued

| Peptide | SEQ ID NO: Amino Acid Sequence | β1-ar-restin | β2-ar-restin | cAMP |
|---|---|---|---|---|
| R2-22 | 129 GIAVITIMIDYAKLRAEYELREMLLRLLEEIF | | | ++ |
| R2-24 | 131 GLAALTIGLLRAKLRAEYELREMLLRLLEEIF | | | ++ |
| R2-25 | 132 AVAEIQLMHQRAKWKLELELKVKLLEILKDVY | | ++ | + |
| R2-27 | 134 AVAEIQLMHQRAKWKLDLELAVSLRKILEDVY | | | + |
| R2-29 | 136 AVAEIQLMHQRAKWKLELELKEKIRKLLEDLL | + | ++ | |
| R2-30 | 137 AVAEIQLMHQRAKWLEELKLKDDLRKILEDVY | | + | |
| R2-31 | 138 AVAEIQLMHQRAKWGLDLELRARLREILRDVY | | + | |
| R2-33 | 140 AVAEIQLMHQRAKWLNELRLKEEMRKILEDVY | | + | |
| R2-34 | 141 AVAEIQLMHQRAKWRLEIELLKKLKEILKDVY | | + | |
| R2-35 | 142 AVAEIQLMHQRAKWGVELQLKVDLRRILEDVY | | | + |
| R2-36 | 143 AVAEIQLMHQRAKWKLELELKAFLDQILKDVL | + | ++ | + |
| R2-38 | 145 AVAEIQLMHQRAKWELLEELLKILLELLKEYI | ++ | | |
| R2-40 | 147 AVAEIQLMHQRAKWDLLIELVKLLHELLKEYI | | | ++ |
| R2-41 | 148 AVAEIQLMHQRAKWEIQEIGIKITLDLLQTLK | | | ++ |
| R2-42 | 149 AVAEIQLMHQRAKWAIQEIGIKITRELLERYL | | + | |
| R2-43 | 150 AVAEIQLMHQRAKWELQEIGIAITLRLLARYI | | | ++ |
| R2-44 | 151 AVAEIQLMHQRAKWSLREELEKLLKELLKEYI | | | ++ |
| R2-45 | 152 AVAEIQLMHQRAKWGLEIELLKLLLSLLKEYI | | | ++ |
| R2-47 | 154 AVAEIQLMHQRAKWDVLIELAKLLAELLRRYH | | | ++ |
| R2-48 | 155 AVAEIQLMHQRAKWKILEELLKILIDLLKQYI | | ++ | |
| R2-50 | 157 GVAMLQIMHDLAKIKQELELKDSMKKILEDVL | | ++ | |
| R2-51 | 158 GIAVITLMVLRALLELQEIGRKITLELLKEYI | | | ++ |
| R2-52 | 159 GIAVITLMLLRAYLELLEELVKILHELLRRYH | ++ | | |

++: affinity higher than PTH [1-34];
+: affinity similar to PTH [1-34]

TABLE 8

| Assay | Peptide | Plate | $-\log_{10}$Slope | $E_{min}$ | $E_{max}$ | $-\log_{10}EC_{50}$ | Residual |
|---|---|---|---|---|---|---|---|
| arrestin 1 | R1-101 | 25 | −3.66437 | 6.146394 | 7.287498 | −8.73365 | 0.122568 |
| arrestin 1 | PTH 7-36 antago | 25 | −1.19223 | 6.03964 | 7.67654 | −6.97839 | 0.128656 |
| arrestin 1 | R1-103 | 7 | −3.3831 | 5.862695 | 7.112258 | −8.02516 | 0.083962 |
| arrestin 1 | R1-81 | 1 | −2.98963 | 5.835818 | 7.256445 | −8.45166 | 0.032249 |
| arrestin 1 | R1-97 | 5 | −4.22141 | 5.951399 | 20.72174 | −6.02484 | 0.09249 |
| arrestin 1 | R1-100 | 7 | −4.48223 | 5.870708 | 20.479 | −6.24457 | 0.044356 |
| arrestin 1 | R2-8 | 9 | −2.33882 | 6.151146 | 6.286648 | −8.43199 | 0.129255 |
| arrestin 1 | R2-25 | 15 | −3.96501 | 6.222508 | 7.379416 | −8.58597 | 0.035326 |
| arrestin 1 | R2-26 | 17 | −2.29129 | 5.867202 | 7.106233 | −7.5663 | 0.103156 |
| arrestin 1 | R2-27 | 17 | −7.32252 | 5.954223 | 6.941242 | −7.92242 | 0.093795 |
| arrestin 1 | R2-29 | 17 | −5.78198 | 5.94738 | 7.259829 | −8.14727 | 0.095022 |
| arrestin 1 | R2-30 | 17 | −4.26657 | 6.00839 | 7.30644 | −7.87643 | 0.077453 |
| arrestin 1 | R2-31 | 17 | −2.89461 | 6.154237 | 7.691234 | −8.00193 | 0.128754 |
| arrestin 1 | R2-33 | 19 | −4.04829 | 6.001272 | 7.184427 | −7.98904 | 0.09142 |
| arrestin 1 | R2-34 | 19 | −3.22123 | 5.980063 | 7.29361 | −8.1847 | 0.044672 |
| arrestin 1 | R2-35 | 19 | −2.47268 | 6.006775 | 9.812916 | −6.5715 | 0.059416 |
| arrestin 1 | R2-36 | 19 | −3.42871 | 6.001678 | 7.329113 | −8.32788 | 0.082645 |
| arrestin 1 | R2-37 | 19 | −0.86782 | 6.043788 | 15.46311 | −3.59779 | 0.112591 |
| arrestin 1 | R2-39 | 21 | −4.06484 | 6.066979 | 20.8948 | −6.11091 | 0.094202 |
| arrestin 1 | R2-42 | 21 | −1.14937 | 6.035411 | 18.66846 | −4.98628 | 0.111677 |

TABLE 8-continued

| Assay | Peptide | Plate | $-\log_{10}$Slope | $E_{min}$ | $E_{max}$ | $-\log_{10}EC_{50}$ | Residual |
|---|---|---|---|---|---|---|---|
| arrestin 1 | R2-43 | 23 | −3.74142 | 5.979661 | 17.08711 | −6.29651 | 0.076966 |
| arrestin 1 | R2-44 | 23 | −2.34606 | 6.06031 | 7.078245 | −7.82264 | 0.07169 |
| arrestin 1 | R2-45 | 23 | −4.73899 | 6.001717 | 24.17762 | −6.32781 | 0.083147 |
| arrestin 1 | R2-46 | 23 | −2.78212 | 6.081972 | 11.14238 | −6.34931 | 0.10863 |
| arrestin 1 | R2-47 | 23 | −2.2235 | 6.098458 | 11.38479 | −6.1864 | 0.121883 |
| arrestin 2 | R1-101 | 26 | −3.40921 | 6.161704 | 7.70999 | −8.84972 | 0.113948 |
| arrestin 2 | PTH 7-36 antago | 26 | −2.64854 | 6.307495 | 8.043352 | −7.32902 | 0.133964 |
| arrestin 2 | R1-103 | 8 | −4.60854 | 6.220637 | 7.776424 | −8.1909 | 0.128221 |
| arrestin 2 | R1-81 | 2 | −3.44814 | 6.049215 | 7.587378 | −8.51727 | 0.079743 |
| arrestin 2 | R1-97 | 6 | −4.94634 | 6.14761 | 22.50952 | −6.19564 | 0.096254 |
| arrestin 2 | R1-100 | 8 | −1.65319 | 6.228363 | 20.33495 | −5.40724 | 0.095584 |
| arrestin 2 | R2-8 | 10 | 4.444637 | 6.155573 | 6.297383 | −9.45704 | 0.089667 |
| arrestin 2 | R2-25 | 16 | −3.2515 | 6.267908 | 7.976899 | −8.36678 | 0.105065 |
| arrestin 2 | R2-26 | 18 | −2.01872 | 6.011175 | 7.568688 | −7.79272 | 0.072225 |
| arrestin 2 | R2-27 | 18 | −1.82913 | 6.135618 | 7.958621 | −7.64516 | 0.060432 |
| arrestin 2 | R2-29 | 18 | −2.874 | 6.066658 | 7.584122 | −8.38807 | 0.074435 |
| arrestin 2 | R2-30 | 18 | −2.54333 | 6.058512 | 7.728025 | −7.91571 | 0.051285 |
| arrestin 2 | R2-31 | 18 | −2.40877 | 6.259213 | 7.819261 | −8.117 | 0.095013 |
| arrestin 2 | R2-33 | 20 | −8.42646 | 6.22444 | 7.470768 | −8.08651 | 0.076074 |
| arrestin 2 | R2-34 | 20 | −3.24875 | 6.179612 | 7.696937 | −8.09444 | 0.050482 |
| arrestin 2 | R2-35 | 20 | −4.07691 | 6.198627 | 7.43308 | −7.66956 | 0.09216 |
| arrestin 2 | R2-36 | 20 | −3.8162 | 6.18178 | 7.659017 | −8.26835 | 0.062633 |
| arrestin 2 | R2-37 | 20 | −4.37218 | 6.293192 | 22.39544 | −6.30391 | 0.101158 |
| arrestin 2 | R2-39 | 22 | −2.2339 | 6.073868 | 7.604875 | −6.95476 | 0.0878 |
| arrestin 2 | R2-42 | 22 | −2.91229 | 6.33522 | 7.757034 | −7.62613 | 0.172939 |
| arrestin 2 | R2-43 | 24 | −2.37934 | 6.089655 | 14.06431 | −6.23731 | 0.116676 |
| arrestin 2 | R2-44 | 24 | −9.38256 | 6.123667 | 7.375164 | −7.99475 | 0.127628 |
| arrestin 2 | R2-45 | 24 | −3.57379 | 6.026098 | 14.03428 | −6.47214 | 0.068764 |
| arrestin 2 | R2-46 | 24 | −2.30568 | 6.114641 | 11.79962 | −6.25957 | 0.098548 |
| arrestin 2 | R2-47 | 24 | −1.63411 | 6.024892 | 21.87281 | −5.45804 | 0.110933 |
| arrestin 1 | R1-101 | 25 | −1.35643 | 6.30183 | 8.153029 | −8.43065 | 0.117677 |
| arrestin 1 | R1-103 | 7 | −7.43631 | 6.190666 | 7.185963 | −7.97869 | 0.155138 |
| arrestin 1 | R1-81 | 1 | −2.57059 | 6.061215 | 7.166386 | −8.57738 | 0.093536 |
| arrestin 1 | R1-97 | 5 | −1.33638 | 6.101395 | 10.26443 | −5.38041 | 0.086938 |
| arrestin 1 | R1-97 | 25 | −0.04454 | 2.43567 | 10.33356 | −11.4538 | 0.141939 |
| arrestin 1 | R1-100 | 7 | −5.12856 | 6.019633 | 27.28658 | −6.21845 | 0.159241 |
| arrestin 1 | R2-2 | 7 | −3.86985 | −5.59146 | 6.25327 | −13.9804 | 0.113188 |
| arrestin 1 | R2-25 | 15 | −2.81906 | 6.18284 | 7.341335 | −8.26601 | 0.099156 |
| arrestin 1 | R2-26 | 17 | −7.46192 | 6.203562 | 7.274542 | −7.88795 | 0.080253 |
| arrestin 1 | R2-27 | 17 | −7.87662 | 6.339304 | 7.493003 | −8.02443 | 0.091344 |
| arrestin 1 | R2-28 | 17 | −1.45472 | 3.072172 | 6.353418 | −14.9851 | 0.072226 |
| arrestin 1 | R2-29 | 17 | −7.83286 | 6.275797 | 7.288178 | −8.77343 | 0.100462 |
| arrestin 1 | R2-30 | 17 | −2.2289 | 6.223949 | 7.393551 | −8.28318 | 0.072213 |
| arrestin 1 | R2-31 | 17 | −4.55902 | 6.311149 | 7.426912 | −8.52903 | 0.105397 |
| arrestin 1 | R2-33 | 19 | −4.07891 | 6.399071 | 7.363334 | −8.40065 | 0.120634 |
| arrestin 1 | R2-34 | 19 | −4.24999 | 6.335769 | 7.378634 | −8.48034 | 0.078121 |
| arrestin 1 | R2-35 | 19 | −2.43211 | 6.259793 | 7.41125 | −7.43571 | 0.094814 |
| arrestin 1 | R2-36 | 19 | −1.93146 | 6.331913 | 7.604401 | −8.53683 | 0.096724 |
| arrestin 1 | R2-37 | 19 | −5.35311 | 6.339286 | 19.22925 | −6.48074 | 0.142751 |
| arrestin 1 | R2-38 | 21 | −5.30726 | 6.18654 | 6.355126 | −10.7479 | 0.072391 |
| arrestin 1 | R2-39 | 21 | −4.87819 | 6.401256 | 34.55275 | −6.22625 | 0.103641 |
| arrestin 1 | R2-40 | 21 | −1.57662 | 6.300352 | 11.42645 | −5.44419 | 0.117583 |
| arrestin 1 | R2-41 | 21 | −8.21362 | 6.328476 | 6.435107 | −8.41681 | 0.077738 |
| arrestin 1 | R2-42 | 21 | −5.57419 | 6.400357 | 7.644406 | −7.96254 | 0.151995 |
| arrestin 1 | R2-43 | 23 | −1.60452 | 6.267439 | 7.669089 | −8.02701 | 0.131614 |
| arrestin 1 | R2-44 | 23 | −3.02674 | 6.364523 | 7.552742 | −8.55129 | 0.077691 |
| arrestin 1 | R2-45 | 23 | −2.6191 | 6.285601 | 12.85658 | −6.26609 | 0.111043 |
| arrestin 1 | R2-46 | 23 | −5.54145 | 6.401459 | 21.82825 | −6.40435 | 0.085923 |
| arrestin 1 | R2-47 | 23 | −1.64402 | 6.355807 | 17.90178 | −5.43901 | 0.108867 |
| arrestin 1 | R2-48 | 23 | −0.7628 | 3.554624 | 6.526038 | −15.4124 | 0.112866 |
| arrestin 1 | R2-50 | 25 | −4.76689 | −5.72967 | 6.470766 | −13.7741 | 0.079354 |
| arrestin 1 | R2-51 | 25 | −1.52367 | 6.301955 | 12.45775 | −4.53113 | 0.108253 |
| arrestin 1 | R2-52 | 25 | 2.31239 | 6.295406 | 6.365937 | −9.82536 | 0.075758 |
| arrestin 2 | R1-101 | 26 | −3.39569 | 6.380823 | 8.140141 | −8.76474 | 0.166718 |
| arrestin 2 | R1-103 | 8 | −9.21215 | 6.374395 | 7.868323 | −8.03579 | 0.091255 |
| arrestin 2 | R1-81 | 2 | −2.30687 | 6.085452 | 7.408443 | −8.51183 | 0.097487 |
| arrestin 2 | R1-97 | 6 | −1.28896 | 6.201675 | 10.85331 | −5.1583 | 0.123642 |
| arrestin 2 | R1-97 | 26 | −4.99533 | 6.487927 | 21.50397 | −6.36118 | 0.11987 |
| arrestin 2 | R1-100 | 8 | −5.80528 | 6.306403 | 6.949637 | −7.66565 | 0.079465 |
| arrestin 2 | R2-2 | 8 | −0.33983 | 6.419671 | 11.07618 | 5.097584 | 0.123907 |
| arrestin 2 | R2-25 | 16 | −2.75218 | 6.031105 | 7.180887 | −8.76132 | 0.156266 |
| arrestin 2 | R2-26 | 18 | −6.25653 | 6.304644 | 7.559174 | −7.90362 | 0.084314 |
| arrestin 2 | R2-27 | 18 | −3.20362 | 6.449705 | 7.979759 | −8.07977 | 0.089862 |
| arrestin 2 | R2-28 | 18 | −3.38076 | 6.411117 | 18.47556 | −6.09713 | 0.119486 |
| arrestin 2 | R2-29 | 18 | −3.05502 | 6.41841 | 7.905762 | −8.45704 | 0.090994 |
| arrestin 2 | R2-30 | 18 | −1.4524 | 6.270615 | 8.094622 | −8.29902 | 0.100309 |
| arrestin 2 | R2-31 | 18 | −3.97984 | 6.624255 | 8.044958 | −8.18192 | 0.16913 |
| arrestin 2 | R2-33 | 20 | −5.33147 | 6.520992 | 7.926627 | −8.11852 | 0.114488 |

TABLE 8-continued

| Assay | Peptide | Plate | $-\log_{10}$Slope | $E_{min}$ | $E_{max}$ | $-\log_{10}EC_{50}$ | Residual |
|---|---|---|---|---|---|---|---|
| arrestin 2 | R2-34 | 20 | −3.97155 | 6.578359 | 8.059432 | −8.34288 | 0.081623 |
| arrestin 2 | R2-35 | 20 | −3.62814 | 6.557147 | 7.892038 | −7.82049 | 0.104425 |
| arrestin 2 | R2-36 | 20 | −4.1664 | 6.569445 | 7.999631 | −8.60199 | 0.049635 |
| arrestin 2 | R2-37 | 20 | −4.14443 | 6.634685 | 17.04828 | −6.41288 | 0.172009 |
| arrestin 2 | R2-38 | 22 | −4.78929 | 20.52214 | 6.45397 | −14.0205 | 0.064539 |
| arrestin 2 | R2-39 | 22 | −5.31408 | 6.395877 | 29.12172 | −6.39712 | 0.097169 |
| arrestin 2 | R2-40 | 22 | −3.73317 | 6.379214 | 20.86439 | −6.06764 | 0.111524 |
| arrestin 2 | R2-41 | 22 | −4.33262 | 6.486465 | 23.7329 | −6.02679 | 0.091333 |
| arrestin 2 | R2-42 | 22 | −2.7849 | 6.525062 | 8.044761 | −8.09331 | 0.107996 |
| arrestin 2 | R2-43 | 24 | −6.42218 | 6.443462 | 7.570908 | −7.91094 | 0.10309 |
| arrestin 2 | R2-44 | 24 | −0.78896 | 6.494934 | 11.85153 | −5.45414 | 0.209544 |
| arrestin 2 | R2-45 | 24 | −2.78674 | 6.430457 | 10.65155 | −6.59307 | 0.094311 |
| arrestin 2 | R2-46 | 24 | −3.41329 | 6.479068 | 20.08088 | −6.26838 | 0.067343 |
| arrestin 2 | R2-47 | 24 | −2.07842 | 6.436063 | 19.21 | −5.86333 | 0.120444 |
| arrestin 2 | R2-48 | 24 | −8.23089 | 6.459772 | 6.670385 | −10.6746 | 0.125258 |
| arrestin 2 | R2-50 | 26 | −1.16928 | 5.187013 | 6.618338 | −13.8649 | 0.10237 |
| arrestin 2 | R2-51 | 26 | −5.93007 | −20.5641 | 6.470919 | −13.7546 | 0.123283 |
| arrestin 2 | R2-52 | 26 | −0.98752 | −1.15954 | 6.483885 | −17.4885 | 0.123745 |
| arrestin 1 | R1-101 | 15 | −2.90554 | 6.279055 | 7.563448 | −9.26116 | 0.090834 |
| arrestin 1 | R1-103 | 7 | −4.34263 | 6.353257 | 7.297271 | −8.038 | 0.109223 |
| arrestin 1 | R1-81 | 1 | −3.27131 | 6.112072 | 7.042697 | −8.75802 | 0.076918 |
| arrestin 1 | R1-97 | 5 | −0.04462 | 2.934771 | 9.906633 | −8.09513 | 0.141237 |
| arrestin 1 | R1-98 | 5 | 1.739528 | 1.022139 | 6.314393 | −4.859 | 0.081862 |
| arrestin 1 | R1-100 | 7 | −6.02332 | 6.170361 | 58.31206 | −6.21672 | 0.131635 |
| arrestin 1 | R2-1 | 7 | −0.14408 | 6.300882 | 6.353718 | −15.0294 | 0.141361 |
| arrestin 1 | R2-2 | 7 | −1.58621 | 6.145675 | 6.451231 | −12.1716 | 0.1147 |
| arrestin 1 | R2-13 | 15 | −3.16257 | 6.308513 | 6.38218 | −8.79414 | 0.058568 |
| arrestin 1 | R2-33 | 9 | −2.00656 | 6.081525 | 7.381088 | −8.23423 | 0.075354 |
| arrestin 1 | R2-34 | 9 | −3.25111 | 6.147686 | 7.285518 | −8.56132 | 0.150423 |
| arrestin 1 | R2-35 | 9 | −0.61564 | 5.968725 | 16.88254 | −3.52609 | 0.109478 |
| arrestin 1 | R2-36 | 9 | −5.88419 | 6.175407 | 7.401548 | −8.83234 | 0.073372 |
| arrestin 1 | R2-37 | 9 | −1.38612 | 6.25325 | 19.44443 | −5.07507 | 0.126006 |
| arrestin 1 | R2-39 | 11 | −0.28011 | 5.985472 | 15.40511 | 2.642922 | 0.088764 |
| arrestin 1 | R2-40 | 11 | −4.12541 | 6.188602 | 14.72289 | −6.24329 | 0.098952 |
| arrestin 1 | R2-42 | 11 | −1.50282 | 6.306221 | 7.865029 | −7.98377 | 0.061571 |
| arrestin 1 | R2-43 | 13 | −3.78637 | 6.2041 | 7.227838 | −8.30896 | 0.140154 |
| arrestin 1 | R2-44 | 13 | −3.27556 | 6.25581 | 7.406661 | −8.54124 | 0.111797 |
| arrestin 1 | R2-45 | 13 | −4.32814 | 6.247026 | 20.39585 | −6.31564 | 0.122074 |
| arrestin 1 | R2-46 | 13 | −3.506 | 6.209222 | 17.29816 | −6.24768 | 0.135081 |
| arrestin 1 | R2-47 | 13 | −1.83414 | 6.235331 | 15.73622 | −5.84346 | 0.076774 |
| arrestin 1 | R2-48 | 13 | −3.1505 | 6.298815 | 15.0613 | −5.72261 | 0.123223 |
| arrestin 1 | R2-50 | 15 | −3.90778 | 6.124526 | 32.90508 | −5.91917 | 0.154229 |
| arrestin 2 | R1-101 | 16 | −3.44041 | 6.416539 | 7.976446 | −9.02679 | 0.090755 |
| arrestin 2 | R1-103 | 8 | −2.48419 | 6.147466 | 7.780201 | −8.23942 | 0.091482 |
| arrestin 2 | R1-81 | 2 | −3.14015 | 6.335545 | 7.548369 | −8.4384 | 0.111906 |
| arrestin 2 | R1-97 | 6 | −4.85914 | 6.361686 | 26.9223 | −6.18587 | 0.074051 |
| arrestin 2 | R1-98 | 6 | −0.46508 | 6.276735 | 6.432724 | −13.3642 | 0.082743 |
| arrestin 2 | R1-100 | 8 | −5.84018 | 6.139939 | 39.04031 | −6.26849 | 0.106529 |
| arrestin 2 | R2-1 | 8 | −1.95354 | 6.238456 | 6.409413 | −9.20618 | 0.070808 |
| arrestin 2 | R2-2 | 8 | 2.527747 | 6.547328 | −2.79406 | −14.7615 | 0.166103 |
| arrestin 2 | R2-13 | 16 | −3.61873 | −2.4925 | 6.58784 | −14.0345 | 0.133576 |
| arrestin 2 | R2-33 | 10 | −2.16248 | 6.094935 | 7.526987 | −8.30658 | 0.114149 |
| arrestin 2 | R2-34 | 10 | −3.59082 | 6.203205 | 7.609874 | −8.4147 | 0.082833 |
| arrestin 2 | R2-35 | 10 | −0.89098 | 6.091675 | 35.8041 | −3.4639 | 0.105688 |
| arrestin 2 | R2-36 | 10 | −3.85048 | 6.157025 | 7.530131 | −8.70413 | 0.071546 |
| arrestin 2 | R2-37 | 10 | −2.11656 | 6.374294 | 17.00181 | −5.85944 | 0.145039 |
| arrestin 2 | R2-39 | 12 | −3.58018 | 6.100359 | 6.881588 | −7.70213 | 0.129432 |
| arrestin 2 | R2-40 | 12 | −2.82999 | 6.152649 | 13.88218 | −5.85178 | 0.067686 |
| arrestin 2 | R2-42 | 12 | −2.12175 | 6.235661 | 7.526825 | −8.37443 | 0.122709 |
| arrestin 2 | R2-43 | 14 | −8.22964 | 6.264873 | 7.448528 | −8.03404 | 0.064812 |
| arrestin 2 | R2-44 | 14 | −3.6425 | 6.337899 | 7.630814 | −8.45718 | 0.096291 |
| arrestin 2 | R2-45 | 14 | −1.76072 | 6.337035 | 16.06256 | −5.75663 | 0.084312 |
| arrestin 2 | R2-46 | 14 | −1.88157 | 6.242324 | 8.339645 | −6.72818 | 0.089595 |
| arrestin 2 | R2-47 | 14 | −1.71602 | 6.318784 | 15.15838 | −5.76622 | 0.070647 |
| arrestin 2 | R2-48 | 14 | −1.93949 | −4.57578 | 6.420842 | −15.1784 | 0.109984 |
| arrestin 2 | R2-50 | 16 | 10.25571 | 6.312181 | 6.445704 | −10.5168 | 0.118113 |
| cAMP | R1-101 | 1 | −4.49186 | 14.63557 | 99.36602 | −8.34985 | 12.24158 |
| cAMP | R2-1 | 1 | −5.89558 | 2.673345 | 102.1852 | −7.01875 | 14.71551 |
| cAMP | R2-10 | 1 | −8.78071 | 3.79518 | 1678.604 | −4.48793 | 8.082432 |
| cAMP | R2-11 | 1 | −11.3552 | 5.287236 | 60.79705 | −5.69704 | 11.35721 |
| cAMP | R2-12 | 1 | −2.72582 | 6.534209 | 153.679 | −3.86347 | 3.154672 |
| cAMP | R2-13 | 1 | −3.31195 | 7.259126 | 116.0137 | −5.3125 | 2.403771 |
| cAMP | R2-14 | 1 | 2.196012 | 8.540301 | 116.9051 | −11.2834 | 2.120625 |
| cAMP | R2-2 | 1 | −3.88938 | 4.632818 | 101.0674 | −6.728 | 7.984658 |
| cAMP | R2-3 | 1 | −8.5715 | 9.501501 | 259.6549 | −4.92824 | 15.493 |
| cAMP | R2-4 | 1 | −13.5432 | 2.654381 | 10.5534 | −5.86772 | 4.171461 |
| cAMP | R2-5 | 1 | −4.97227 | 4.829931 | 1578.863 | 5837.278 | 7.408966 |
| cAMP | R2-6 | 1 | −0.33409 | 0.032631 | 293.5761 | 3.87633 | 17.44833 |

TABLE 8-continued

| Assay | Peptide | Plate | $-\log_{10}$Slope | $E_{min}$ | $E_{max}$ | $-\log_{10}EC_{50}$ | Residual |
|---|---|---|---|---|---|---|---|
| cAMP | R2-7 | 1 | −0.95973 | 3.593562 | 822.5267 | −1.58323 | 4.045914 |
| cAMP | R2-8 | 1 | −24.9299 | 4.938274 | 19.89345 | −7.49657 | 17.2196 |
| cAMP | R2-9 | 1 | −0.02713 | −20.6663 | 664.6095 | 110.1556 | 9.11702 |
| cAMP | R1-101 | 2 | −5.1804 | 0.412936 | 99.40773 | −8.57049 | 2.357383 |
| cAMP | R2-16 | 2 | −8.30063 | −1.49195 | 48.72042 | −4.7084 | 1.636689 |
| cAMP | R2-17 | 2 | −2.07711 | −1.39859 | 39.69335 | −3.34914 | 1.871541 |
| cAMP | R2-18 | 2 | −1.18601 | −1.92578 | 36.61547 | −2.22611 | 2.735141 |
| cAMP | R2-19 | 2 | −5.2427 | −1.36012 | 323.9199 | −4.68868 | 2.604708 |
| cAMP | R2-21 | 2 | −8.12063 | −2.26162 | 46.96795 | −4.67336 | 1.510534 |
| cAMP | R2-22 | 2 | 7.16481 | −2.07417 | 17.59521 | −10.1491 | 1.250679 |
| cAMP | R2-24 | 2 | 5.587424 | −0.65372 | 81.36071 | −10.3729 | 2.115326 |
| cAMP | R2-25 | 2 | −10.1961 | 4.488444 | 95.98771 | −7.88919 | 7.687473 |
| cAMP | R2-26 | 2 | −14.6415 | 6.15594 | 96.79815 | −7.07339 | 11.23854 |
| cAMP | R2-27 | 2 | −4.34338 | 4.403704 | 93.3099 | −7.91328 | 19.23984 |
| cAMP | R2-28 | 2 | −5.51965 | 6.734959 | 99.16425 | −7.03446 | 10.41857 |
| cAMP | R2-29 | 2 | −16.1973 | 14.77215 | 97.50671 | −7.21884 | 15.21444 |
| cAMP | R2-30 | 2 | −18.1852 | 7.849948 | 97.18217 | −7.09678 | 12.77297 |
| cAMP | R2-31 | 2 | −0.697 | −1517.05 | 103.8608 | −14.0469 | 22.84342 |
| cAMP | R1-101 | 3 | −4.86397 | 9.728198 | 99.66045 | −8.49941 | 5.390328 |
| cAMP | R2-32 | 3 | −14.3219 | 2.1019 | 100.6009 | −6.50588 | 11.76834 |
| cAMP | R2-33 | 3 | −17.9495 | −0.26744 | 96.85082 | −7.09638 | 10.32183 |
| cAMP | R2-34 | 3 | −11.9049 | 2.454062 | 96.10208 | −6.97504 | 4.635947 |
| cAMP | R2-35 | 3 | −9.14214 | 5.464201 | 96.98397 | −8.0071 | 6.966845 |
| cAMP | R2-36 | 3 | −1.69594 | −10.5062 | 99.01174 | −8.32196 | 11.9955 |
| cAMP | R2-37 | 3 | −5.89877 | 5.495445 | 96.38356 | −9.08971 | 8.792597 |
| cAMP | R2-38 | 3 | −7.56562 | 19.45852 | 99.059 | −6.90556 | 17.62966 |
| cAMP | R2-40 | 3 | −2.20488 | −170.445 | 95.1155 | −11.2345 | 8.673476 |
| cAMP | R2-41 | 3 | −2.91072 | 10.03921 | 98.17581 | −10.2543 | 7.05364 |
| cAMP | R2-42 | 3 | 13.10915 | 96.01834 | 97.62262 | −6.545 | 1.343944 |
| cAMP | R2-43 | 3 | 7.668705 | 97.85763 | 309.3478 | −10.4589 | 1.217529 |
| cAMP | R2-44 | 3 | 0.471091 | 96.59975 | 106.448 | −10.4375 | 1.272862 |
| cAMP | R2-45 | 3 | 4.438451 | 98.51199 | 729.3803 | −11.0751 | 1.248351 |
| cAMP | R2-47 | 3 | 11.99833 | 99.34973 | 102.412 | −9.22839 | 1.457047 |
| cAMP | R1-101 | 4 | −4.04619 | −13.8414 | 98.43038 | −8.4994 | 4.79033 |
| cAMP | R1-81 | 4 | −5.22994 | −10.4872 | 94.99713 | −7.88122 | 3.751925 |
| cAMP | R1-82 | 4 | −5.76242 | −12.2505 | 51.44403 | −4.46215 | 1.670581 |
| cAMP | R1-83 | 4 | −6.26877 | −12.0945 | 47.24903 | −4.58837 | 2.197393 |
| cAMP | R1-84 | 4 | −3.62934 | −10.2488 | 125.0826 | −5.02659 | 3.013828 |
| cAMP | R1-86 | 4 | −9.53933 | −9.04434 | 25.1812 | −5.49161 | 6.480028 |
| cAMP | R1-87 | 4 | 0.135367 | −9.25783 | −8.03391 | 24.72815 | 4.425396 |
| cAMP | R1-89 | 4 | −0.01664 | −18.4361 | 0.600824 | −17.9653 | 3.07107 |
| cAMP | R1-90 | 4 | −5.75204 | −6.30637 | 2256.404 | −4.16597 | 9.253812 |
| cAMP | R2-48 | 4 | −14.2687 | 90.44764 | 98.79966 | −7.19393 | 4.66679 |
| cAMP | R2-49 | 4 | −5.63767 | −14.6476 | 99.94484 | −5.79156 | 4.933737 |
| cAMP | R2-50 | 4 | −8.41565 | −12.516 | 99.77448 | −6.24082 | 9.898114 |
| cAMP | R2-51 | 4 | 10.25862 | −13.5717 | 3.986571 | −9.97832 | 3.464232 |
| cAMP | R2-52 | 4 | −3.43672 | −14.1573 | 97.44394 | −5.58973 | 7.247991 |
| cAMP | R1-101 | 5 | −5.77746 | 0.48852 | 100.343 | −8.2859 | 4.973183 |
| cAMP | R1-100 | 5 | −12.0796 | 32.63055 | 99.91365 | −7.27705 | 12.21325 |
| cAMP | R1-101 | 5 | −5.02284 | 25.6401 | 97.78312 | −8.76364 | 7.085019 |
| cAMP | R1-102 | 5 | −14.6326 | 28.64947 | 94.786 | −7.66509 | 12.1767 |
| cAMP | R1-103 | 5 | −11.8012 | 47.93125 | 97.69201 | −8.51166 | 10.89905 |
| cAMP | R1-106 | 5 | −5.54744 | 61.43962 | 99.5463 | −7.52116 | 11.3453 |
| cAMP | R1-92 | 5 | −1.45894 | 61.45779 | 102.5804 | −6.69025 | 9.631564 |
| cAMP | R1-93 | 5 | −15.5187 | 41.08194 | 95.97063 | −7.76615 | 18.33612 |
| cAMP | R1-94 | 5 | −3.98103 | −112.04 | 90.81377 | −10.1329 | 16.93828 |
| cAMP | R1-96 | 5 | −3.35177 | 56.42437 | 99.68749 | −8.00625 | 16.05658 |
| cAMP | R1-97 | 5 | −14.176 | 53.99564 | 99.29501 | −7.23168 | 20.43195 |
| cAMP | R1-98 | 5 | −5.0512 | 51.11478 | 99.44218 | −7.87989 | 13.22805 |

It is expected that treatment with the peptides will lead to reduced bone density loss, reduced risk of fracture, and improvement of the patient's osteoporosis.

It should be understood that for all numerical bounds describing some parameter in this application, such as "about," "at least," "less than," and "more than," the description also necessarily encompasses any range bounded by the recited values. Accordingly, for example, the description "at least 1, 2, 3, 4, or 5" also describes, inter alia, the ranges 1-2, 1-3, 1-4, 1-5, 2-3, 2-4, 2-5, 3-4, 3-5, and 4-5, et cetera.

For all patents, applications, or other reference cited herein, such as non-patent literature and reference sequence information, it should be understood that they are incorporated by reference in their entirety for all purposes as well as for the proposition that is recited. Where any conflict exists between a document incorporated by reference and the present application, this application will control. All information associated with reference gene sequences disclosed in this application, such as GeneIDs or accession numbers (typically referencing NCBI accession numbers), including, for example, genomic loci, genomic sequences, functional annotations, allelic variants, and reference mRNA (including, e.g., exon boundaries or response elements) and protein sequences (such as conserved domain structures), as well as chemical references (e.g., PubChem compound, PubChem substance, or PubChem Bioassay entries, including the annotations therein, such as structures and assays, et cetera), are hereby incorporated by reference in their entirety.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g., elements, including numerical ranges and exemplary embodiments) of particular embodiments and aspects of the invention, including the working examples. For example, particular experimental parameters exemplified in the working examples can be adapted for use in the claimed invention piecemeal without departing from the invention. For example, for materials that are disclosed, while specific reference of each of the various individual and collective combinations and permutations of these compounds may not be explicitly disclosed, each is specifically contemplated and described herein. Thus, if a class of elements A, B, and C are disclosed as well as a class of elements D, E, and F and an example of a combination of elements A-D is disclosed, then, even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-groups of A-E, B-F, and C-E are specifically contemplated and should be considered disclosed from disclosure of A, B, and C; D, E, and F; and the example combination A-D. This concept applies to all aspects of this application, including elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art—thus, to the extent an element is described in one or more references known to the person having ordinary skill in the art, they may be excluded from the claimed invention by, inter alia, a negative proviso or disclaimer of the feature or combination of features.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A polypeptide that specifically binds Parathyroid Hormone Receptor (PTHR), wherein the polypeptide comprises a synthetic parathyroid hormone (sPTH), wherein the sPTH comprises an amino acid sequence selected from the group consisting of SEQ ID NOs: 102-106 and SEQ ID NOs: 132-155.

2. The polypeptide of claim 1, wherein the sPTH consists of 28-36 amino acids.

3. The polypeptide of claim 1, wherein the sPTH comprises the amino acid sequence of SEQ ID NO: 143.

4. The polypeptide of claim 1, wherein the sPTH binds PTHR with an affinity that is at least about 5% higher than a polypeptide having an amino acid sequence consisting of SEQ ID NO: 1, SEQ ID NO: 2, SEQ ID NO: 3, SEQ ID NO: 4 or SEQ ID NO: 5.

5. The polypeptide of claim 1, wherein the sPTH is an agonist of PTHR.

6. A fusion protein comprising the polypeptide of claim 1.

7. A polynucleotide comprising a sequence encoding the polypeptide of claim 1.

8. An expression vector comprising the polynucleotide of claim 7.

9. A host cell comprising the polynucleotide of claim 7.

10. A composition comprising the polypeptide of claim 1.

11. A method of modulating PTHR signaling in a mammalian cell, comprising contacting the mammalian cell with an effective amount of the composition of claim 10.

12. A method of treating osteoporosis a subject in need thereof, comprising administering an effective amount of the composition of claim 10 to the subject.

13. A method of modulating PTHR signaling in a subject in need thereof, comprising administering an effective amount of the composition of claim 10 to the subject, wherein the subject has osteoporosis.

* * * * *

```
                          SEQUENCE LISTING

<160> NUMBER OF SEQ ID NOS: 160

<210> SEQ ID NO 1
    <211> LENGTH: 84
    <212> TYPE: PRT
    <213> ORGANISM: Homo sapiens

<400> SEQUENCE: 1

Ser Val Ser Glu Ile Gln Leu Met His Asn Leu Gly Lys His Leu Asn
    1               5                   10                  15

Ser Met Glu Arg Val Glu Trp Leu Arg Lys Lys Leu Gln Asp Val His
                    20                  25                  30

Asn Phe Val Ala Leu Gly Ala Pro Leu Ala Pro Arg Asp Ala Gly Ser
                35                  40                  45

Gln Arg Pro Arg Lys Lys Glu Asp Asn Val Leu Val Glu Ser His Glu
            50                  55                  60

Lys Ser Leu Gly Glu Ala Asp Lys Ala Asp Val Asn Val Leu Thr Lys
    65                  70                  75                  80

Ala Lys Ser Gln

<210> SEQ ID NO 2
    <211> LENGTH: 141
    <212> TYPE: PRT
    <213> ORGANISM: Homo sapiens

<400> SEQUENCE: 2

Ala Val Ser Glu His Gln Leu Leu His Asp Lys Gly Lys Ser Ile Gln
    1               5                   10                  15

Asp Leu Arg Arg Arg Phe Phe Leu His His Leu Ile Ala Glu Ile His
                    20                  25                  30

Thr Ala Glu Ile Arg Ala Thr Ser Glu Val Ser Pro Asn Ser Lys Pro
                35                  40                  45

Ser Pro Asn Thr Lys Asn His Pro Val Arg Phe Gly Ser Asp Asp Glu
```

```
                50                  55                  60
Gly Arg Tyr Leu Thr Gln Glu Thr Asn Lys Val Glu Thr Tyr Lys Glu
 65                  70                  75                  80

Gln Pro Leu Lys Thr Pro Gly Lys Lys Lys Gly Lys Pro Gly Lys
                 85                  90                  95

Arg Lys Glu Gln Glu Lys Lys Lys Arg Arg Thr Arg Ser Ala Trp Leu
                100                 105                 110

Asp Ser Gly Val Thr Gly Ser Gly Leu Glu Gly Asp His Leu Ser Asp
                115                 120                 125

Thr Ser Thr Thr Ser Leu Glu Leu Asp Ser Arg Arg His
                130                 135                 140

<210> SEQ ID NO 3
<211> LENGTH: 34
<212> TYPE: PRT
<213> ORGANISM: Artificial Sequence
<220> FEATURE:
<223> OTHER INFORMATION: Teriparatide

<400> SEQUENCE: 3

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                20                  25                  30

Asn Phe

<210> SEQ ID NO 4
<211> LENGTH: 34
<212> TYPE: PRT
<213> ORGANISM: Artificial Sequence
<220> FEATURE:
<223> OTHER INFORMATION: Abaloparatide
<220> FEATURE:
<221> NAME/KEY: MISC_FEATURE
<222> LOCATION: (29)..(29)
<223> OTHER INFORMATION: aminoisobutyric acid

<400> SEQUENCE: 4

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Xaa Lys Leu His
                20                  25                  30

Thr Ala

<210> SEQ ID NO 5
<211> LENGTH: 32
<212> TYPE: PRT
<213> ORGANISM: Artificial Sequence
<220> FEATURE:
<223> OTHER INFORMATION: LA-PTH-FL

<400> SEQUENCE: 5

Ala Val Ala Glu Ile Gln Leu Met His Gln Arg Ala Lys Trp Ile Gln
 1               5                  10                  15

Asp Ala Arg Arg Arg Ala Phe Leu His Lys Leu Ile Ala Glu Ile His
                20                  25                  30

<210> SEQ ID NO 6
<211> LENGTH: 14
<212> TYPE: PRT
<213> ORGANISM: Artificial Sequence
<220> FEATURE:
```

<223> OTHER INFORMATION: LA-PTH

<400> SEQUENCE: 6

Ala Val Ala Glu Ile Gln Leu Met His Gln Arg Ala Lys Trp
1               5                   10

<210> SEQ ID NO 7
<211> LENGTH: 14
<212> TYPE: PRT
<213> ORGANISM: Artificial Sequence
<220> FEATURE:
<223> OTHER INFORMATION: 14-mer consensus
<220> FEATURE:
<221> NAME/KEY: MISC_FEATURE
<222> LOCATION: (1)..(1)
<223> OTHER INFORMATION: S or A
<220> FEATURE:
<221> NAME/KEY: MISC_FEATURE
<222> LOCATION: (1)..(1)
<220> FEATURE:
<221> NAME/KEY: MISC_FEATURE
<222> LOCATION: (3)..(3)
<223> OTHER INFORMATION: S or A
<220> FEATURE:
<221> NAME/KEY: MISC_FEATURE
<222> LOCATION: (5)..(5)
<223> OTHER INFORMATION: I or H
<220> FEATURE:
<221> NAME/KEY: MISC_FEATURE
<222> LOCATION: (8)..(8)
<223> OTHER INFORMATION: M or L
<220> FEATURE:
<221> NAME/KEY: MISC_FEATURE
<222> LOCATION: (10)..(10)
<223> OTHER INFORMATION: N, D, or Q
<220> FEATURE:
<221> NAME/KEY: MISC_FEATURE
<222> LOCATION: (11)..(11)
<223> OTHER INFORMATION: L, K, or R
<220> FEATURE:
<221> NAME/KEY: MISC_FEATURE
<222> LOCATION: (12)..(12)
<223> OTHER INFORMATION: G or A
<220> FEATURE:
<221> NAME/KEY: MISC_FEATURE
<222> LOCATION: (14)..(14)
<223> OTHER INFORMATION: H, S, or W

<400> SEQUENCE: 7

Xaa Val Xaa Glu Xaa Gln Leu Xaa His Xaa Xaa Xaa Lys Xaa
1               5                   10

<210> SEQ ID NO 8
<211> LENGTH: 32
<212> TYPE: PRT
<213> ORGANISM: Artificial Sequence
<220> FEATURE:
<223> OTHER INFORMATION: 32-mer consensus
<220> FEATURE:
<221> NAME/KEY: MISC_FEATURE
<222> LOCATION: (1)..(1)
<223> OTHER INFORMATION: S or A
<220> FEATURE:
<221> NAME/KEY: MISC_FEATURE
<222> LOCATION: (3)..(3)
<223> OTHER INFORMATION: S or A
<220> FEATURE:
<221> NAME/KEY: MISC_FEATURE
<222> LOCATION: (5)..(3)
<223> OTHER INFORMATION: I or H
<220> FEATURE:
<221> NAME/KEY: misc_feature
<222> LOCATION: (5)..(5)
<223> OTHER INFORMATION: Xaa can be any naturally occurring amino acid
<220> FEATURE:

-continued

```
<221> NAME/KEY: MISC_FEATURE
<222> LOCATION: (8)..(8)
<223> OTHER INFORMATION: M or L
<220> FEATURE:
<221> NAME/KEY: MISC_FEATURE
<222> LOCATION: (10)..(10)
<223> OTHER INFORMATION: N, D, or Q
<220> FEATURE:
<221> NAME/KEY: MISC_FEATURE
<222> LOCATION: (11)..(11)
<223> OTHER INFORMATION: L, K, or R
<220> FEATURE:
<221> NAME/KEY: MISC_FEATURE
<222> LOCATION: (12)..(12)
<223> OTHER INFORMATION: G or A
<220> FEATURE:
<221> NAME/KEY: MISC_FEATURE
<222> LOCATION: (14)..(14)
<223> OTHER INFORMATION: H, S, or W
<220> FEATURE:
<221> NAME/KEY: MISC_FEATURE
<222> LOCATION: (15)..(15)
<223> OTHER INFORMATION: L or I
<220> FEATURE:
<221> NAME/KEY: MISC_FEATURE
<222> LOCATION: (16)..(16)
<223> OTHER INFORMATION: N or Q
<220> FEATURE:
<221> NAME/KEY: MISC_FEATURE
<222> LOCATION: (17)..(17)
<223> OTHER INFORMATION: S or D
<220> FEATURE:
<221> NAME/KEY: MISC_FEATURE
<222> LOCATION: (18)..(18)
<223> OTHER INFORMATION: M, L, or A
<220> FEATURE:
<221> NAME/KEY: MISC_FEATURE
<222> LOCATION: (19)..(19)
<223> OTHER INFORMATION: E or R
<220> FEATURE:
<221> NAME/KEY: MISC_FEATURE
<222> LOCATION: (21)..(21)
<223> OTHER INFORMATION: V or R
<220> FEATURE:
<221> NAME/KEY: MISC_FEATURE
<222> LOCATION: (22)..(22)
<223> OTHER INFORMATION: E, F, or A
<220> FEATURE:
<221> NAME/KEY: MISC_FEATURE
<222> LOCATION: (23)..(23)
<223> OTHER INFORMATION: W, F, or L
<220> FEATURE:
<221> NAME/KEY: MISC_FEATURE
<222> LOCATION: (25)..(25)
<223> OTHER INFORMATION: R, H, or E
<220> FEATURE:
<221> NAME/KEY: MISC_FEATURE
<222> LOCATION: (26)..(26)
<223> OTHER INFORMATION: K or H
<220> FEATURE:
<221> NAME/KEY: MISC_FEATURE
<222> LOCATION: (27)..(27)
<223> OTHER INFORMATION: K or L
<220> FEATURE:
<221> NAME/KEY: MISC_FEATURE
<222> LOCATION: (28)..(28)
<223> OTHER INFORMATION: L or I
<220> FEATURE:
<221> NAME/KEY: MISC_FEATURE
<222> LOCATION: (29)..(29)
<223> OTHER INFORMATION: Q, A, or aminoisobutyric acid
<220> FEATURE:
<221> NAME/KEY: MISC_FEATURE
<222> LOCATION: (30)..(30)
<223> OTHER INFORMATION: D, E, or K
<220> FEATURE:
<221> NAME/KEY: MISC_FEATURE
<222> LOCATION: (31)..(31)
<223> OTHER INFORMATION: V, I, or L
```

```
<400> SEQUENCE: 8

Xaa Val Xaa Glu Xaa Gln Leu Xaa His Xaa Xaa Xaa Lys Xaa Xaa Xaa
1               5                   10                  15

Xaa Xaa Xaa Arg Xaa Xaa Xaa Leu Xaa Xaa Xaa Xaa Xaa Xaa His
            20                  25                  30

<210> SEQ ID NO 9
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 9

Val Asp Phe Glu Leu Trp Leu Leu Gln Phe Phe Leu Leu Phe
1               5                   10

<210> SEQ ID NO 10
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 10

Val Asp Phe Glu Leu Phe Leu Leu Gln Gln Phe Leu Leu Phe
1               5                   10

<210> SEQ ID NO 11
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 11

Val Asn Val Phe Leu Ala Leu Leu Gln His Phe Leu Glu Trp
1               5                   10

<210> SEQ ID NO 12
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 12

Ile Asn Pro Glu Leu Ala Ala Leu Gln Phe Phe Trp Gln Leu
1               5                   10

<210> SEQ ID NO 13
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 13

Val Asn Pro Glu Leu Ala Trp Leu Gln Phe Leu His Leu Leu
1               5                   10

<210> SEQ ID NO 14
<211> LENGTH: 14
<212> TYPE: PRT
<213> ORGANISM: Artificial Sequence
```

```
<220> FEATURE:
<223> OTHER INFORMATION: synthetic parathyroid hormone polypeptide

<400> SEQUENCE: 14

Ile Asn Tyr Glu Leu Met Thr Leu Thr Met Leu Leu Ile Trp
1               5                   10

<210> SEQ ID NO 15
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 15

Glu Asp Phe Glu Leu Trp Leu Leu Arg Phe Phe Trp Leu Leu
1               5                   10

<210> SEQ ID NO 16
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 16

Ile Asn Val Glu Leu Ala Ile Leu Glu Phe Phe Leu Gln Phe
1               5                   10

<210> SEQ ID NO 17
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 17

Ile Asn Phe Glu Leu Met Thr Leu Trp Phe Leu His Leu Leu
1               5                   10

<210> SEQ ID NO 18
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 18

Thr Asp Pro Met Leu Ala Ala Leu Gln Phe Phe Ala Gln Leu
1               5                   10

<210> SEQ ID NO 19
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 19

Ala Val Phe Glu Leu Trp Leu Leu Gln His Phe His Glu Trp
1               5                   10

<210> SEQ ID NO 20
<211> LENGTH: 14
<212> TYPE: PRT
<213> ORGANISM: Artificial Sequence
<220> FEATURE:
```

<223> OTHER INFORMATION: synthetic parathyroid hormone polypeptide

<400> SEQUENCE: 20

Val Asp Tyr Glu Leu Met Thr Leu Gln Gln Leu Leu Leu Phe
1               5                   10

<210> SEQ ID NO 21
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 21

Thr Asp Val Glu Leu Ala Val Leu Thr Phe Leu His Leu Phe
1               5                   10

<210> SEQ ID NO 22
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 22

Ile Asp Trp Glu Leu Met Phe Leu Gln Gln Leu His Leu Phe
1               5                   10

<210> SEQ ID NO 23
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 23

Thr Asn Tyr Glu Leu Ala Ile Leu Gln Phe Phe Trp Glu Phe
1               5                   10

<210> SEQ ID NO 24
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 24

Thr Asp Pro Glu Leu Ala Ala Leu Gln Met Phe Trp Thr Trp
1               5                   10

<210> SEQ ID NO 25
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 25

Thr Asn Val Phe Leu Ala Leu Leu Gln His Phe Trp Glu Trp
1               5                   10

<210> SEQ ID NO 26
<211> LENGTH: 14
<212> TYPE: PRT
<213> ORGANISM: Artificial Sequence
<220> FEATURE:
<223> OTHER INFORMATION: synthetic parathyroid hormone polypeptide

```
<400> SEQUENCE: 26

Val Asp Tyr Glu Leu Met Ile Leu Gln Phe Phe Thr Ser Leu
1               5                   10

<210> SEQ ID NO 27
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 27

Ile Asn Trp Glu Leu Met Thr Leu Thr Met Phe His Leu Trp
1               5                   10

<210> SEQ ID NO 28
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 28

Ile Asp Tyr Glu Leu Met Leu Leu Thr Phe Phe Thr Ser Phe
1               5                   10

<210> SEQ ID NO 29
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 29

Ile Asp Tyr Glu Leu Met Thr Leu Thr Phe Met Thr Ile Leu
1               5                   10

<210> SEQ ID NO 30
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 30

Thr Asp Val Glu Leu Ala Val Leu Glu Phe Phe Trp Gln Phe
1               5                   10

<210> SEQ ID NO 31
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 31

Thr Val Val Glu Leu Ala Thr Leu Gln Gln Leu Leu Leu Phe
1               5                   10

<210> SEQ ID NO 32
<211> LENGTH: 14
<212> TYPE: PRT
<213> ORGANISM: Artificial Sequence
<220> FEATURE:
<223> OTHER INFORMATION: synthetic parathyroid hormone polypeptide
```

```
<400> SEQUENCE: 32

Arg Val Val Glu Leu Glu Ile Leu Gln Gln Phe Leu Leu Phe
1               5                   10

<210> SEQ ID NO 33
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 33

Arg Val Pro Glu Ile Glu Ala Leu Gln Gln Leu Leu Leu Phe
1               5                   10

<210> SEQ ID NO 34
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 34

Thr Val Val Glu Leu Ala Thr Leu Gln His Phe Trp Leu Trp
1               5                   10

<210> SEQ ID NO 35
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 35

Thr Asp Phe Glu Leu Ala Leu Leu Gln His Phe Ala Gln Trp
1               5                   10

<210> SEQ ID NO 36
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 36

Arg Asp Ile Glu Leu Glu Ile Leu Glu Gln Phe Ala Leu Trp
1               5                   10

<210> SEQ ID NO 37
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 37

Glu Asn Phe Glu Leu Asn Leu Leu Arg Phe Phe Ala Gln Trp
1               5                   10

<210> SEQ ID NO 38
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 38
```

```
Val Asn Phe Glu Leu Phe Leu Leu Gln Gln Arg Trp Thr Phe
1               5                   10

<210> SEQ ID NO 39
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 39

Ile Asp Phe Glu Leu Trp Leu Leu Thr Gln Thr Ala Asp Phe
1               5                   10

<210> SEQ ID NO 40
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 40

Val Asp Phe Glu Leu Trp Leu Leu Ser Gln Leu His Ser Trp
1               5                   10

<210> SEQ ID NO 41
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 41

Val Asp Phe Glu Leu Phe Leu Leu Gln Gln Thr Ala Gln Trp
1               5                   10

<210> SEQ ID NO 42
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 42

Glu Asn Phe Glu Ile Trp Leu Leu Gln His Phe Ala Glu Trp
1               5                   10

<210> SEQ ID NO 43
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 43

Arg Asn Val Phe Ile Glu Leu Leu Gln Gln Thr Ala Leu Trp
1               5                   10

<210> SEQ ID NO 44
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 44
```

Thr Asn Phe Glu Leu Gln Leu Ile Gln Gln Leu Tyr Leu Trp
1               5                   10

<210> SEQ ID NO 45
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 45

Thr Asn Phe Glu Ile Ala Leu Met Gln His Phe Leu Glu Trp
1               5                   10

<210> SEQ ID NO 46
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 46

Val Asp Phe Glu Ile Phe Leu Leu Gln Gln Gln Ala Leu Ser
1               5                   10

<210> SEQ ID NO 47
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 47

Val Asp Phe Glu Leu Gln Leu Leu Gln Gln Thr Ala Leu Trp
1               5                   10

<210> SEQ ID NO 48
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 48

Met Asn Val Glu Ile Gln Leu Leu Gln Asp Phe Ala Gln Trp
1               5                   10

<210> SEQ ID NO 49
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 49

Arg Pro Val Glu Leu Glu Leu Leu Glu Gln Arg Ala Leu Trp
1               5                   10

<210> SEQ ID NO 50
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 50

Glu Asn Ile Glu Ile Tyr Leu Leu Gln Gln Leu Ala Gln Trp

<210> SEQ ID NO 51
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 51

```
Leu Pro Val Glu Ile Thr Leu Leu Gln Gln Thr Ala Gln Trp
1               5                   10
```

<210> SEQ ID NO 52
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 52

```
Val Asn Phe Glu Ile Phe Leu Val Gln Gln Thr Ala Thr Trp
1               5                   10
```

<210> SEQ ID NO 53
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 53

```
Thr Asp Phe Glu Ile Gln Leu Leu Gln Gln Phe Ala Leu Trp
1               5                   10
```

<210> SEQ ID NO 54
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 54

```
Val Asn Trp Glu Ile Gln Leu Met Gln Gln Val Leu Gln Trp
1               5                   10
```

<210> SEQ ID NO 55
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 55

```
Val Pro Phe Glu Leu Gln Leu Ser Thr Gln Arg Ala Leu Trp
1               5                   10
```

<210> SEQ ID NO 56
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 56

```
Thr Asn Tyr Glu Ile Gln Leu Val Trp Gln Thr Ala Leu Trp
1               5                   10
```

<210> SEQ ID NO 57
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 57

Thr Asn Trp Glu Ile Tyr Leu Met Gln Gln Ser Ala Leu Trp
1               5                   10

<210> SEQ ID NO 58
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 58

Met Pro Tyr Glu Ile Gln Leu Ile Gln Gln Thr Ala Gln Trp
1               5                   10

<210> SEQ ID NO 59
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 59

Val Asp Phe Glu Ile Gln Leu Leu Gln Gln Arg Ala Leu Trp
1               5                   10

<210> SEQ ID NO 60
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 60

Ile Asp Tyr Glu Ile Tyr Leu Ser His Gln Arg Ala Leu Trp
1               5                   10

<210> SEQ ID NO 61
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 61

Met Pro Tyr Glu Ile Gln Leu Met Ser Gln Thr Ala Asp Trp
1               5                   10

<210> SEQ ID NO 62
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 62

Val His Leu Glu Ile Gln Leu Met Gln Gln Ser Ala Leu Trp
1               5                   10

<210> SEQ ID NO 63
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 63

Thr Asn Tyr Glu Ile Gln Leu Ile Leu Gln Arg Ala Ile Trp
1               5                   10

<210> SEQ ID NO 64
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 64

Met Asn Tyr Glu Ile Ser Leu Met Arg Gln Arg Ala Leu Trp
1               5                   10

<210> SEQ ID NO 65
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 65

Val Asp Phe Glu Ile Gln Leu Met Gln Gln Arg Ala Leu Trp
1               5                   10

<210> SEQ ID NO 66
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 66

Leu Pro Leu Glu Ile Thr Leu Leu His Gln Arg Ala Lys Trp
1               5                   10

<210> SEQ ID NO 67
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 67

Lys His Trp Glu Ile Gln Leu Met Gln Gln Arg Ala Ala Trp
1               5                   10

<210> SEQ ID NO 68
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 68

Arg His Ile Glu Ile Trp Leu Met His Gln Arg Ala Leu Trp
1               5                   10

```
<210> SEQ ID NO 69
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 69

Met Pro Trp Glu Ile Gln Leu Met Ser Gln Gln Ala Lys Trp
1               5                   10

<210> SEQ ID NO 70
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 70

Met Pro Ala Glu Ile Gln Leu Ile Ser Gln Arg Ala Asp Trp
1               5                   10

<210> SEQ ID NO 71
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 71

Val Asp Phe Glu Ile Gln Leu Met His Gln Arg Ala Leu Trp
1               5                   10

<210> SEQ ID NO 72
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 72

Met Pro Ala Glu Ile Arg Leu Met His Glu Arg Ala Lys Trp
1               5                   10

<210> SEQ ID NO 73
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 73

Arg Val Ala Glu Ile Gln Leu Met Glu Gln Gln Ala Leu Trp
1               5                   10

<210> SEQ ID NO 74
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 74

Ala His Val Glu Ile Thr Leu Met Trp Gln Arg Ala Lys Trp
1               5                   10

<210> SEQ ID NO 75
```

```
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 75

Val Asn Ala Leu Ile Gln His Met His Gln Arg Ala Lys Trp
1               5                   10

<210> SEQ ID NO 76
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 76

Glu Ser Ala Glu Ile Gln Leu Met His Gln Ile Ala Ile Trp
1               5                   10

<210> SEQ ID NO 77
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 77

Thr Ile Pro Glu Leu Ala Thr Leu Gln Phe Phe His Gln Trp
1               5                   10

<210> SEQ ID NO 78
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 78

Thr Ile Pro Glu Ile Ala Thr Leu Gln Gln Thr Leu Ile Phe
1               5                   10

<210> SEQ ID NO 79
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 79

Thr Ile Pro Glu Ile Glu Thr Leu Gln Gln Met Leu Ile Trp
1               5                   10

<210> SEQ ID NO 80
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 80

Thr Ile Met Glu Ile Ala Thr Leu Gln Gln Thr Leu Ile Trp
1               5                   10

<210> SEQ ID NO 81
<211> LENGTH: 14
```

```
<212> TYPE: PRT
<213> ORGANISM: Artificial Sequence
<220> FEATURE:
<223> OTHER INFORMATION: synthetic parathyroid hormone polypeptide

<400> SEQUENCE: 81

Thr Ile Met Glu Ile Asn Thr Leu Gln Gln Phe Leu Ile Trp
1               5                   10

<210> SEQ ID NO 82
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 82

Thr Ile Met Glu Ile Asn Thr Leu Gln Gln Met Leu Ile Trp
1               5                   10

<210> SEQ ID NO 83
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 83

Thr Ile Met Glu Ile Glu Thr Leu Gln Gln Met Leu Ile Trp
1               5                   10

<210> SEQ ID NO 84
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 84

Thr Ile Met Glu Ile Glu Thr Leu Asp Gln Phe Leu Tyr Trp
1               5                   10

<210> SEQ ID NO 85
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 85

Thr Ile Met Glu Ile Glu Thr Leu Asp Gln Met Leu Ile Trp
1               5                   10

<210> SEQ ID NO 86
<211> LENGTH: 14
<212> TYPE: PRT
<213> ORGANISM: Artificial Sequence
<220> FEATURE:
<223> OTHER INFORMATION: synthetic parathyroid hormone polypeptide

<400> SEQUENCE: 86

Thr Ile Met Glu Ile Glu Thr Leu Asp Phe Met Leu Ile Lys
1               5                   10

<210> SEQ ID NO 87
<211> LENGTH: 14
<212> TYPE: PRT
```

```
<213> ORGANISM: Artificial Sequence
<220> FEATURE:
<223> OTHER INFORMATION: synthetic parathyroid hormone polypeptide

<400> SEQUENCE: 87

Thr Ile Met Glu Ile Glu Gly Leu Asp Gln Met Leu Tyr Lys
1               5                   10

<210> SEQ ID NO 88
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 88

Val Asp Phe Glu Leu Trp Leu Leu Gln Gln Met Leu Leu Phe Glu Leu
1               5                   10                  15

Tyr Tyr Glu Ile Ile Glu Thr Leu Leu Lys Leu Ile Glu Glu Ile Phe
                20                  25                  30

<210> SEQ ID NO 89
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 89

Thr Val Phe Glu Leu Trp Leu Leu Gln Gln Met Trp Asp Phe Glu Arg
1               5                   10                  15

Arg Phe Glu Val Leu Arg Glu Phe Leu Lys Leu Leu Glu Glu Ile Phe
                20                  25                  30

<210> SEQ ID NO 90
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 90

Thr Val Phe Glu Ile Trp Leu Leu Gln Gln Met His Asp Phe Glu Lys
1               5                   10                  15

Arg Phe Glu Val Leu Arg Met Leu Leu Glu Leu Leu Arg Glu Ile Phe
                20                  25                  30

<210> SEQ ID NO 91
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 91

Ile Asn Phe Glu Ile Trp Leu Ile Thr Gln Phe His Leu Phe Glu Lys
1               5                   10                  15

Tyr Tyr Glu Ile Arg Glu Thr Leu Leu Lys Leu Ile Glu Glu Ile Phe
                20                  25                  30

<210> SEQ ID NO 92
<211> LENGTH: 32
<212> TYPE: PRT
<213> ORGANISM: Artificial Sequence
<220> FEATURE:
```

<223> OTHER INFORMATION: synthetic parathyroid hormone polypeptide

<400> SEQUENCE: 92

Val Asp Phe Glu Ile Trp Leu Leu Gln Gln Met Trp Ile Leu Arg Thr
1               5                   10                  15

Leu Cys Glu Arg Arg Glu Glu Leu Leu Lys Leu Ile Glu Glu Ile Phe
                20                  25                  30

<210> SEQ ID NO 93
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 93

Ile Asp Tyr Glu Ile Trp Leu Ile Thr Gln Phe Ala Ile Phe Glu Leu
1               5                   10                  15

Asn Tyr Glu Arg Arg Glu Glu Leu Leu Lys Leu Ile Glu Glu Ile Phe
                20                  25                  30

<210> SEQ ID NO 94
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 94

Val Pro Phe Glu Leu Trp Leu Leu His Gln Met Leu Lys Phe Glu Leu
1               5                   10                  15

Asp Tyr Glu Arg Arg Glu Glu Leu Leu Lys Leu Ile Glu Glu Ile Phe
                20                  25                  30

<210> SEQ ID NO 95
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 95

Val Asn Phe Glu Ile Trp Leu Leu Gln Gln Arg Ala Leu Glu Glu Ala
1               5                   10                  15

Leu Asn Arg Ile Arg Asp Phe Leu Leu Lys Leu Ile Glu Glu Ile Phe
                20                  25                  30

<210> SEQ ID NO 96
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 96

Arg Asp Val Glu Ile Glu Leu Leu Glu Gln Leu Leu Gln Trp Ile Ile
1               5                   10                  15

Asp Tyr Arg Ile Arg Glu Phe Leu Leu Lys Leu Ile Glu Glu Ile Phe
                20                  25                  30

<210> SEQ ID NO 97
<211> LENGTH: 32
<212> TYPE: PRT
<213> ORGANISM: Artificial Sequence

```
<220> FEATURE:
<223> OTHER INFORMATION: synthetic parathyroid hormone polypeptide

<400> SEQUENCE: 97

Arg Asp Val Glu Ile Glu Leu Leu Glu Gln Leu Ala Gln Trp Ile Leu
1               5                   10                  15

Asp Tyr Arg Ile Arg Glu Phe Leu Leu Lys Leu Ile Glu Glu Ile Phe
            20                  25                  30

<210> SEQ ID NO 98
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 98

Thr Asn Phe Glu Ile Trp Leu Leu Ser Gln Leu Ala Lys Trp Ile Val
1               5                   10                  15

Glu Tyr Arg Arg Arg Glu Phe Leu Leu Lys Leu Ile Glu Glu Ile Phe
            20                  25                  30

<210> SEQ ID NO 99
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 99

Val Asn Phe Glu Ile Trp Leu Met Gln Gln Leu Ala Gln Trp Ile Ala
1               5                   10                  15

Asp Tyr Arg Arg Arg Glu Glu Leu Asp Lys Leu Ile Ala Glu Ile Phe
            20                  25                  30

<210> SEQ ID NO 100
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 100

Ile Asp Tyr Glu Ile Met Leu Leu His Gln Leu Leu Lys Trp Ile Ile
1               5                   10                  15

Asp Tyr Arg Arg Arg Glu Phe Leu His Lys Leu Ile Glu Glu Ile Phe
            20                  25                  30

<210> SEQ ID NO 101
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 101

Val Asp Phe Glu Ile Gln Leu Met Gln Gln Arg Ala Gln Trp Ile Ala
1               5                   10                  15

Asp Tyr Arg Ile Arg Glu Phe Leu Asp Lys Leu Ile Ala Glu Ile Phe
            20                  25                  30

<210> SEQ ID NO 102
<211> LENGTH: 32
<212> TYPE: PRT
```

```
<213> ORGANISM: Artificial Sequence
<220> FEATURE:
<223> OTHER INFORMATION: synthetic parathyroid hormone polypeptide

<400> SEQUENCE: 102

Ala Val Ala Glu Ile Gln Leu Met His Gln Arg Ala Lys Trp Glu Leu
1               5                   10                  15

Glu Tyr Glu Leu Phe Glu Met Phe Leu Lys Leu Leu Glu Glu Ile Phe
            20                  25                  30

<210> SEQ ID NO 103
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 103

Ala Val Ala Glu Ile Gln Leu Met His Gln Arg Ala Lys Trp Arg Ala
1               5                   10                  15

Glu Tyr Glu Leu Arg Glu Met Leu Leu Arg Leu Leu Glu Glu Ile Phe
            20                  25                  30

<210> SEQ ID NO 104
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 104

Ala Val Ala Glu Ile Gln Leu Met His Gln Arg Ala Lys Trp Glu Leu
1               5                   10                  15

Glu Phe Glu Leu Phe Arg Glu Phe Leu Lys Leu Leu Val Asp Phe Phe
            20                  25                  30

<210> SEQ ID NO 105
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 105

Ala Val Ala Glu Ile Gln Leu Met His Gln Arg Ala Lys Trp Glu Tyr
1               5                   10                  15

Tyr Tyr Glu Ile Leu Glu Met Leu Leu Arg Leu Leu Arg Glu Ile Tyr
            20                  25                  30

<210> SEQ ID NO 106
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 106

Ala Val Ala Glu Ile Gln Leu Met His Gln Arg Ala Lys Trp Glu Leu
1               5                   10                  15

Glu Tyr Tyr Leu Phe Glu Thr Phe Leu Lys Met Leu Glu Glu Val Phe
            20                  25                  30

<210> SEQ ID NO 107
<211> LENGTH: 14
```

```
<212> TYPE: PRT
<213> ORGANISM: Artificial Sequence
<220> FEATURE:
<223> OTHER INFORMATION: 14-mer consensus sequence for synthetic
      parathyroid hormone polypeptide
<220> FEATURE:
<221> NAME/KEY: MISC_FEATURE
<222> LOCATION: (1)..(1)
<223> OTHER INFORMATION: V, T, or A
<220> FEATURE:
<221> NAME/KEY: MISC_FEATURE
<222> LOCATION: (2)..(2)
<223> OTHER INFORMATION: D or V
<220> FEATURE:
<221> NAME/KEY: MISC_FEATURE
<222> LOCATION: (3)..(3)
<223> OTHER INFORMATION: F, Y, or V
<220> FEATURE:
<221> NAME/KEY: MISC_FEATURE
<222> LOCATION: (6)..(6)
<223> OTHER INFORMATION: W, F, M, or A
<220> FEATURE:
<221> NAME/KEY: MISC_FEATURE
<222> LOCATION: (7)..(7)
<223> OTHER INFORMATION: L or T
<220> FEATURE:
<221> NAME/KEY: MISC_FEATURE
<222> LOCATION: (10)..(10)
<223> OTHER INFORMATION: F, Q, or H
<220> FEATURE:
<221> NAME/KEY: MISC_FEATURE
<222> LOCATION: (11)..(11)
<223> OTHER INFORMATION: F, L, or T
<220> FEATURE:
<221> NAME/KEY: MISC_FEATURE
<222> LOCATION: (12)..(12)
<223> OTHER INFORMATION: L, H, or A
<220> FEATURE:
<221> NAME/KEY: MISC_FEATURE
<222> LOCATION: (13)..(13)
<223> OTHER INFORMATION: L, E, or Q
<220> FEATURE:
<221> NAME/KEY: MISC_FEATURE
<222> LOCATION: (14)..(14)
<223> OTHER INFORMATION: F or W

<400> SEQUENCE: 107

Xaa Xaa Xaa Glu Leu Xaa Xaa Leu Gln Xaa Xaa Xaa Xaa Xaa
1               5                   10

<210> SEQ ID NO 108
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 108

Gly Val Ala Glu Leu Gln Leu Met His Asp Leu Ala Lys Ile Arg Ala
1               5                   10                  15

Glu Tyr Glu Leu Arg Glu Met Leu Leu Arg Leu Leu Glu Glu Ile Phe
                20                  25                  30

<210> SEQ ID NO 109
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 109

Gly Val Ala Met Ile Gln Ile Met His Asp Ile Ala Lys Ile Arg Ala
1               5                   10                  15
```

Glu Tyr Glu Leu Arg Glu Met Leu Leu Arg Leu Leu Glu Glu Ile Phe
            20                  25                  30

<210> SEQ ID NO 110
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 110

Gly Val Ala Glu Ile Gln Leu Met His Asp Ile Pro Val Ile Arg Ala
1               5                   10                  15

Glu Tyr Glu Leu Arg Glu Met Leu Leu Arg Leu Leu Glu Glu Ile Phe
            20                  25                  30

<210> SEQ ID NO 111
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 111

Gly Val Ser Met Leu Gln Ile Met His Asp Leu Ala Val Ile Arg Ala
1               5                   10                  15

Glu Tyr Glu Leu Arg Glu Met Leu Leu Arg Leu Leu Glu Glu Ile Phe
            20                  25                  30

<210> SEQ ID NO 112
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 112

Gly Val Ala Leu Leu Gln Ile Val His Asp Phe Ala Lys Ile Arg Ala
1               5                   10                  15

Glu Tyr Glu Leu Arg Glu Met Leu Leu Arg Leu Leu Glu Glu Ile Phe
            20                  25                  30

<210> SEQ ID NO 113
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 113

Ala Val Ala Thr Ile Gln Leu Met Thr Asp Ile Ala Lys Ile Arg Ala
1               5                   10                  15

Glu Tyr Glu Leu Arg Glu Met Leu Leu Arg Leu Leu Glu Glu Ile Phe
            20                  25                  30

<210> SEQ ID NO 114
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 114

Gly Val Ala Glu Leu Gln Leu Met His Phe Arg Ala Leu Leu Arg Ala

```
1               5                   10                  15

Glu Tyr Glu Leu Arg Glu Met Leu Leu Arg Leu Leu Glu Glu Ile Phe
            20                  25                  30
```

<210> SEQ ID NO 115
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 115

```
Ser Val Met Met Ile Gln Val Met His Asp Leu Ala Lys Ile Arg Ala
1               5                   10                  15

Glu Tyr Glu Leu Arg Glu Met Leu Leu Arg Leu Leu Glu Glu Ile Phe
            20                  25                  30
```

<210> SEQ ID NO 116
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 116

```
Gly Val Val Met Leu Gln Phe Met His Asp Val Ala Lys Ile Arg Ala
1               5                   10                  15

Glu Tyr Glu Leu Arg Glu Met Leu Leu Arg Leu Leu Glu Glu Ile Phe
            20                  25                  30
```

<210> SEQ ID NO 117
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 117

```
Gly Val Tyr Ala Ile Gln Ala Met His Asp Leu Ala Lys Ile Arg Ala
1               5                   10                  15

Glu Tyr Glu Leu Arg Glu Met Leu Leu Arg Leu Leu Glu Glu Ile Phe
            20                  25                  30
```

<210> SEQ ID NO 118
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 118

```
Gly Val Ala Met Leu Gln Ile Leu His Asp Lys Ala Lys Val Arg Ala
1               5                   10                  15

Glu Tyr Glu Leu Arg Glu Met Leu Leu Arg Leu Leu Glu Glu Ile Phe
            20                  25                  30
```

<210> SEQ ID NO 119
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 119

Gly Val Ala Glu Ile Gln Leu Met Val Asp Leu Asp Ile Ile Arg Ala
1               5                   10                  15

Glu Tyr Glu Leu Arg Glu Met Leu Leu Arg Leu Leu Glu Glu Ile Phe
            20                  25                  30

<210> SEQ ID NO 120
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 120

Gly Ile Ala Val Ile Thr Leu Met Asp Leu Arg Ala Tyr Leu Arg Ala
1               5                   10                  15

Glu Tyr Glu Leu Arg Glu Met Leu Leu Arg Leu Leu Glu Glu Ile Phe
            20                  25                  30

<210> SEQ ID NO 121
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 121

Gly Ile Ala Val Leu Thr Ile Leu Asp Leu Arg Ala Lys Leu Arg Ala
1               5                   10                  15

Glu Tyr Glu Leu Arg Glu Met Leu Leu Arg Leu Leu Glu Glu Ile Phe
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 122

Gly Val Ala Val Val Thr Leu Met Val Leu Arg Ala Tyr Tyr Arg Ala
1               5                   10                  15

Glu Tyr Glu Leu Arg Glu Met Leu Leu Arg Leu Leu Glu Glu Ile Phe
            20                  25                  30

<210> SEQ ID NO 123
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 123

Leu Ile Leu Val Glu Gln Leu Met Asp Leu Arg Ala Tyr Leu Arg Ala
1               5                   10                  15

Glu Tyr Glu Leu Arg Glu Met Leu Leu Arg Leu Leu Glu Glu Ile Phe
            20                  25                  30

<210> SEQ ID NO 124
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 124

```
Gly Ile Ala Val Phe Thr Ile Met His Leu Arg Ile Tyr Leu Arg Ala
1               5                   10                  15

Glu Tyr Glu Leu Arg Glu Met Leu Leu Arg Leu Leu Glu Glu Ile Phe
            20                  25                  30
```

<210> SEQ ID NO 125
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 125

```
Ser Ile Ile Gly Glu Gln Leu Met Leu Leu Arg Ala Leu Leu Arg Ala
1               5                   10                  15

Glu Tyr Glu Leu Arg Glu Met Leu Leu Arg Leu Leu Glu Glu Ile Phe
            20                  25                  30
```

<210> SEQ ID NO 126
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 126

```
Pro Ile Pro Val Lys Asp Ile Met Asp Leu Arg Ala Tyr Leu Arg Ala
1               5                   10                  15

Glu Tyr Glu Leu Arg Glu Met Leu Leu Arg Leu Leu Glu Glu Ile Phe
            20                  25                  30
```

<210> SEQ ID NO 127
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 127

```
Asn Ile Ala Val Glu Tyr Ile Met Leu Leu Arg Ala Tyr Leu Arg Ala
1               5                   10                  15

Glu Tyr Glu Leu Arg Glu Met Leu Leu Arg Leu Leu Glu Glu Ile Phe
            20                  25                  30
```

<210> SEQ ID NO 128
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 128

```
Leu Ile Leu Val Lys Lys Ile Ile Asp Leu Arg Ala Tyr Leu Arg Ala
1               5                   10                  15

Glu Tyr Glu Leu Arg Glu Met Leu Leu Arg Leu Leu Glu Glu Ile Phe
            20                  25                  30
```

<210> SEQ ID NO 129
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 129

Gly Ile Ala Val Ile Thr Ile Met Ile Asp Tyr Ala Lys Leu Arg Ala
1               5                   10                  15

Glu Tyr Glu Leu Arg Glu Met Leu Leu Arg Leu Leu Glu Glu Ile Phe
                20                  25                  30

<210> SEQ ID NO 130
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 130

Gly Ile Ala Val Glu Thr Leu Met Glu Leu Arg Ala Phe Val Arg Ala
1               5                   10                  15

Glu Tyr Glu Leu Arg Glu Met Leu Leu Arg Leu Leu Glu Glu Ile Phe
                20                  25                  30

<210> SEQ ID NO 131
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 131

Gly Leu Ala Ala Leu Thr Ile Gly Leu Leu Arg Ala Lys Leu Arg Ala
1               5                   10                  15

Glu Tyr Glu Leu Arg Glu Met Leu Leu Arg Leu Leu Glu Glu Ile Phe
                20                  25                  30

<210> SEQ ID NO 132
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 132

Ala Val Ala Glu Ile Gln Leu Met His Gln Arg Ala Lys Trp Lys Leu
1               5                   10                  15

Glu Leu Glu Leu Lys Val Lys Leu Leu Glu Ile Leu Lys Asp Val Tyr
                20                  25                  30

<210> SEQ ID NO 133
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 133

Ala Val Ala Glu Ile Gln Leu Met His Gln Arg Ala Lys Trp Gly Leu
1               5                   10                  15

Glu Leu Glu Leu Lys Glu Lys Leu Arg Lys Ile Leu Glu Asp Val Tyr
                20                  25                  30

<210> SEQ ID NO 134
<211> LENGTH: 32
<212> TYPE: PRT
<213> ORGANISM: Artificial Sequence
<220> FEATURE:
<223> OTHER INFORMATION: synthetic parathyroid hormone polypeptide

```
<400> SEQUENCE: 134

Ala Val Ala Glu Ile Gln Leu Met His Gln Arg Ala Lys Trp Lys Leu
1               5                   10                  15

Asp Leu Glu Leu Ala Val Ser Leu Arg Lys Ile Leu Glu Asp Val Tyr
            20                  25                  30

<210> SEQ ID NO 135
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 135

Ala Val Ala Glu Ile Gln Leu Met His Gln Arg Ala Lys Trp Gly Leu
1               5                   10                  15

Asp Leu Glu Leu Ala Val Lys Leu Gln Glu Ile Leu Lys Asp Val Leu
            20                  25                  30

<210> SEQ ID NO 136
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 136

Ala Val Ala Glu Ile Gln Leu Met His Gln Arg Ala Lys Trp Lys Leu
1               5                   10                  15

Glu Leu Glu Leu Lys Glu Lys Ile Arg Lys Leu Leu Glu Asp Leu Leu
            20                  25                  30

<210> SEQ ID NO 137
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 137

Ala Val Ala Glu Ile Gln Leu Met His Gln Arg Ala Lys Trp Leu Glu
1               5                   10                  15

Glu Leu Lys Leu Lys Asp Asp Leu Arg Lys Ile Leu Glu Asp Val Tyr
            20                  25                  30

<210> SEQ ID NO 138
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 138

Ala Val Ala Glu Ile Gln Leu Met His Gln Arg Ala Lys Trp Gly Leu
1               5                   10                  15

Asp Leu Glu Leu Arg Ala Arg Leu Arg Glu Ile Leu Arg Asp Val Tyr
            20                  25                  30

<210> SEQ ID NO 139
<211> LENGTH: 32
<212> TYPE: PRT
<213> ORGANISM: Artificial Sequence
<220> FEATURE:
```

```
<223> OTHER INFORMATION: synthetic parathyroid hormone polypeptide

<400> SEQUENCE: 139

Ala Val Ala Glu Ile Gln Leu Met His Gln Arg Ala Lys Trp Lys Gln
1               5                   10                  15

Glu Leu Glu Leu Glu Glu Lys Asn Lys Lys Ile Leu Glu Asp Val Tyr
            20                  25                  30

<210> SEQ ID NO 140
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 140

Ala Val Ala Glu Ile Gln Leu Met His Gln Arg Ala Lys Trp Leu Asn
1               5                   10                  15

Glu Leu Arg Leu Lys Glu Glu Met Arg Lys Ile Leu Glu Asp Val Tyr
            20                  25                  30

<210> SEQ ID NO 141
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 141

Ala Val Ala Glu Ile Gln Leu Met His Gln Arg Ala Lys Trp Arg Leu
1               5                   10                  15

Glu Ile Glu Leu Leu Lys Lys Leu Lys Glu Ile Leu Lys Asp Val Tyr
            20                  25                  30

<210> SEQ ID NO 142
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 142

Ala Val Ala Glu Ile Gln Leu Met His Gln Arg Ala Lys Trp Gly Val
1               5                   10                  15

Glu Leu Gln Leu Lys Val Asp Leu Arg Arg Ile Leu Glu Asp Val Tyr
            20                  25                  30

<210> SEQ ID NO 143
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 143

Ala Val Ala Glu Ile Gln Leu Met His Gln Arg Ala Lys Trp Lys Leu
1               5                   10                  15

Glu Leu Glu Leu Lys Ala Phe Leu Asp Gln Ile Leu Lys Asp Val Leu
            20                  25                  30

<210> SEQ ID NO 144
<211> LENGTH: 32
<212> TYPE: PRT
<213> ORGANISM: Artificial Sequence
```

```
<220> FEATURE:
<223> OTHER INFORMATION: synthetic parathyroid hormone polypeptide

<400> SEQUENCE: 144

Ala Val Ala Glu Ile Gln Leu Met His Gln Arg Ala Lys Trp Glu Ile
1               5                   10                  15

Gln Glu Ile Gly Ile Lys Ile Thr Leu Glu Leu Leu Lys Glu Tyr Ile
            20                  25                  30

<210> SEQ ID NO 145
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 145

Ala Val Ala Glu Ile Gln Leu Met His Gln Arg Ala Lys Trp Glu Leu
1               5                   10                  15

Leu Glu Glu Leu Leu Lys Ile Leu Leu Glu Leu Leu Lys Glu Tyr Ile
            20                  25                  30

<210> SEQ ID NO 146
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 146

Ala Val Ala Glu Ile Gln Leu Met His Gln Arg Ala Lys Trp Glu Leu
1               5                   10                  15

Gln Glu Ile Gly Ile Lys Ile Thr Leu Asp Leu Leu Glu Ala Tyr Leu
            20                  25                  30

<210> SEQ ID NO 147
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 147

Ala Val Ala Glu Ile Gln Leu Met His Gln Arg Ala Lys Trp Asp Leu
1               5                   10                  15

Leu Ile Glu Leu Val Lys Leu Leu His Glu Leu Leu Lys Glu Tyr Ile
            20                  25                  30

<210> SEQ ID NO 148
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 148

Ala Val Ala Glu Ile Gln Leu Met His Gln Arg Ala Lys Trp Glu Ile
1               5                   10                  15

Gln Glu Ile Gly Ile Lys Ile Thr Leu Asp Leu Leu Gln Thr Leu Lys
            20                  25                  30

<210> SEQ ID NO 149
<211> LENGTH: 32
<212> TYPE: PRT
```

<213> ORGANISM: Artificial Sequence
<220> FEATURE:
<223> OTHER INFORMATION: synthetic parathyroid hormone polypeptide

<400> SEQUENCE: 149

Ala Val Ala Glu Ile Gln Leu Met His Gln Arg Ala Lys Trp Ala Ile
1               5                   10                  15

Gln Glu Ile Gly Ile Lys Ile Thr Arg Glu Leu Leu Glu Arg Tyr Leu
            20                  25                  30

<210> SEQ ID NO 150
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 150

Ala Val Ala Glu Ile Gln Leu Met His Gln Arg Ala Lys Trp Glu Leu
1               5                   10                  15

Gln Glu Ile Gly Ile Ala Ile Thr Leu Arg Leu Leu Ala Arg Tyr Ile
            20                  25                  30

<210> SEQ ID NO 151
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 151

Ala Val Ala Glu Ile Gln Leu Met His Gln Arg Ala Lys Trp Ser Leu
1               5                   10                  15

Arg Glu Glu Leu Glu Lys Leu Leu Lys Glu Leu Leu Lys Glu Tyr Ile
            20                  25                  30

<210> SEQ ID NO 152
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 152

Ala Val Ala Glu Ile Gln Leu Met His Gln Arg Ala Lys Trp Gly Leu
1               5                   10                  15

Glu Ile Glu Leu Leu Lys Leu Leu Leu Ser Leu Leu Lys Glu Tyr Ile
            20                  25                  30

<210> SEQ ID NO 153
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 153

Ala Val Ala Glu Ile Gln Leu Met His Gln Arg Ala Lys Trp Ser Ile
1               5                   10                  15

Leu Glu Glu Leu Leu Lys Ile Leu Thr Ala Leu Leu Asp Glu Tyr Ile
            20                  25                  30

<210> SEQ ID NO 154
<211> LENGTH: 32

```
<212> TYPE: PRT
<213> ORGANISM: Artificial Sequence
<220> FEATURE:
<223> OTHER INFORMATION: synthetic parathyroid hormone polypeptide

<400> SEQUENCE: 154

Ala Val Ala Glu Ile Gln Leu Met His Gln Arg Ala Lys Trp Asp Val
1               5                   10                  15

Leu Ile Glu Leu Ala Lys Leu Leu Ala Glu Leu Leu Arg Arg Tyr His
            20                  25                  30

<210> SEQ ID NO 155
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 155

Ala Val Ala Glu Ile Gln Leu Met His Gln Arg Ala Lys Trp Lys Ile
1               5                   10                  15

Leu Glu Glu Leu Leu Lys Ile Leu Ile Asp Leu Leu Lys Gln Tyr Ile
            20                  25                  30

<210> SEQ ID NO 156
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 156

Gly Val Ala Glu Leu Gln Leu Met His Asp Leu Ala Lys Ile Lys Leu
1               5                   10                  15

Glu Leu Glu Leu Lys Val Lys Leu Leu Glu Ile Leu Lys Asp Val Tyr
            20                  25                  30

<210> SEQ ID NO 157
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 157

Gly Val Ala Met Leu Gln Ile Met His Asp Leu Ala Lys Ile Lys Gln
1               5                   10                  15

Glu Leu Glu Leu Lys Asp Ser Met Lys Lys Ile Leu Glu Asp Val Leu
            20                  25                  30

<210> SEQ ID NO 158
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 158

Gly Ile Ala Val Ile Thr Leu Met Val Leu Arg Ala Leu Leu Glu Leu
1               5                   10                  15

Gln Glu Ile Gly Arg Lys Ile Thr Leu Glu Leu Leu Lys Glu Tyr Ile
            20                  25                  30

<210> SEQ ID NO 159
```

```
<211> LENGTH: 32
<212> TYPE: PRT
<213> ORGANISM: Artificial Sequence
<220> FEATURE:
<223> OTHER INFORMATION: synthetic parathyroid hormone polypeptide

<400> SEQUENCE: 159

Gly Ile Ala Val Ile Thr Leu Met Leu Leu Arg Ala Tyr Leu Glu Leu
1               5                   10                  15

Leu Glu Glu Leu Val Lys Ile Leu His Glu Leu Leu Arg Arg Tyr His
            20                  25                  30

<210> SEQ ID NO 160
<211> LENGTH: 34
<212> TYPE: PRT
<213> ORGANISM: Artificial Sequence
<220> FEATURE:
<223> OTHER INFORMATION: synthetic parathyroid hormone polypeptide

<400> SEQUENCE: 160

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Tyr
```